·

US010907214B2

(12) United States Patent
Knudsen

(10) Patent No.: US 10,907,214 B2
(45) Date of Patent: Feb. 2, 2021

(54) METHODS FOR PREDICTING DRUG RESPONSIVENESS IN CANCER PATIENTS

(71) Applicant: Oncology Venture ApS, Hørsholm (DK)

(72) Inventor: Steen Knudsen, Scottsdale, AZ (US)

(73) Assignee: Oncology Venture ApS, Hørsholm (DK)

(*) Notice: Subject to any disclaimer, the term of this patent is extended or adjusted under 35 U.S.C. 154(b) by 86 days.

(21) Appl. No.: 15/858,703

(22) Filed: Dec. 29, 2017

(65) Prior Publication Data
US 2018/0202004 A1 Jul. 19, 2018

Related U.S. Application Data

(60) Provisional application No. 62/440,883, filed on Dec. 30, 2016.

(51) Int. Cl.
C12Q 1/6886 (2018.01)
C12Q 1/6813 (2018.01)

(52) U.S. Cl.
CPC ......... *C12Q 1/6886* (2013.01); *C12Q 1/6813* (2013.01); *C12Q 2600/136* (2013.01); *C12Q 2600/142* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,880,635 A | 11/1989 | Janoff et al. | |
| 4,963,362 A | 10/1990 | Rahman et al. | |
| 5,858,397 A | 1/1999 | Lim et al. | |
| 6,027,726 A | 2/2000 | Ansell | |
| 6,911,306 B1 | 6/2005 | Vertino | |
| 7,239,986 B2 | 7/2007 | Golub et al. | |
| 7,273,620 B1 | 9/2007 | Zhigaltsev et al. | |
| 7,709,616 B2 | 5/2010 | Bentwich et al. | |
| 8,445,198 B2 | 5/2013 | Knudsen | |
| 9,598,734 B2 | 3/2017 | Knudsen | |
| 9,725,769 B1 | 8/2017 | Knudsen | |
| 9,820,941 B2 | 11/2017 | Madsen et al. | |
| 2001/0051344 A1 | 12/2001 | Shalon et al. | |
| 2002/0164663 A1 | 11/2002 | Fuqua et al. | |
| 2003/0026831 A1 | 2/2003 | Lakkaraju et al. | |
| 2003/0073083 A1 | 4/2003 | Tamayo et al. | |
| 2003/0147945 A1 | 8/2003 | Tardi et al. | |
| 2004/0018525 A1 | 1/2004 | Wirtz et al. | |
| 2004/0022842 A1 | 2/2004 | Eriguchi et al. | |
| 2004/0072722 A1 | 4/2004 | Kornblith et al. | |
| 2005/0118250 A1 | 6/2005 | Tardi et al. | |
| 2005/0176669 A1 | 8/2005 | Al-Murrani | |
| 2005/0222396 A1 | 10/2005 | Bao et al. | |
| 2005/0260586 A1 | 11/2005 | Demuth et al. | |
| 2005/0260646 A1 | 11/2005 | Baker et al. | |
| 2006/0105360 A1 | 5/2006 | Croce et al. | |
| 2006/0121511 A1 | 6/2006 | Lee et al. | |
| 2007/0172844 A1 | 7/2007 | Lancaster et al. | |
| 2007/0286898 A1 | 12/2007 | Takagi et al. | |
| 2008/0085295 A1 | 4/2008 | Melvik et al. | |
| 2008/0227663 A1 | 9/2008 | Tisone et al. | |
| 2008/0306006 A1 | 12/2008 | Croce et al. | |
| 2009/0023149 A1 | 1/2009 | Knudsen | |
| 2009/0162425 A1 | 6/2009 | Divi et al. | |
| 2009/0221435 A1 | 9/2009 | Baskerville et al. | |
| 2009/0239223 A1 | 9/2009 | Gehrmann et al. | |
| 2010/0189771 A1 | 7/2010 | Mayer et al. | |
| 2010/0240043 A1 | 9/2010 | Rotter et al. | |
| 2011/0123990 A1 | 5/2011 | Baker et al. | |
| 2012/0009243 A1 | 1/2012 | Vikbjerg et al. | |
| 2012/0046186 A1 | 2/2012 | Pelham et al. | |
| 2012/0177726 A1 | 7/2012 | Petersen et al. | |
| 2012/0214703 A1 | 8/2012 | Croce et al. | |
| 2012/0302626 A1 | 11/2012 | Dave et al. | |
| 2013/0053275 A1 | 2/2013 | Knudsen | |
| 2013/0059015 A1 | 3/2013 | Lancaster et al. | |
| 2014/0294730 A1 | 10/2014 | Slack-Davis et al. | |
| 2015/0353928 A1 | 12/2015 | Weiner | |
| 2016/0199399 A1 | 7/2016 | Knudsen | |
| 2017/0283884 A1 | 10/2017 | Knudsen | |

(Continued)

FOREIGN PATENT DOCUMENTS

| | | |
|---|---|---|
| CA | 2428112 A1 | 11/2003 |
| CN | 102002490 A | 4/2011 |
| EP | 1550731 A1 | 7/2005 |

(Continued)

OTHER PUBLICATIONS

ClinicalTrials.gov. "Phase I/II study to Evaluate the Safety and Tolerability of LiPlaCis in Patients with Advanced or Refractory Tumours (LiPlaCis)," available via URL: <://clinicaltrials.gov/ct2/show/record/NCT01861496>; printed on Jan. 9, 2020.*
Dermer, G.B. Bio/Technology (1994) 12: 320.*
Arienti et al., "Activity of lipoplatin in tumor and in normal cells in vitro," Anti-Cancer Drugs. 19(10):983-990 (2008) (8 pages).
Boulikas, "Clinical overview on Lipoplatin™: a successful liposomal formulation of cisplatin," Expert Opinion on Investigational Drugs, 18(8):1197-1218 (2009) (23 pages).

(Continued)

*Primary Examiner* — Carla J Myers
(74) *Attorney, Agent, or Firm* — Clark & Elbing LLP

(57) ABSTRACT

The present invention features methods, devices, and kits for detecting a level of one or more biomarkers in a patient having cancer or determining the responsiveness of a patient having cancer to a treatment, such as treatment with a secretory phospholipase $A_2$ ($sPLA_2$) hydrolysable, cisplatin-containing liposome. The invention further includes methods of treating a patient having cancer by administering, e.g., the liposome.

26 Claims, 1 Drawing Sheet
Specification includes a Sequence Listing.

(56) References Cited

U.S. PATENT DOCUMENTS

| | | |
|---|---|---|
| 2018/0087113 A1 | 3/2018 | Knudsen |
| 2018/0202004 A1 | 7/2018 | Knudsen |

FOREIGN PATENT DOCUMENTS

| | | |
|---|---|---|
| EP | 2008/073177 A2 | 7/2009 |
| EP | 2123258 A1 | 11/2009 |
| EP | 2081950 B1 | 3/2013 |
| JP | 2001-017171 A | 1/2001 |
| JP | 2002-531066 A | 9/2002 |
| JP | 2004-43446 A | 2/2004 |
| JP | 2005-530784 A | 10/2005 |
| KR | 2007-0036055 A | 4/2007 |
| RU | 2528247 C2 | 9/2014 |
| WO | WO-99/30686 A1 | 6/1999 |
| WO | WO-00/31930 A1 | 6/2000 |
| WO | WO-00/35473 A2 | 6/2000 |
| WO | WO-03/082078 A2 | 10/2003 |
| WO | WO-2005/000266 A2 | 1/2005 |
| WO | WO-2005/005601 A2 | 1/2005 |
| WO | WO-2005/014856 A1 | 2/2005 |
| WO | WO-2005/047534 A2 | 5/2005 |
| WO | WO-2005/066371 A2 | 7/2005 |
| WO | WO-2005/087948 A2 | 9/2005 |
| WO | WO-2005/094863 A1 | 10/2005 |
| WO | WO-2005/100606 A2 | 10/2005 |
| WO | WO-2007/072225 A2 | 6/2007 |
| WO | WO-2008/073177 A2 | 6/2008 |
| WO | WO-2008/073629 A2 | 6/2008 |
| WO | WO-2008/112283 A2 | 9/2008 |
| WO | WO-2008/138578 A2 | 11/2008 |
| WO | WO-2009/036332 A1 | 3/2009 |
| WO | WO-2009/080437 A1 | 7/2009 |
| WO | WO-2009/141450 A2 | 11/2009 |
| WO | WO-2011/032563 A1 | 3/2011 |
| WO | WO-2011/047689 A2 | 4/2011 |
| WO | WO-2011/098578 A2 | 8/2011 |
| WO | WO-2011/135459 A2 | 11/2011 |
| WO | WO-2012/024543 A1 | 2/2012 |
| WO | WO-2012/106718 A2 | 8/2012 |
| WO | WO-2012/109233 A2 | 8/2012 |
| WO | WO-2012/163541 A1 | 12/2012 |
| WO | WO-2013/130465 A2 | 9/2013 |
| WO | WO-2014/195032 A1 | 12/2014 |

OTHER PUBLICATIONS

Casagrande et al., "Preclinical Activity of the Liposomal Cisplatin Lipoplatin in Ovarian Cancer," Clin Cancer Res. 20(21):5496-5506 (12 pages).

De Jonge et al., "Early Cessation of the clinical development of LiPlaCis, a liposomal cisplatin formulation," Eur J Cancer. 46(16):3016-3021 (2010) (6 pages).

Oncology Venture Sweden AB, "Press release issued by Oncology Venture Sweden AB Oncology Venture Presents LiPlaCis on AACR in New Orleans," Mar. 4, 2016 (2 pages).

Extended European Search Report for European Patent Application No. 17211034.8, dated May 22, 2018 (13 pages).

Koeppel et al., "Irofulven cytotoxicity depends on transcription-coupled nucleotide excision repair and is correlated with XPG expression in solid tumor cells," Clin Cancer Res. 10(16):5604-13 (2004) (11 pages).

Liang et al., "Caspase-mediated apoptosis and caspase-independent cell death induced by irofulven in prostate cancer cells," Mol Cancer Ther. 3(11):1385-96 (2004) (12 pages).

Senzer et al., "Irofulven demonstrates clinical activity against metastatic hormone-refractory prostate cancer in a phase 2 single-agent trial," Am J Clin Oncol. 28(1):36-42 (2005).

Woynarowska et al., "Changes in prostate-specific antigen (PSA) level correlate with growth inhibition of prostate cancer cells treated in vitro with a novel anticancer drug, irofulven," Invest New Drugs. 19(4):283-91 (2001).

Ocio et al., "The Activation of Fas Receptor by APO010, a Recombinant Form of Fas Ligand, Induces In Vitro and In Vivo Antimyeloma Activity," Blood. 110(11):1515 (2007) (4 pages) (Abstract Only).

Wang et al., "Independent Validation of a Model Using Cell Line Chemosensitivity to Predict Response to Therapy," J Natl Cancer Inst. 105(17): 1284-91 (2013).

Narita et al., "Lower expression of activating transcription factors 3 and 4 correlates with shorter progression-free survival in multiple myeloma patients receiving bortezomib plus dexamethasone therapy," Blood Cancer J. 5:e373 (2015) (8 pages).

Medinger et al., "Gene-expression Profiling in Patients with Plasma Cell Myeloma Treated with Novel Agents," Cancer Genomics Proteomics.13(4):275-9 (2016).

Gerspach et al., "Therapeutic targeting of CD95 and the TRAIL death receptors," Recent Pat Anticancer Drug Discov. 6(3):294-310 (2011).

Vangsted et al., "APO010 sensitivity in relapsed multiple myeloma patients," Annals of Oncol. 27(Supplement 6): vi15-vi42 (2016) (2 pages) (Abstract only).

Extended European Search Report for European Patent Application No. 17193243.7, dated Feb. 2, 2018 (12 pages).

Extended European Search Report for European Application No. 18172585.4, dated Oct. 9, 2018 (7 pages).

Churchill Livingstone's Dictionary of Nursing, "Saline", http://www.credoreference.com/entry/ehscldictnursing/saline, retrieved Dec. 31, 2002.

Murakami et al., "Cellular components that functionally interact with signaling phospholipase A(2)s," Biochim Biophys Acta. 1488(1-2):159-66 (2000).

English Translation of Decision / Order of Hearing of the Patent Application for Indian Patent Application No. 4565/KOLNP/2010, dated Sep. 8, 2017 (1 page).

Liu et al., "Roles of USF, Ikaros and Sp proteins in the transcriptional regulation of the human reduced folate carrier B promoter," Biochem J. 383(Pt 2):249-57 (2004).

Office Action for Japanese Patent Application No. 2008-542865 dated Dec. 3, 2012 (12 pages).

Office Action for Chinese Patent Application No. 200680052220.2 dated Feb. 5, 2013.

Genbank: AY889152.1. Retrieved on Mar. 5, 2013 (2 pages).

Sezaki et al., "Over-expression of the dominant-negative isoform of Ikaros confers resistance to dexamethasone-induced and anti-IgM-induced apoptosis," Br J Haematol. 121(1):165-9 Abstract Only (2003).

Canadian Examination Report for Canadian Patent Application No. 2,631,236, dated Mar. 19, 2015 (6 pages).

Kuter et al., "Dose-dependent change in biomarkers during neoadjuvant endocrine therapy with fulvestrant: results from NEWEST, a randomized Phase II study," Breast Cancer Res Treat. 133(1):237-46 (2012).

Nikas et al., "Prognosis of treatment response (pathological complete response) in breast cancer," Biomark Insights. 7:59-70 (2012).

Juncker-Jensen et al., "Insulin-like growth factor binding protein 2 is a marker for antiestrogen resistant human breast cancer cell lines but is not a major growth regulator," Growth Horm IGF Res. 16(4):224-39 (2006).

McCune et al., "Prognosis of hormone-dependent breast cancers: implications of the presence of dysfunctional transcriptional networks activated by insulin via the immune transcription factor T-bet," Cancer Res. 70(2):685-96 (2010).

Agrawal et al., "Long-term effect of fulvestrant on hormone receptors and proliferation marker in breast cancer," EJC Supplements. 8(3):111 (2010).

International Search Report and Written Opinion for International Application No. PCT/EP2014/052236, dated Jul. 9, 2014 (21 pages).

International Preliminary Report on Patentability issued for International Application No. PCT/EP2015/052236, dated Dec. 8, 2015 (1 page).

Chow et al., "Increased expression of annexin I is associated with drug-resistance in nasopharyngeal carcinoma and other solid tumors," Proteomics Clin Appl. 3(6):654-62 (2009).

(56) References Cited

OTHER PUBLICATIONS

Buhl et al., "A genetic response profile to predict efficacy of adjuvant 5-fu in colon cancer," Annals of Oncology 25(Supplement 4):iv167-iv209 (2014) (1 page).
Invitation to Pay Additional Fees for International Application No. PCT/IB2015/002055, dated Mar. 29, 2016 (12 pages).
Mizutani et al., "Significance of orotate phosphoribosyltransferase activity in renal cell carcinoma," J Urol. 171(2 Pt 1):605-10 (2004).
Okumura et al., "Correlation between chemosensitivity and mRNA expression level of 5-fluorouracil-related metabolic enzymes during liver metastasis of colorectal cancer," Oncol Rep. 15(4):875-82 (2006).
Ooyama et al., "Gene expression analysis using human cancer xenografts to identify novel predictive marker genes for the efficacy of 5-fluorouracil-based drugs," Cancer Sci. 97(6):510-22 (2006).
International Search Report for International Patent Application No. PCT/IB2015/002055, dated Jun. 10, 2016 (10 pges).
International Preliminary Report on Patentability and Written Opinion for International Patent Application No. PCT/IB2015/002055, dated Mar. 28, 2017 (14 pages).
Bild et al., "Oncogenic pathway signatures in human cancers as a guide to targeted therapies," Nature. 439(7074):353-7 (2006).
Castelli et al., "In silico analysis of microRNAS targeting the HLA-G 3' untranslated region alleles and haplotypes," Hum Immunol. 70(12):1020-5 (2009).
Communication pursuant to Article 94(3) EPC for European Application No. 11741685.9, dated May 19, 2014 (6 pages).
Communication pursuant to Article 94(3) EPC in European Patent Application No. 06848658.8 dated Sep. 22, 2008 (6 pages).
Communication pursuant to Rule 94(3) EPC for European Application No. 11741685.9, dated Jul. 24, 2015 (7 pages).
Communication pursuant to Rules 161(1) and 162 EPC for European Application No. 11741685.9, dated Dec. 6, 2012 (2 pages).
Dahlén et al., "Activation of the GLI oncogene through fusion with the beta-actin gene (ACTB) in a group of distinctive pericytic neoplasms: pericytoma with t(7;12)," Am J Phathol. 164(5):1645-53 (2004).
Decision of Rejection for Japanese Application No. 2008-542865, dated Oct. 21, 2013 (11 pages).
Decision on Rejection for Chinese Application No. 200680052220.2, dated Jun. 5, 2013 (8 pages).
English Translation of Office Action for Chinese Patent Application No. 200680052220.2 dated Feb. 5, 2013 (9 pages).
English translation of Office Action for Chinese Patent Application No. 201280038428.4, dated Jan. 23, 2015 (15 pages).
English translation of Second Office Action for Chinese Patent Application No. 201280038428.4, dated Sep. 15, 2015 (10 pages).
EPO Communication pursuant to Article 94(3) EPC for European Patent Application No. 12725624.6, dated Dec. 23, 2014 (6 pages).
EPO Communication pursuant to Article 94(3) EPC for European Patent Application No. 12725624.6, dated Jul. 2, 2015 (4 pages).
EPO Communication Pursuant to Article 94(3) for European Application No. 12725624.6, dated Jul. 2, 2015 (4 pages).
Examination Report for Australian Patent Application No. 2011246976, dated Aug. 19, 2015 (3 pages).
Fournier et al., "Gene expression signature in organized and growth-arrested mammary acini predicts good outcome in breast cancer," Cancer Res. 66(14):7095-7102 (2006).
Friis-Hansen et al., "Mir-449 inhibits growth of gastric cancer cells partly by inhibiting the expression of met and amphiregulin," AGA Abstract No. 1072 (A-165).
Gallardo et al., "miR-34a as a prognostic marker of relapse in surgically resected non-small-cell lung cancer," Carcinogenesis. 30(11):1903-9 (2009).
Genbank Accession No. AY889152.1. Retrieved on Mar. 5, 2013 (2 pages).
International Preliminary Report on Patentability and Written Opinion of the International Searching Authority for International Application No. PCT/EP2012/002332 dated Dec. 2, 2013 (11 pages).
International Preliminary Report on Patentability and Written Opinion of the Searching Authority for International Patent Application No. PCT/EP2008/003789 dated Nov. 17, 2009 (9 pages).
International Preliminary Report on Patentability and Written Opinion of the Searching Authority for International Patent Application No. PCT/IB2006/004048 dated Jun. 4, 2008 (10 pages).
International Preliminary Report on Patentability for International Application No. PCT/IB2011/001405, dated Oct. 30, 2012 (13 pages).
International Search Report for International Application No. PCT/IB2006/004048 dated May 14, 2008 (5 pages).
International Search Report for International Application No. PCT/IB2011/001405, dated Apr. 19, 2012 (7 pages).
International Search Report for International Patent Application No. PCT/EP2008/003789 dated Jan. 9, 2009 (5 pages).
International Search Report for International Patent Application No. PCT/EP2012/002332, dated Nov. 8, 2012 (7 pages).
Invitation to file search results or a statement of non-availability pursuant to Rule 70b(1) EPC for European Application No. 11741685.9, dated Jul. 22, 2013 (1 page).
Knudsen et al., "Development and validation of a gene expression score that predicts response to fulvestrant in breast cancer patients," PLoS One. 9(2):e87415 (2014).
Kornmann et al., "Thymidylate synthase and dihydropyrimidine dehydrogenase mRNA expression levels: predictors for survival in colorectal cancer patients receiving adjuvant 5-fluorouracil," Clinical Cancer Res. 9(11):4116-24 (2003).
Li et al., "Intronic microRNA: discovery and biological implications," DNA Cell Biol. 26(4):195-207 (2007).
Li et al., "Selection of optimal oligonucleotide probes for microarrays using multiple criteria, global alignment and parameter estimation," Nucleic Acids Res. 33(19):6114-23 (2005).
Nakamura et al., "Search of a group of genes involved with sensitivity to anticancer agent Cisplatin (CDDP) using cDNA microarray," Chiba Med J. 80(2):88 (2004).
NCode™ Multi-Species miRNA Microarray Probe Set. Version 2.0 (Cat.# MIRMPS2-01 ), (2009). Received from http://www.invitrogen.comlsiteluslenlhomelProducts-and-ServiceslApplicationslepigenetics-noncoding-rna-researchlmiRNA-Profiling-ImiRNA-Probe-Set-Files.html (21 pages).
Nielsen et al., "Design of oligonucleotides for microarrays and perspectives for design of multi-transcriptome arrays," Nucleic Acids Res. 31(13):3491-6 (2003).
Notice of Reasons for Rejection for Japanese Application No. 2008-542865, dated May 28, 2015 (10 pages).
Notice of Reasons for Rejection for Japanese Application No. 2008-542865, dated Oct. 14, 2015 (8 pages).
Notice of Reasons for Rejection for Japanese Application No. 2014-029461, dated May 20, 2015 (14 pages).
Office Action for Canadian Application No. 2,631,236, dated Jan. 23, 2014 (2 pages).
Office Action for Chinese Application No. 200680052220.2, dated Dec. 15, 2010 (7 pages).
Office Action for Chinese Application No. 200680052220.2, dated Jan. 30, 2015 (8 pages).
Office Action in Chinese Patent Application No. 200680052220.2 dated Mar. 21, 2012 (with English Translation) (11 pages).
Office Action in Japanese Patent Application No. 2008-542865 dated Apr. 18, 2012 (with English Translation) (17 pages).
Pradervand et al., "Concordance among digital gene expression, microarrays, and qPCR when measuring differential expression of microRNAs," Biotechniques. 48(3):219-222 (2010).
Pre-Appeal Examination Report for Japanese Application No. 2008-542865, dated Mar. 27, 2014 (6 pages).
Questioning for Japanese Application No. 2008-542865, dated Aug. 11, 2014 (8 pages).
Reexamination Decision for Chinese Application No. 200680052220.2, dated Nov. 24, 2014 (11 pages).
Rouillard et al., "OligoArray 2.0: design of oligonucleotide probes for DNA microarrays using a thermodynamic approach," Nucleic Acids Res. 31(12):3057-62 (2003).
GenBank Accession No. HC040507.1: Sequence 486 from Patent EP2112235 (1 page).

(56) References Cited

OTHER PUBLICATIONS

The Japanese Journal of Urology, 94(2):159 (APP-105) (2003).
Van't Veer et al., "Gene expression profiling predicts clinical outcome of breast cancer," Nature. 415(6871):530-6 (2002).
Xu et al., "[Association of miRNAs expression profiles with prognosis and relapse in childhood acute lymphoblastic leukemia]," Zhonghua Xue Ye Xue Za Zhi. 32(3):178-81 (Abstract only) (2011).
Yang et al., "The role of microRNA in human lung squamous cell carcinoma," Cancer Genet Cytogenet. 200(2):127-33 (2010).
Yin, "Screening of laryngeal carcinoma multidrug resistance-associated genes and study on reversion by Chinese herbs" (Abstract Only), China Doctoral Dissertations Full-text Database, Division of medical and hygiene technology. 8:E072-85 (2010).
Zhang et al, "MicroRNA-650 targets ING4 to promote gastric cancer tumorigenicity," Biochem Biophys Res Commun. 395(2):275-280 (2010).
Paul et al., "Impact of miRNA deregulation on mRNA expression profiles in response to environmental toxicant, nonylphenol," Mol Cell Toxicol. 7:259-69 (2011).
Reid et al., "Circulating microRNAs: Association with disease and potential use as biomarkers," Crit Rev Oncol Hematol. 80(2):193-208 (2011).
Liang et al., "Characterization of microRNA expression profiles in normal human tissues," BMC Genomics. 8(166):1-20 (2007).
Elstrom et al., "Response to second-line therapy defines the potential for cure in patients with recurrent diffuse large B-cell lymphoma: implications for the development of novel therapeutic strategies," Clin Lymphoma Myeloma Leuk. 10(3):192-6 (2010).
Etter et al., "The combination of chemotherapy and intraperitoneal MegaFas Ligand improves treatment of ovarian carcinoma," Gynecol Oncol. 107(1):14-21 (2007).
Grimm et al., "Drugs interfering with apoptosis in breast cancer," Curr Pharm Des. 17(3):272-83 (2011).
Verbrugge et al., "Combining radiotherapy with APO010 in cancer treatment," Clin Cancer Res. 15(6):2031-8 (2009).
Abba et al., "Gene expression signature of estrogen receptor alpha status in breast cancer," BMC Genomics. 6:37 (2005) (13 pages).
Lee et al., "Cancer pharmacogenomics: powerful tools in cancer chemotherapy and drug development," Oncologist 10(2):104-11 (2005).
Michels, "The promises and challenges of epigenetic epidemiology," Exp Gerontol. 45(4):297-301 (2010).
Slonim, "From patterns to pathways: gene expression data analysis comes of age," Nat Genet. 32 Suppl:502-8 (2002).
Baker, "The central role of receiver operating characteristic (ROC) curves in evaluating tests for the early detection of cancer," J Natl Cancer Inst. 95(7):511-5 (2003).
Suresh et al., "Resistance/response molecular signature for oral tongue squamous cell carcinoma," Dis Markers. 32(1):51-64 (2012).
Affymetrix Expression Probeset Details, Details for HG-U133_PLUS_2:209083_AT, retrieved Nov. 27, 2018, <https://www.affymetrix.com/analysis/netaffx/fullrecord.affx?pk-HG-U133_PLUS_2:209083_AT>, (4 pages).
Fumagalli et al., "Oral vinorelbine and capecitabine plus bevacizumab in recurrent inflammatory breast cancer: gene profiling and response to treatment," Thirty-Third Annual CTRC-AACR San Antonio Breast Cancer Symposium, Dec. 8-12, San Antonio, TX. Cancer Res. 70(24 Suppl): Abstract nr P6-12-06 (2010) (4 pages).
Nair et al., "A simple practice guide for dose conversion between animals and human," J Basic Clin Pharm. 7(2):27-31 (2016).
López et al., Chapter 11: MicroRNAs in Lymphoma, *MicroRNAs in Cancer Translational Research*. W.C.S. Cho (ed.), 239-67 (2011).
Di Lisio, "MicroRNA expression in B-cell lymphomas," Doctoral Thesis, Facultad de Ciencias, Departamento de Biología Molecular, Universidad Autónoma de Madrid (2012) (223 pages).
Andresen et al., "Advanced strategies in liposomal cancer therapy: problems and prospects of active and tumor specific drug release," Prog Lipid Res. 44(1):68-97 (2005).
Benner et al., "Evolution, language and analogy in functional genomics," Trends Genet. 17(7):414-8 (2001).
Buhl et al., "Molecular prediction of adjuvant cisplatin efficacy in Non-Small Cell Lung Cancer (NSCLC)—validation in two independent cohorts," *PLoS One*, 13(3): e0194609 (2018) (12 pages).
Greaney et al., "APO010 kills haematological tumour cells while having no effect on the repopulating function of haematopoietic progenitor cells," Bone Marrow Transplant. 37(1):S105 (2006).
Ioannidis et al., "Comprehensive analysis of blood cells and plasma identifies tissue-specific miRNAs as potential novel circulating biomarkers in cattle," BMC Genomics. 19(1):243 (2018) (11 pages).
Østrem et al., "Secretory phospholipase $A_2$ responsive liposomes exhibit a potent anti-neoplastic effect in vitro, but induce unforeseen severe toxicity in vivo," J Control Release. 262: 212-221 (2017).
Pourhassan et al., "Revisiting the use of $sPLA_2$-sensitive liposomes in cancer therapy," J Control Release. 261:163-173 (2017).
Saito-Hisaminato et al., "Genome-wide profiling of gene expression in 29 normal human tissues with a cDNA microarray," DNA Res. 9(2):35-45 (2002).
Terwogt et al., "Phase I and pharmacokinetic study of SPI-77, a liposomal encapsulated dosage form of cisplatin," Cancer Chemother Pharmacol. 49(3):201-10 (2002).
Trosko et al., "Mechanism of up-regulated gap junctional intercellular communication during chemoprevention and chemotherapy of cancer," Mutat Res. 480-481: 219-29 (2001).
Veal et al., "A phase I study in paediatric patients to evaluate the safety and pharmacokinetics of SPI-77, a liposome encapsulated formulation of cisplatin," Br J Cancer. 84(8):1029-35 (2001).

\* cited by examiner

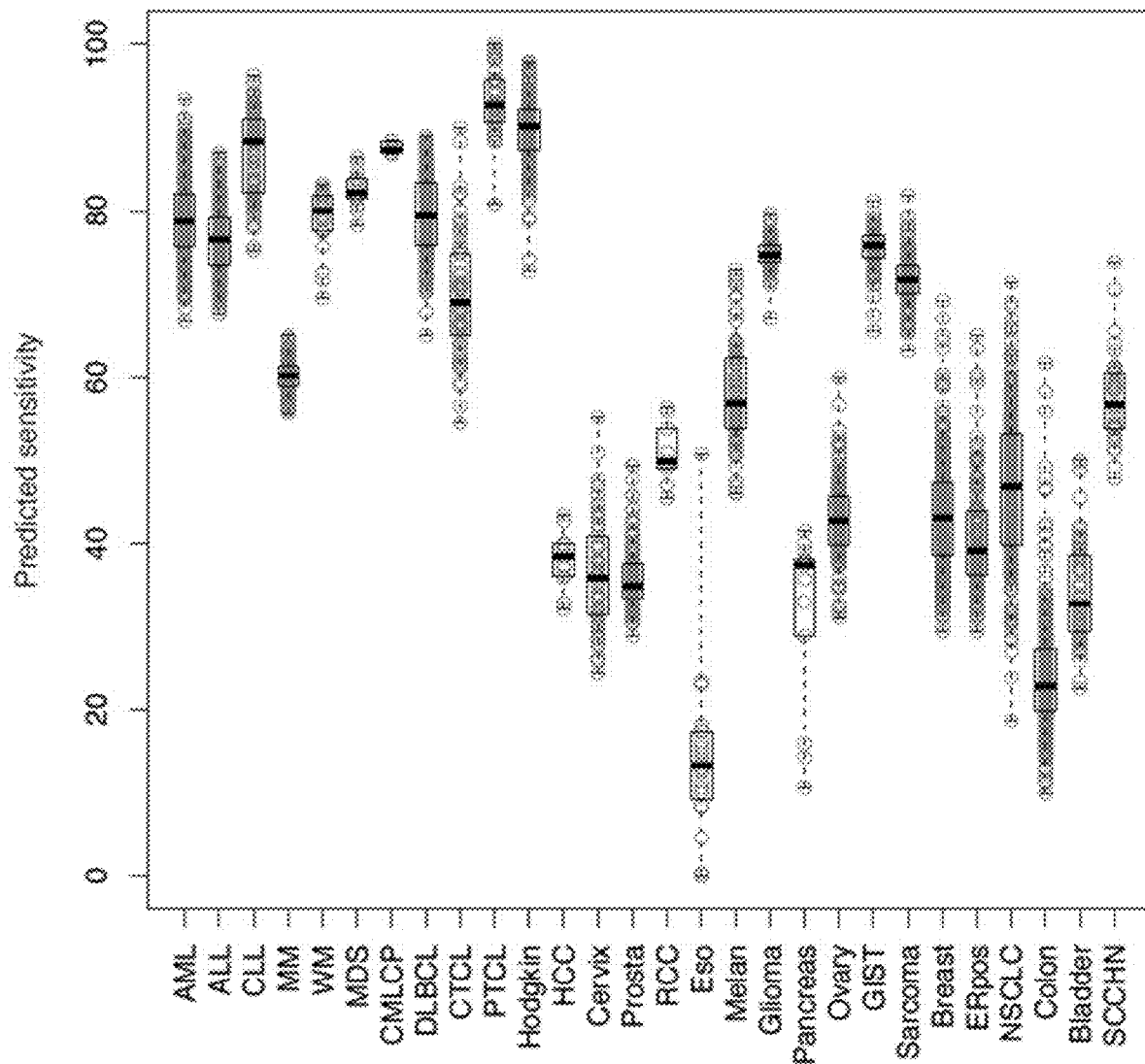

METHODS FOR PREDICTING DRUG RESPONSIVENESS IN CANCER PATIENTS

FIELD OF THE INVENTION

The invention pertains to methods of using biomarkers in cancer patients to predict responsiveness of the cancer patients to treatment.

BACKGROUND

DNA microarrays can be used to measure gene expression in tumor samples from patients and to facilitate diagnosis. Gene expression can reveal the presence of cancer in a patient in addition to the type, stage, and origin. Gene expression may even have a role in predicting the efficacy of cancer therapies. In recent decades, the National Cancer Institute (NCI) has tested cancer therapeutics for their effect in limiting the growth of 60 human cancer cell lines. The NCI has also measured gene expression in those 60 cancer cell lines using DNA microarrays. Various studies have explored the relationship between gene expression and therapeutic effect using the NCI datasets.

During cancer treatment, critical time is often lost due to a trial and error approach to finding an effective therapy. In addition, cancer cells often develop resistance to a previously effective therapy. In such situations, patient outcome would be greatly improved by early detection of such resistance to therapy.

Thus, there exists a need in the art for methods, devices, and kits that can predict the responsiveness of cancer patients to a medical treatment for cancer.

SUMMARY OF THE INVENTION

The invention features methods for detecting a level of one or more biomarkers (e.g., one, two, three, four, five, ten, twenty, or all of the biomarkers shown in Tables 1-4, such as COL5A2 (SEQ ID NO: 73 or 211)) in a patient having cancer, such as a patient having cancer (e.g., a human) that is resistant to one or more cancer therapies other than a secretory phospholipase $A_2$ (sPLA$_2$) hydrolysable, cisplatin-containing liposome (e.g., a patient having breast cancer that is resistant to one or more cancer therapies other than the liposome), and for determining responsiveness of a cancer patient (e.g., a patient having breast cancer) to treatment with the liposome. The invention also features methods of treating cancer in a patient (e.g., a patient having breast cancer or a treatment resistant form thereof) that include administering the sPLA$_2$ hydrolysable, cisplatin-containing liposome to the patient, in which the patient is or has been determined to be responsive to the liposome according to the diagnostic methods described herein.

Exemplary types of cancer that can be diagnosed or treated with the methods include, e.g., breast cancer, prostate cancer, ovarian cancer (e.g., ovarian adenocarcinoma or embryonal carcinoma), liver cancer (e.g., HCC or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. For example, the cancer may be a solid tumor (e.g., breast cancer) or a hematological cancer (e.g., cancer of the blood, such as lymphoma—(e.g., acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), or Hodgkin's lymphoma)).

A first aspect of the invention features a method for detecting a level of a biomarker (e.g., one, two, three, four, five, ten, twenty, or all of the biomarkers shown in Tables 1 and/or 2, such as COL5A2 (SEQ ID NO: 73 or 211)) in a patient having cancer (e.g., breast cancer), such as a patient having cancer that is resistant to one or more cancer therapies other than a sPLA$_2$ hydrolysable, cisplatin-containing liposome (e.g., a patient with breast cancer that is resistant to one or more cancer therapies other than the liposome). The method includes (a) contacting a sample (e.g., a tumor sample) from the patient including one or more nucleic acid molecules with a device (e.g., a microarray) including: i) one or more single-stranded nucleic acid molecules capable of specifically hybridizing with nucleotides of one or more biomarkers of sensitivity selected from those listed in Tables 1 and/or 3 or a complement thereof (e.g., COL5A2 (SEQ ID NO: 73 or 211)); and/or ii) one or more single-stranded nucleic acid molecules capable of specifically hybridizing with nucleotides of one or more biomarkers of resistance selected from those listed in Tables 2 and/or 4 or a complement thereof (e.g., SFN (SEQ ID NO: 96 or 324)); and (b) detecting a level of the one or more biomarkers of sensitivity or the complement thereof and/or the one or more biomarkers of resistance or the complement thereof in the sample by detecting hybridization between the one or more single-stranded nucleic acid molecules of the device and the one or more nucleic acid molecules of the sample (e.g., by performing microarray analysis or quantitative reverse transcriptase polymerase chain reaction (qRT-PCR)). The level of the biomarker(s) may be detected by determining the level of a messenger RNA (mRNA) corresponding to the biomarker(s; e.g., an mRNA expressed from COL5A2 (SEQ ID NO: 73 or 211)) or a complementary DNA (cDNA) thereof.

In the first aspect, the one or more cancer therapies may include surgery, radiation, or a therapeutic agent. In particular, the therapeutic agent may be selected from the group consisting of docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

A second aspect of the invention features a method of determining responsiveness of a patient having cancer (e.g., one of the cancers noted above, such as breast cancer) to the liposome. In particular, the patient may have a cancer that is resistant to one or more cancer therapies other than the liposome, such as breast cancer that is resistant to one or more cancer therapies other than the liposome. The method includes a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with nucleotides of one or more biomarkers of sensitivity selected from those listed in Tables 1 and/or 3 or a complement thereof (e.g., COL5A2 (SEQ ID NO: 73 or 211)); and/or ii) one or more single-stranded nucleic acid molecules capable of specifically hybridizing with nucleotides of one or more biomarkers of resistance selected from those listed in Tables 2 and/or 4 or a complement thereof (e.g., SFN (SEQ ID NO: 96 or 324)); and b) detecting a level of the one or more biomarkers of sensitivity or the complement thereof and/or the one or more biomarkers of resistance or the complement thereof by detecting hybridization between the single-stranded nucleic acid molecules of the device and the one or more nucleic acid molecules of the sample. The patient is determined to be responsive to the liposome if: i) the level of the biomarkers of sensitivity or the complement thereof (e.g., COL5A2 (SEQ ID NO: 73 or 211)) is substantially similar to the level of the biomarkers of sensitivity or the complement thereof in a cell (e.g., a cancer cell) or tissue (e.g., a tumor tissue) known to be sensitive to the liposome; and/or ii) the level of the biomarkers of resistance or the complement thereof (e.g., SFN (SEQ ID NO: 96 or 324)) is substantially dissimilar to the level of the biomarkers of resistance or the complement thereof in a cell (e.g., a cancer cell) or tissue (e.g., a tumor tissue) known to be resistant to the liposome.

The method of the second aspect can further include administering the liposome to the patient if: i) the level of the biomarkers of sensitivity or the complement thereof (e.g., COL5A2 (SEQ ID NO: 73 or 211)) is substantially similar to the level of the biomarkers of sensitivity or the complement thereof in a cell (e.g., a cancer cell) or tissue (e.g., a tumor tissue) known to be sensitive to the liposome; and/or ii) the level of the biomarkers of resistance or the complement thereof (e.g., SFN (SEQ ID NO: 96 OR 324)) is substantially dissimilar to the level of the biomarkers of resistance or the complement thereof in a cell (e.g., a cancer cell) or tissue (e.g., a tumor tissue) known to be resistant to the liposome. The method can further include administering one or more cancer therapies other than the liposome to the patient if: i) the level of the biomarkers of sensitivity or the complement thereof (e.g., COL5A2 (SEQ ID NO: 73 or 211)) is substantially dissimilar to the level of the biomarkers of sensitivity or the complement thereof in a cell (e.g., a cancer cell) or tissue (e.g., a tumor tissue) known to be sensitive to the liposome; and/or ii) the level of the biomarkers of resistance or the complement thereof (e.g., SFN (SEQ ID NO: 96 OR 324)) is substantially similar to the level of the biomarkers of resistance or the complement thereof in a cell (e.g., a cancer cell) or tissue (e.g., a tumor tissue) known to be resistant to the liposome.

In particular, the one or more of the cancer therapies includes surgery, radiation, or a therapeutic agent, such as docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

A third aspect of the invention features a method that includes contacting a sample from a patient having a cancer that is resistant to one or more cancer therapies (e.g., breast cancer), such as a patient having cancer that is resistant to one or more cancer therapies other than the liposome (e.g., a patient with breast cancer that is resistant to one or more cancer therapies other than the liposome) including one or more nucleic acid molecules, with a device including: i) one or more single-stranded nucleic acid molecules capable of specifically hybridizing with nucleotides of one or more biomarkers of sensitivity selected from the biomarkers of Tables 1 and 3 or a complement thereof (e.g., COL5A2 (SEQ ID NO: 73 or 211)), in which the biomarker of sensitivity is not C1QR1 (SEQ ID NO: 13), SLA (SEQ ID NO: 48), PTPN7 (SEQ ID NO: 77), CENTB1 (SEQ ID NO: 37), IFI16 (SEQ ID NO: 17 or 261), ARHGEF6 (SEQ ID NO: 36 or 294), CD3D (SEQ ID NO: 81), ARHGAP15 (SEQ ID NO: 30), HCLS1 (SEQ ID NO: 16 or 259), CD53 (SEQ ID NO: 282), PTPRCAP (SEQ ID NO: 8), or PTPRC (SEQ ID NO: 10, 18, 25, or 243); and/or ii) one or more single-stranded nucleic acid molecules capable of specifically hybridizing with nucleotides of one or more biomarkers of resistance selected from those listed in Tables 2 and/or 4 or a complement thereof (e.g., SFN (SEQ ID NO: 96 or 324)). The method also includes detecting a level of the one or more biomarkers of sensitivity or the complement thereof and/or the one or more biomarkers of resistance or the complement thereof in the sample by detecting hybridization between the one or more single-stranded nucleic acid molecules of the device and the one or more nucleic acid molecules of the sample (e.g., by performing microarray analysis or quantitative reverse transcriptase polymerase chain reaction (qRT-PCR)). The level of the biomarker(s) may be detected by determining the level of a messenger RNA (mRNA) corresponding to the biomarker(s; e.g., a mRNA expressed from COL5A2 (SEQ ID NO: 73 or 211)) or a complementary DNA (cDNA) thereof.

The method of the third aspect can further include that the patient is determined to be responsive to the liposome if: i) the level of the biomarkers of sensitivity or the complement thereof (e.g., COL5A2 (SEQ ID NO: 73 or 211)) is substantially similar to the level of the biomarkers of sensitivity or the complement thereof in a cell (e.g., a cancer cell) or tissue (e.g., a tumor tissue) known to be sensitive to the liposome; and/or ii) the level of the biomarkers of resistance or the complement thereof (e.g., SFN (SEQ ID NO: 96 or 324)) is substantially dissimilar to the level of the biomarkers of resistance or the complement thereof in a cell (e.g., a cancer cell) or tissue (e.g., a tumor tissue) known to be resistant to the liposome. The method can also include administering the liposome to the patient if: i) the level of the biomarkers of sensitivity or the complement thereof (e.g., COL5A2 (SEQ ID NO: 73 or 211)) is substantially similar to the level of the biomarkers of sensitivity or the complement thereof in a cell (e.g., a cancer cell) or tissue (e.g., a tumor tissue) known to be sensitive to the liposome; and/or ii) the level of the biomarkers of resistance or the complement thereof (e.g., SFN (SEQ ID NO: 96 or 324)) is substantially dissimilar to the level of the biomarkers of resistance or the complement thereof in a cell (e.g., a cancer cell) or tissue (e.g., a tumor tissue) known to be resistant to the liposome.

In any of the above aspects of the invention, the method can further include detecting a level of PLA2G2A (SEQ ID NO: 380) or a complement thereof in a tumor sample from the patient. In particular, the method can include contacting the tumor sample with one or more single-stranded nucleic acid molecules capable of specifically hybridizing with nucleotides of PLA2G2A (SEQ ID NO: 380) or a complement thereof and detecting a level of PLA2G2A or the complement thereof in the sample. Optionally, the detecting occurs by performing microarray analysis or qRT-PCR. The method can further include administering the liposome to the patient when a level of PLA2G2A is detected in the sample from the patient. The method can also further include detecting sPLA$_2$ protein in a tumor sample from the patient, such as by contacting the tumor sample with an anti-sPLA$_2$ antibody and detecting binding between the sPLA$_2$ protein and the anti-sPLA$_2$ antibody. Additionally, the method can include administering the liposome to the patient when the sPLA$_2$ protein is detected in the sample from the patient.

The invention also features a method of treating cancer in a patient in need thereof (e.g., one of the cancers noted above, such as breast cancer) that includes administering the liposome to the patient, in which the patient has been determined to be responsive to the liposome according to the method of the first or second aspect of the invention. In particular, the patient may have a cancer that is resistant to one or more cancer therapies other than the liposome (e.g., a patient with breast cancer that is resistant to one or more cancer therapies other than the liposome).

A fourth aspect of the invention features a method of treating a patient having cancer (e.g., one of the cancers noted above, such as breast cancer). In particular, the patient may have a cancer that is resistant to one or more cancer therapies other than the liposome (e.g., a patient with breast cancer that is resistant to one or more cancer therapies other than the liposome). The method includes a) contacting a sample (e.g., a tumor sample) from the patient including one or more nucleic acid molecules with a device (e.g., a microarray or a device for performing a qRT-PCR reaction) including: i) one or more single-stranded nucleic acid molecules capable of specifically hybridizing with nucleotides of one or more biomarkers of sensitivity selected from those listed in Tables 1 and/or 3 or a complement thereof (e.g., COL5A2 (SEQ ID NO: 73 or 211)); and/or ii) one or more single-stranded nucleic acid molecules capable of specifically hybridizing with nucleotides of one or more biomarkers of resistance selected from those listed in Tables 2 and/or 4 or a complement thereof (e.g., SFN (SEQ ID NO: 96 OR 324)); b) detecting a level of the one or more biomarkers of sensitivity or the complement thereof and/or the one or more biomarkers of resistance or the complement thereof by detecting hybridization between the one or more single-stranded nucleic acid molecules of the device and the one or more nucleic acid molecules of the sample; and c) administering the liposome to the patient if: i) the level of the biomarkers of sensitivity or the complement thereof is substantially similar to the level of the biomarkers of sensitivity or the complement thereof in a cell (e.g., a cancer cell) or tissue (e.g., a tumor tissue) known to be sensitive to the liposome; and/or ii) the level of the biomarkers of resistance or the complement thereof is substantially dissimilar to the level of the biomarkers of resistance or the complement thereof in a cell (e.g., a cancer cell) or tissue (e.g., a tumor tissue) known to be resistant to the liposome.

The method of the fourth aspect of the invention may further include administering one or more additional therapies (e.g., surgery, radiation, or a therapeutic agent) to the patient prior to, concurrently with, or after administration of the liposome. In particular, the therapeutic agent may be selected from the group consisting of docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab. The therapeutic agent can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically.

In the fourth aspect of the invention, the liposome may be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically. Preferably, the liposome is administered by intravenous injection. The liposome may be administered to the patient at a dose of about 60 mg/m$^2$ to about 120 mg/m$^2$ of cisplatin (e.g., 60-120 mg/m$^2$). In particular, the liposome is administered to the patient at a dose of about 60 mg/m$^2$ of cisplatin weekly, about 75 mg/m2 of cisplatin weekly, or about 90 mg/m$^2$ of cisplatin weekly. The method may include administering the liposome to the patient in a treatment regimen at least once per one, two, or three weeks or on day 1 and day 8 of a 3 week treatment regimen, in which the treatment regimen may optionally be repeated two to twenty times.

In the fourth aspect of the invention, the contacting step (a) and the detecting step (b) may occur prior to, concurrent, or after administration of the liposome to the patient. Additionally, the contacting step (a) and the detecting step (b) may occur two or more times, e.g., during treatment with the liposome. For example, the contacting step (a) and the measuring step (b) may occur two or more times to assess the continued sensitivity of the patient to the liposome.

In any of the above aspects of the invention, the cancer is selected from a solid tumor cancer and a hematological cancer. For example, the cancer is breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, and squamous cell carcinoma of the head and neck (SCCHN). In particular, the cancer is breast cancer, such as an estrogen receptor-positive (ERpos) breast cancer and/or a metastatic form of breast cancer.

In the second or fourth aspect of the invention, the cell (e.g., a cancer cell) or tissue (e.g., a tumor tissue) known to be sensitive to the liposome and/or the cell or tissue known to be resistant to the liposome is of the same type as a cell or tissue in the sample from the patient or from which the one or more nucleic acid molecules of the sample are derived. In particular, the cell (e.g., a cancer cell) or tissue (e.g., a tumor tissue) known to be sensitive to the liposome and/or the cell or tissue known to be resistant to the liposome is of the same type of cancer (e.g., breast cancer) as a cell or tissue in the sample from the patient or from which the one or more nucleic acid molecules of the sample are derived.

In any of the above aspects of the invention, the patient may exhibit cancer relapse (e.g., relapse of breast cancer), such as relapse after a first cancer treatment and prior to treatment with a therapeutic agent other than the liposome. Alternatively, the patient may have not been administered a treatment for cancer. Additionally, the patient may not have been determined to be resistant to the liposome.

In any of the above aspects of the invention, the device can include at least two, at least three, at least four, at least five, at least six, at least seven, at least eight, at least nine, at least ten, or more single-stranded nucleic acid molecules capable of specifically hybridizing with the nucleotides of one or more biomarkers of sensitivity selected from the biomarkers of Tables 1 and 3 or a complement thereof (e.g., COL5A2 (SEQ ID NO: 73 or 211); and/or at least two, at least three, at least four, at least five, at least six, at least seven, at least eight, at least nine, at least ten, or more single-stranded nucleic acid molecules capable of specifically hybridizing with the nucleotides of one or more biomarkers of resistance selected from the biomarkers of Tables 2 and 4 or a complement thereof (e.g., SFN (SEQ ID NO: 96 OR 324)). In particular, one or more of the single-stranded nucleic acid molecules of the device have a length in the range of 10 to 100 nucleotides in length (e.g., a length in the range of 20 to 60 nucleotides). For example, the one or more single-stranded nucleic acid molecules are labeled or immobilized on a solid substrate.

In any of the above aspects of the invention, the method may include converting the level of the one or more biomarkers of sensitivity or the complement thereof (e.g., one, two, three, four, five, ten, twenty, or all of the biomarkers shown in Tables 1 and 3, such as COL5A2 (SEQ ID NO: 73 or 211)) and/or the one or more biomarkers of resistance or the complement thereof (e.g., one, two, three, four, five, ten, twenty, or all of the biomarkers shown in Tables 2 and 4, such as SFN (SEQ ID NO: 96 OR 324)) into a mean score, in which the mean score indicates the responsiveness of the patient to the liposome. The method can further include subtracting the mean score for one or more of the biomarkers of resistance (e.g., one, two, three, four, five, ten, twenty, or all of the biomarkers shown in Tables 2 and 4, such as SFN (SEQ ID NO: 96 OR 324)) from the mean score for one or more of the biomarkers of sensitivity (e.g., one, two, three, four, five, ten, twenty, or all of the biomarkers shown in Tables 1 and 3, such as COL5A2 (SEQ ID NO: 73 or 211) to obtain a difference score, in which the difference score indicates the responsiveness of the patient to the liposome. In particular, the mean score and/or the difference score above a cutoff value indicates that the patient is responsive to the liposome, such as if the cutoff value is about 0.25, about 0.3, about 0.35, about 0.4, about 0.45, about 0.5, or greater.

In any of the above aspects of the invention, the device can be a microarray, such as a deoxyribonucleic acid (DNA)-based platform. Alternatively, the device can be for performing a qRT-PCR reaction (e.g., the device is used with a system for detecting the amplification product, for example, by fluorescence or by another method). The methods may also utilize both a microarray and a qRT-PCR. Thus, the level of the biomarkers of sensitivity (e.g., one, two, three, four, five, ten, twenty, or all of the biomarkers shown in Tables 1 and 3, such as COL5A2 (SEQ ID NO: 73 or 211) and/or the biomarkers of resistance (e.g., one, two, three, four, five, ten, twenty, or all of the biomarkers shown in Tables 2 and 4, such as SFN (SEQ ID NO: 96 OR 324)) can be measured using qRT-PCR. In particular, the level of the one or more biomarkers of sensitivity or the complement thereof (e.g., one, two, three, four, five, ten, twenty, or all of the biomarkers shown in Tables 1 and 3, such as COL5A2 (SEQ ID NO: 73 or 211)) and/or the one or more biomarkers of resistance or the complement thereof (e.g., one, two, three, four, five, ten, twenty, or all of the biomarkers shown in Tables 2 and 4, such as SFN (SEQ ID NO: 96 OR 324)) are detected by performing microarray analysis or qRT-PCR. Additionally, the nucleic acid molecules of the sample may include mRNA or a cDNA thereof.

In any of the above aspects of the invention, the biomarker of sensitivity may be selected from one or more of COL5A2 (SEQ ID NO: 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), EBI2 (SEQ ID NO: 9), ANP32E (SEQ ID NO: 11), SFPQ (SEQ ID NO: 12, 38 or 272), FNBP1 (SEQ ID NO: 14 or 28), CBFB (SEQ ID NO: 15), SFRS7 (SEQ ID NO: 19 or 54), and CAP350 (SEQ ID NO: 20 or 61). The biomarker of resistance may be selected from one or more of S SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), and LRP5 (SEQ ID NO: 112).

For example, the biomarkers of sensitivity may include COL5A2 (SEQ ID NO 73 or 211) and ITGA4 (SEQ ID NO: 1). The biomarkers of sensitivity may include COL5A2 (SEQ ID NO 73 or 211), ITGA4 (SEQ ID NO: 1), and MSN (SEQ ID NO: 2). The biomarkers of sensitivity may include COL5A2 (SEQ ID NO 73 or 211), ITGA4 (SEQ ID NO: 1), MSN (SEQ ID NO: 2), and FAM46A (SEQ ID NO: 3 OR 280). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), and ITGB2 (SEQ ID NO: 4). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), and DOCK2 (SEQ ID NO: 5 OR 223). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), and EVL (SEQ ID NO: 6). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), and SACS (SEQ ID NO: 7). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), SACS (SEQ ID NO: 7), and PTPRCAP (SEQ ID NO: 8). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), SACS (SEQ ID NO: 7), PTPRCAP (SEQ ID NO: 8), and EBI2 (SEQ ID NO: 9). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), SACS (SEQ ID NO: 7), PTPRCAP (SEQ ID NO: 8), EBI2 (SEQ ID NO: 9), and PTPRC (SEQ ID NO: 10, 18, 25, OR 243). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, OR 243), and ANP32E (SEQ ID NO: 11). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, OR 243), ANP32E (SEQ ID NO: 11), and SFPQ (SEQ ID NO: 12, 38 OR 272). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, OR 243), ANP32E (SEQ ID NO: 11), SFPQ (SEQ ID NO: 12, 38 OR 272), and C1QR1 (SEQ ID NO: 13). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 OR 280), ITGB2 (SEQ ID NO: 4), DOCK2 (SEQ ID NO: 5 OR 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, OR 243), ANP32E (SEQ ID NO: 11), SFPQ (SEQ ID NO: 12, 38 OR 272), C1QR1 (SEQ ID NO: 13), and FNBP1 (SEQ ID NO: 14 OR 28). The biomarkers of sensitivity may include COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), and CBFB (SEQ ID NO: 15). The biomarkers of sensitivity may include COL5A2 (SEQ ID NO: 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), EBI2 (SEQ ID NO: 9), ANP32E (SEQ ID NO: 11), SFPQ (SEQ ID NO: 12, 38 or 272), FNBP1 (SEQ ID NO: 14 or 28), CBFB (SEQ ID NO: 15), and SFRS7 (SEQ ID NO: 19 or 54). The biomarkers of sensitivity may include COL5A2 (SEQ ID NO: 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), EBI2 (SEQ ID NO: 9), ANP32E (SEQ ID NO: 11), SFPQ (SEQ ID NO: 12, 38 or 272), FNBP1 (SEQ ID NO: 14 or 28), CBFB (SEQ ID NO: 15), SFRS7 (SEQ ID NO: 19 or 54), and CAP350 (SEQ ID NO: 20 or 61).

For example, the biomarkers of resistance may include SFN (SEQ ID NO: 96 or 324) and LISCH7 (SEQ ID NO: 97). The biomarkers of resistance may include SFN (SEQ ID NO: 96 or 324), LISCH7 (SEQ ID NO: 97), and EPB41 L4B (SEQ ID NO: 98). The biomarkers of resistance may include SFN (SEQ ID NO: 96 or 324), LISCH7 (SEQ ID NO: 97), EPB41 L4B (SEQ ID NO: 98), and MST1R (SEQ ID NO: 99). The biomarkers of resistance may include SFN (SEQ ID NO: 96 or 324), LISCH7 (SEQ ID NO: 97), EPB41L4B (SEQ ID NO: 98), MST1R (SEQ ID NO: 99), and ITGB4

(SEQ ID NO: 100). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), and DBNDD2 (SEQ ID NO: 102 OR 365). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 OR 365), and TACSTD1 (SEQ ID NO: 104). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), and MISP (SEQ ID NO: 105). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), MISP (SEQ ID NO: 105), and KRT8 (SEQ ID NO: 106). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), MISP (SEQ ID NO: 105), KRT8 (SEQ ID NO: 106), and JUP (SEQ ID NO: 107 OR 400). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), MISP (SEQ ID NO: 105), KRT8 (SEQ ID NO: 106), JUP (SEQ ID NO: 107 OR 400), and KRT18 (SEQ ID NO: 108 OR 306. The biomarkers of resistance may include SFN (SEQ ID NO: 96 or 324), LISCH7 (SEQ ID NO: 97), EPB41L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), MISP (SEQ ID NO: 105), KRT8 (SEQ ID NO: 106), JUP (SEQ ID NO: 107 OR 400), KRT18 (SEQ ID NO: 108 OR 306, and FA2H (SEQ ID NO: 109). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), MISP (SEQ ID NO: 105), KRT8 (SEQ ID NO: 106), JUP (SEQ ID NO: 107 OR 400), KRT18 (SEQ ID NO: 108 OR 306, FA2H (SEQ ID NO: 109), and MGAT4B (SEQ ID NO: 110). The biomarkers of resistance may include SFN (SEQ ID NO: 96 or 324), LISCH7 (SEQ ID NO: 97), EPB41L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), MISP (SEQ ID NO: 105), KRT8 (SEQ ID NO: 106), JUP (SEQ ID NO: 107 OR 400), KRT18 (SEQ ID NO: 108 OR 306, FA2H (SEQ ID NO: 109), MGAT4B (SEQ ID NO: 110), and DSG2 (SEQ ID NO:111 OR 312). The biomarkers of resistance may include SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 OR 365), TACSTD1 (SEQ ID NO: 104), MISP (SEQ ID NO: 105), KRT8 (SEQ ID NO: 106), JUP (SEQ ID NO: 107 OR 400), KRT18 (SEQ ID NO: 108 OR 306, FA2H (SEQ ID NO: 109), MGAT4B (SEQ ID NO: 110), DSG2 (SEQ ID NO:111 OR 312), and LRP5 (SEQ ID NO: 112).

Definitions

As used herein, "a" or "an" means "at least one" or "one or more" unless otherwise indicated. In addition, the singular forms "a", "an", and "the" include plural referents unless the context clearly dictates otherwise.

As used herein, "about" refers to an amount±10% of the recited value.

By "biomarker" is meant a nucleic acid molecule (e.g., a mRNA or its complement, for example, a cDNA, or the nucleic acid sequence of all or a fragment of a gene) or a protein encoded by the nucleic acid molecule present in, or from, a cell or tissue. The level of the biomarker correlates to the responsiveness (e.g., sensitivity or resistance) of the cell or tissue (and thus, the patient in which the cell or tissue resides or the patient from which the cell or tissue was obtained) to a cancer treatment (e.g., secretory phospholipase $A_2$ ($sPLA_2$) hydrolysable liposome). In particular, biomarkers of sensitivity correspond to the nucleic acid molecules or the complements thereof (e.g., a mRNA or its complement or a cDNA thereof) shown in Tables 1 and 3, or the proteins encoded by the nucleic acid molecules, and biomarkers of resistance correspond to the nucleic acid molecules or the complements thereof (e.g., a mRNA or its complement or a cDNA thereof) shown in Tables 2 and 4, or the proteins encoded by the nucleic acid molecules.

The terms "cancer" and "cancerous" refer to or describe the physiological condition in mammals (e.g., humans) that is typically characterized by unregulated cell proliferation. Examples of cancer include, but are not limited to, breast cancer (e.g., medullary carcinoma or ER-positive breast cancer), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. The term cancer includes solid tumors (e.g., breast cancer) and hematological cancers (e.g., cancer of the blood, such as lymphoma (e.g., diffuse large B-cell lymphoma (DLBCL), cutaneous T-cell lymphoma (CTCL), peripheral T-cell lymphoma (PTCL), and Hodgkin's lymphoma)).

"Gene" as used herein indicates a coding or noncoding gene whose activity can be determined by measuring RNA (e.g., mRNA) transcribed from the gene, or its complement. Examples include protein coding genes, microRNAs, small nuclear RNAs and other RNAs with catalytic, regulatory or coding properties.

To "inhibit growth" as used herein means causing a reduction in cell growth (e.g., cancer cell growth, such as the NCI60 cancer cell lines) in vivo or in vitro by, e.g., 10%, 20%, 30%, 40%, 50%, 60%, 70%, 80%, 90%, 95%, or 99% or more, as evident by a reduction in the proliferation of cells exposed to a treatment (e.g., an sPLA$_2$ hydrolysable, cisplatin-containing liposome described herein), relative to the proliferation of cells in the absence of the treatment. Growth inhibition may be the result of a treatment (e.g., treatment with the sPLA$_2$ hydrolysable, cisplatin-containing liposome) that induces apoptosis in a cell, induces necrosis in a cell, slows cell cycle progression, disrupts cellular metabolism, induces cell lysis, or induces some other mechanism that reduces the proliferation of cells.

"Microarray" as used herein means a device employed by any method that quantifies one or more subject oligonucleotides, e.g., RNA, DNA, cDNA, or analogues thereof, at a time. For example, many DNA microarrays, including those made by Affymetrix (e.g., an Affymetrix HG-U133A or HG-U133_Plus_2 array), use several probes for determining the level of a single biomarker. The DNA microarray may contain oligonucleotide probes that may be, e.g., full-length cDNAs complementary to an RNA or cDNA fragments that hybridize to part of an RNA. The DNA microarray may also contain modified versions of DNA or RNA, such as locked nucleic acids or LNA. Exemplary RNAs include mRNA, miRNA, and miRNA precursors.

"NCI60" as used herein means a panel of 60 cancer cell lines from lung, colon, breast, ovarian, leukemia, renal, melanoma, prostate, and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COL0205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR IGROVI, OVAR SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

The terms "patient" and "subject," as used interchangeably herein, refer to any animal (e.g., a mammal, such as a human). A patient to be treated or tested for responsiveness to a treatment (e.g., treatment with an sPLA$_2$ hydrolysable, cisplatin-containing liposome) according to the methods described herein may be one who has been diagnosed with a cancer, such as those described herein, e.g., breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN). Diagnosis may be performed by any method or technique known in the art, such as x-ray, MRI, or biopsy, and may also be confirmed by a physician. To minimize exposure of a patient to drug treatments that may not be therapeutic, the patient may be determined to be either responsive or non-responsive to a cancer treatment, such as an sPLA$_2$ hydrolysable, cisplatin-containing liposome, according to the methods described herein prior to treatment.

As used herein, the term "percent (%) sequence identity" refers to the percentage of nucleic acid residues of a candidate sequence, e.g., a probe or primer of the invention, that are identical to the nucleic acid residues of a reference sequence, e.g., a biomarker sequence of the invention, after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using computer software, such as BLAST, BLAST-2, BLAST-P, BLAST-N, BLAST-X, WU-BLAST-2, ALIGN, ALIGN-2, CLUSTAL, Megalign (DNASTAR). In addition, those skilled in the art can determine appropriate parameters for measuring alignment, including any algorithms needed to achieve optimal alignment over the length of the sequences being compared.

"Resistant" or "resistance" as used herein means that a cell (e.g., a cancer cell), a tissue containing the cell (e.g., a tumor), or a patient containing the cell or tissue having cancer (e.g., a human having cancer) is non-responsive to treatment with an anti-cancer agent (e.g., an sPLA$_2$ hydrolysable, cisplatin-containing liposome). In particular, the treatment reduces the growth of a resistant cell (e.g., the cancer cell) in vitro by less than about 40%, 30%, 20%, 10%, 5%, 1%, or less, relative to the growth of a less resistant cell not exposed to the treatment. Resistance to treatment may be determined by a cell proliferation assay, e.g., a cell-based assay, which measures the growth of treated cells as a function of the absorbance of the cells of an incident light beam, such as the NCI60 assays described herein. In this assay, greater absorbance indicates greater cell growth, and thus, resistance to the treatment.

A cancer patient (e.g., a patient having breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN)) may also have resistance to a cancer therapy other than an sPLA$_2$ hydrolysable, cisplatin-containing liposome, such as surgery, radiation, or a therapeutic agent (e.g., docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methyl-prednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab).

The terms "responsive" and "responsiveness," as used herein, refer to the likelihood that a cancer treatment (e.g., treatment with an sPLA$_2$ hydrolysable, cisplatin-containing liposome) has (e.g., induces) a desired effect in a cell (e.g., a cancer cell), a tissue (e.g., a tumor), or a patient having cancer (e.g., a human having cancer). For example, the desired effect can include inhibition of the growth of a cancer cell in vitro by more than 10%, 20%, 30%, 40%, 50%, 60%, 70%, 80%, 90%, or 100% relative to the growth of a cancer cell not exposed to the treatment. The desired effect can also include reduction in tumor mass by, e.g., about 10%, 20%, 30%, 40%, 50%, 60%, 70%, 80%, 90%, or 100%. Responsiveness to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity to the treatment. A greater reduction in growth indicates more sensitivity to the treatment. In particular, "responsiveness" is a measure of the sensitivity or resistance of a patient to a treatment for cancer (e.g., an sPLA$_2$ hydrolysable, cisplatin-containing liposome).

The term "sample," as used herein, refers to any specimen (such as cells, tissue (e.g., a tissue sample obtained by biopsy), blood, serum, plasma, urine, cerebrospinal fluid, or pancreatic fluid) taken from a subject. Preferably, the sample is taken from a portion of the body affected by a cancer (e.g., a biopsy of the cancer tissue, such as breast cancer tissue). Biopsy may involve fine needle aspiration biopsy, core needle biopsy (e.g., stereotactic core needle biopsy, vacuum-assisted core biopsy, or magnetic resonance imaging (MRI) guided biopsy), or surgical biopsy (e.g., incisional biopsy or excisional biopsy). The sample may undergo additional purification and processing, for example, to remove cell debris and other unwanted molecules. Additional processing may further involve producing cDNA molecules corresponding to nucleic acid molecules (e.g., mRNA) in the sample and/or amplification of the nucleic acid molecules, e.g., using PCR, such as RT-PCR. The standard methods of sample purification, such as removal of unwanted molecules, are known in the art.

The terms "secretory phospholipase A$_2$ (sPLA$_2$) hydrolyzable, cisplatin-containing liposome," "sPLA$_2$ hydrolysable, cisplatin-containing liposome," and "the liposome" as used herein refer to an antitumor agent that is a liposomal formulation of cisplatin. The sPLA$_2$ hydrolysable, cisplatin-containing liposome (e.g., LiPlaCis®, LiPlasome Pharma) is formulated to release an encapsulated drug (e.g., cisplatin) from the core of a hydrophobic layer into tumor tissue. Since sPLA$_2$ protein is associated with tumor tissue, sPLA$_2$ hydrolysable liposomes may be used to preferentially deliver encapsulated drugs (e.g., cisplatin) to the tumor tissue. An sPLA$_2$ hydrolysable, cisplatin-containing liposome is described in, e.g., U.S. Patent Application Publication No. 2012/0177726 and de Jonge et al. (*Eur J Cancer.* 46(16): 3016-21, 2010), each of which is hereby incorporated by reference.

"Sensitive" and "sensitivity" as used herein refer to a cell (e.g., a cancer cell), a tissue containing the cell (e.g., a tumor), or a patient containing the cell or tissue having cancer (e.g., a human having cancer) that is responsive to treatment, such as an anti-cancer agent (e.g., an sPLA$_2$ hydrolysable, cisplatin-containing liposome) or radiation treatment. In particular, the treatment inhibits the growth of the cell (e.g., the cancer cell) in vitro by about 70%, 80%, 90%, 95%, 99% or 100% relative to the growth of a cell not exposed to the treatment. Sensitivity to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity to the treatment.

The term "specific hybridization" as used herein refers to when complementary nucleic acid sequences form a stable duplex under high stringency conditions, such as high hybridization temperature and low salt in hybridization buffers, which permit only hybridization between nucleic acid sequences that are highly similar. Nucleic acids are referred to as "complementary" that contain nucleotides or nucleotide homologues that can form hydrogen bonds according to Watson-Crick base-pairing rules (e.g., G with C, A with T or A with U) or other hydrogen bonding motifs such as for example diaminopurine with T, 5-methyl C with G, 2-thiothymidine with A, inosine with C, pseudoisocytosine with G, etc. Anti-sense RNA may be complementary to other oligonucleotides, e.g., mRNA.

"Treatment," "medical treatment," to "treat," and "therapy," as used interchangeably herein, refer to administering or exposing a patient having cancer (e.g., a human) to an anti-cancer agent (e.g., a drug such as an sPLA$_2$ hydrolysable, cisplatin-containing liposome, a protein, an antibody, a nucleic acid, a chemotherapeutic agent, or a radioactive agent), or to some other form of medical intervention used to treat or prevent a disease, disorder, or condition (e.g., surgery, cryotherapy, radiation therapy, or combinations thereof). In particular, a medical treatment can be or can include administration of an sPLA$_2$ hydrolysable, cisplatin-containing liposome. For example, the treatment may be of a cancer, such as a solid tumor or a hematological cancer. Examples of cancer include, e.g., breast cancer (e.g., medullary carcinoma or an ER-positive breast cancer), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. Radiation therapy includes the administration of a radioactive agent to a patient or exposure of a patient to radiation. The radiation may be generated from sources, such as particle accelerators and related medical devices or agents that emit, e.g., X-radiation, gamma radiation, or electron (Beta radiation) beams. A treatment may be or further include surgery, e.g., to remove a tumor from a subject or living organism.

Other features and advantages of the invention will be apparent from the following Detailed Description, the drawings, and the claims.

BRIEF DESCRIPTION OF THE DRAWINGS

FIG. 1 is a graph grouping predicted sensitivity to a secretory phospholipase $A_2$ (sPLA$_2$) hydrolysable, cisplatin-containing liposome by cancer type. Each gray circle represents the predicted liposome sensitivity of one patient calculated as the difference between the mean of the levels of the biomarkers of sensitivity (e.g., Tables 1 and/or 3) and the mean of the levels of the biomarkers of resistance for the patient (e.g., Tables 2 and/or 4). Patients are grouped according to cancer type. The median predicted sensitivity (black bar) for a cancer type is related to the relative response rate for that cancer type. The predictions are used for relative comparisons to compare cancer types and cannot be used for absolute predictions of response rate for a given cancer type. The predictions are normalized to a scale of 0 to 100 for all 3,522 patients.

DETAILED DESCRIPTION OF THE INVENTION

I have discovered that the levels of one or more of the biomarkers shown in Tables 1-4 (e.g., as single biomarkers or combinations of biomarkers) may be detected in a patient having cancer and used to predict the responsiveness of the patient to a secretory phospholipase $A_2$ (sPLA$_2$) hydrolysable, cisplatin-containing liposome. These patients may already be determined to be resistant to a therapy other than an sPLA$_2$ hydrolysable, cisplatin-containing liposome, such as docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

A device, such as a microarray, with one or more single-stranded oligonucleotide probes that have substantial identity (e.g., at least 85%, 90%, 95%, 99%, or 100% sequence identity) to a sequence that is complementary or identical to the nucleic acid sequence of one or more biomarkers shown in Tables 1-4 can be used according to the methods described herein to assess the responsiveness of a cancer patient to treatment with an sPLA$_2$ hydrolysable, cisplatin-containing liposome. For example, the probes can be used to detect one or more (e.g., two, three, four, five, ten, twenty, or all) of the biomarkers of sensitivity listed in Tables 1 and 3, such as COL5A2 (SEQ ID NO 73 or 211), in a sample (e.g., a tumor sample) from a patient having cancer (e.g., breast cancer). Additionally, the probes can be used to detect one or more (e.g., two, three, four, five, ten, twenty, or all) of the biomarkers of resistance listed in Tables 2 and 4, such as SFN (SEQ ID NO: 96 or 324), in a sample (e.g., a tumor sample) from a patient having cancer (e.g., breast cancer).

Accordingly, the invention features individual biomarkers (e.g., COL5A2 (SEQ ID NO 73 or 211) or SFN (SEQ ID NO: 96 or 324)) and sets of biomarkers shown in Tables 1-4 that can be used to determine the responsiveness of a cancer patient to an sPLA$_2$ hydrolysable, cisplatin-containing liposome at various stages of disease progression (e.g., patients diagnosed with cancer or patients after cancer recurrence) and at different times during the treatment process (e.g., prior to administration of any cancer treatment, after administration of one or more cancer treatments other than an sPLA$_2$ hydrolysable, cisplatin-containing liposome, prior to administration of the liposome, or during administration of the liposome). The individual biomarkers (e.g., COL5A2 (SEQ ID NO 73 or 211) or SFN (SEQ ID NO: 96 or 324)) and sets of biomarkers shown in Tables 1-4 can be used in combination with a level of PLA2G2A (SEQ ID NO: 380) or sPLA$_2$ protein to determine the responsiveness of a cancer patient to an sPLA$_2$ hydrolysable, cisplatin-containing liposome. Additionally, the methods can be used to determine responsiveness of a cancer patient to an sPLA$_2$ hydrolysable, cisplatin-containing liposome that is resistant to one or more cancer therapies other than the liposome, such as docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methyl-prednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

In particular, the invention provides methods for determining whether a patient may be responsive to an sPLA$_2$ hydrolysable, cisplatin-containing liposome by, e.g., detecting the level (e.g., mRNA or a protein produced therefrom) of one or more of the biomarkers shown in Tables 1-4 (e.g., COL5A2 (SEQ ID NO 73 or 211)) in a biological sample (e.g., a tumor biopsy) obtained from the subject using a device (e.g., a microarray or a protein array). The level of one or more of the biomarkers of sensitivity may then be compared to the level of the biomarkers in a cell or tissue known to be sensitive or resistant to the liposome to determine the patient's responsiveness to the liposome. The patient is determined to be responsive to the liposome if the level of the one or more of the biomarkers of sensitivity (e.g., one or more of COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38, or 272), C1QR1 (SEQ ID NO: 13), FNBP1 (SEQ ID NO: 14 or 28), CBFB (SEQ ID NO: 15), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), and LAT2 (SEQ ID NO: 220)) is substantially similar to the level of the biomarkers of sensitivity in a cell or tissue known to be sensitive to the liposome (e.g., from a patient sensitive to the liposome). The patient is also determined to be responsive to the liposome if the level of one or more of the biomarkers of resistance (e.g., one or more of SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), and IFI27 (SEQ ID NO: 321)) is substantially dissimilar to the level of the biomarkers of resistance in a cell or tissue known to be resistant to the liposome (e.g., from a patient resistant to the liposome). Additionally, the patient is determined to be responsive to the liposome if a level of PLA2G2A or sPLA$_2$ is detected in a tumor sample from the patient and the level of the biomarkers of sensitivity (e.g., COL5A2 (SEQ ID NO 73 or 211)) is substantially similar to the level of the biomarkers of sensitivity in a tissue known to be sensitive to the liposome and/or the level of the biomarkers of resistance is substantially dissimilar to the level of the biomarkers of resistance (e.g., SFN (SEQ ID NO: 96 or 324)) in a tissue known to be resistant to the liposome.

The invention also features methods of treating a patient having cancer, such as a patient having a cancer that is resistant to one or more cancer therapies other than an sPLA$_2$ hydrolysable, cisplatin-containing liposome, by detecting the levels of one or more of the biomarkers shown in Tables 1-4 (e.g., COL5A2 (SEQ ID NO: 73 or 211) in a sample (e.g., a tumor sample) from the patient, and then administering the liposome based on the levels of the biomarkers. In particular, a patient having cancer may be administered the liposome if the level of one or more biomarkers of sensitivity is substantially similar to the level of the biomarkers of sensitivity in a cell or tissue known to be sensitive to the liposome. Additionally, a patient having cancer may be administered the liposome if the level of one or more biomarkers of resistance is substantially dissimilar to the level of the biomarkers of resistance in a cell or tissue known to be resistant to the liposome. Thus, the methods can be used to treat cancer patients predicted to be responsive to the liposome, such as patients having, e.g., breast cancer (e.g., a metastatic form of breast cancer), prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, estrogen receptor-positive (ERpos) breast cancer, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), and Hodgkin's lymphoma. Alternatively, a patient having cancer may not be administered the liposome if the level of one or more biomarkers of sensitivity is substantially dissimilar to the level of the biomarkers of sensitivity in a cell or tissue known to be sensitive to the liposome. Likewise, a patient having cancer may not be administered the liposome if the level of one or more biomarkers of resistance is substantially similar to the level of the biomarkers of resistance in a cell or tissue known to be resistant to the liposome. Additionally, the patient may not be administered the liposome if a level of PLA2G2A or the protein product thereof (sPLA$_2$) is not detected in a tumor sample from the patient in combination with the methods.

Methods are described herein for identifying biomarkers of drug responsiveness, detecting levels of one or more biomarkers of sensitivity and one or more biomarkers of resistance in cancer patients, determining the responsiveness of a cancer patient to an sPLA$_2$ hydrolysable, cisplatin-containing liposome, and treating cancer patients with the liposome. Also described are devices and kits for use in these methods.

Methods for Identifying Biomarkers of Drug Responsiveness

The invention features methods for identifying biomarkers (e.g., one or more of the biomarkers of Tables 1-4) for determining the responsiveness of a cancer patient to a cancer treatment, such as an sPLA$_2$ hydrolysable, cisplatin-containing liposome. Such methods can involve, for example, an algorithm based on growth inhibition values (GI50) of cell lines (e.g., NCI60 cell lines) subjected to treatment with the liposome, followed by measurement of gene expression (e.g., using a microarray (e.g., an Affymetrix HG-U133A or HG-U133_Plus_2 array)).

Methodology of the In Vitro Cancer Growth Inhibition Screen

The human tumor cell lines of the cancer screening panel may be grown in RPMI 1640 medium containing 5% fetal bovine serum and 2 mM L-glutamine. Cells may be inoculated into 96 well microtiter plates in 100 µL at plating densities ranging from 5,000 to 40,000 cells/well depending on the doubling time of individual cell lines. After cell inoculation, the microtiter plates may be incubated at 37° C., 5% CO2, 95% air and 100% relative humidity for 24 hours prior to addition of experimental agent (e.g., an sPLA$_2$ hydrolysable, cisplatin-containing liposome).

After 24 hours, two plates of each cell line may be fixed in situ with TCA, to represent a measurement of the cell population for each cell line at the time of agent addition (Tz). Experimental agents may be solubilized in dimethyl sulfoxide at 400-fold the desired final maximum test concentration and stored frozen prior to use. At the time of agent (e.g., an sPLA$_2$ hydrolysable, cisplatin-containing liposome) addition, an aliquot of frozen concentrate may be thawed and diluted to twice the desired final maximum test concentration with complete medium containing 50 µg/ml Gentamicin. A total of four additional 10-fold or ½ log serial dilutions are made to provide a total of five concentrations plus control. Aliquots of 100 µl of these different agent dilutions are added to the appropriate microtiter wells already containing 100 µl of medium, resulting in the required final agent concentrations.

Following agent (e.g., a sPLA$_2$ hydrolysable, cisplatin-containing liposome) addition, the plates may be incubated for an additional 48 h at 37° C., 5% CO2, 95% air, and 100% relative humidity. For adherent cells, the assay may be terminated by the addition of cold TCA. Cells may be fixed in situ by the gentle addition of 50 µl of cold 50% (w/v) TCA (final concentration, 10% TCA) and incubated for 60 minutes at 4° C. The supernatant may be discarded, and the plates may be washed five times with tap water and air-dried. Sulforhodamine B (SRB) solution (100 µl) at 0.4% (w/v) in 1% acetic acid may be added to each well, and the plates may be incubated for 10 minutes at room temperature. After staining, unbound dye may be removed by washing five times with 1% acetic acid and the plates may be air-dried. Bound stain may be subsequently solubilized with 10 mM trizma base, and the absorbance may be read on an automated plate reader at a wavelength of 515 nm. For suspension cells, the methodology may be the same, except that the assay may be terminated by fixing settled cells at the bottom of the wells by gently adding 50 µl of 80% TCA (final concentration, 16% TCA). Using the seven absorbance measurements [time zero, (Tz), control growth, (C), and test growth in the presence of agent (e.g., the liposome) at the five concentration levels (Ti)], the percentage growth may be calculated at each of the agent concentration levels. Percentage growth inhibition may be calculated as:

$[(Ti-Tz)/(C-Tz)] \times 100$ for concentrations for which $Ti >/= Tz$ $[(Ti-Tz)/Tz] \times 100$ for concentrations for which $Ti < Tz$ Three dose response parameters may be calculated for each experimental agent (e.g., the liposome). Growth inhibition of 50% (GI50) is calculated from $[(Ti-Tz)/(C-Tz)] \times 100 = 50$, which is the agent (e.g., an sPLA$_2$ hydrolysable, cisplatin-containing liposome) concentration resulting in a 50% reduction in the net protein increase (as measured by SRB staining) in control cells during incubation with the test agent. The agent concentration resulting in total growth inhibition (TGI) is calculated from Ti=Tz. The LC50 (concentration of the agent, such as an sPLA$_2$ hydrolysable, cisplatin-containing liposome, resulting in a 50% reduction in the measured protein at the end of the compound treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

Gene Expression and Growth Inhibition Analysis

The gene expression measurements of NCI60 cancer cell lines can be obtained from a publically available database (e.g., the National Cancer Institute and the Massachusetts Institute of Technology). Each dataset can be normalized so that sample expression measured by different chips can be compared. The preferred method of normalization is the logit transformation, which may be performed for each gene y on each chip, as follows:

logit(y)=log [(y−background)/(saturation−y)], where background is calculated as the minimum intensity measured on the chip minus 0.1% of the signal intensity range: min−0.001*(max−min), and saturation is calculated as the maximum intensity measured on the chip plus 0.1% of the signal intensity range: max+0.001*(max−min). The resulting logit transformed data may then be z-transformed to mean zero and standard deviation 1.

Next, gene expression can be correlated to cancer cell growth inhibition. Growth inhibition data (GI50) of the NCI60 cell lines in the presence of a cancer treatment, such as an sPLA$_2$ hydrolysable, cisplatin-containing liposome, can be obtained from the NCI. The correlation between the logit-transformed expression level of each gene in each cell line and the logarithm of G150 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given treatment (e.g., an sPLA$_2$ hydrolysable, cisplatin-containing liposome) may be correlated to gene expression levels of the patient. Since a plurality of measurements may be available for a single gene, the most accurate determination of correlation coefficient can be, e.g., the median of the correlation coefficients calculated for all probes measuring expression of the same gene.

For example, the median correlation coefficient of gene expression measured on a probe to growth inhibition or patient sensitivity to an sPLA$_2$ hydrolysable, cisplatin-containing liposome can be calculated for all genes of interest. Genes that have a median correlation above about 0.25 (e.g., above 0.25, 0.26, 0.27, 0.28, 0.29, 0.30, 0.31, 0.32, 0.33, 0.34, 0.35, 0.36, 0.37, 0.38, 0.39, 0.40, or higher (e.g., 0.3 or higher)), can be used as biomarkers of sensitivity for assessing responsiveness of a cancer patient (e.g., a patient having cancer that is resistant to one or more cancer therapies other than the liposome) to the liposome. Likewise, genes that have a median correlation below about −0.25 (e.g., below −0.25, −0.26, −0.27, −0.28, −0.29, −0.30, −0.31, −0.32, −0.33, −0.34, −0.35, −0.36, −0.37, −0.38, −0.39, −0.40, or lower (e.g., −0.3 or lower)), can be used as biomarkers of resistance for assessing responsiveness of a cancer patient (e.g., a patient having cancer that is resistant to one or more cancer therapies other than the liposome) to the liposome. Preferably, the correlation coefficient of a biomarker of sensitivity will exceed 0.25, while the correlation coefficient of a biomarker of resistance will be less than −0.25. The result is a list of biomarker genes that correlate to sensitivity or resistance to the liposome, as shown in Tables 1 and 3 and Tables 2 and 4, respectively.

Cancer Types

The methods, devices, and kits of the invention can be used for prognosing, monitoring, treating, and/or reducing cancer in a subject suffering from, diagnosed with, or susceptible to cancer. Non-limiting examples of cancers that can be prognosed, monitored, treated (e.g., by administering an sPLA$_2$ hydrolysable, cisplatin-containing liposome), or reduced using the methods include hematological and solid tumors. In particular, cancers include, e.g., breast cancer (e.g., an estrogen receptor-positive (ERpos) breast cancer or a metastatic form of breast cancer), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system.

In particular, the methods are useful for prognosing, monitoring, treating, or preventing, e.g., breast cancer (e.g., an ERpos breast cancer or a metastatic form of breast cancer), prostate cancer, ovarian cancer, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), colon cancer, bladder cancer, squamous cell carcinoma of the head and neck (SCCHN), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), and Hodgkin's lymphoma. For example, the cancer can be breast cancer, such as Stage 0, Stage I, Stage II, Stage III, or Stage IV breast cancer. In particular, the cancer may be breast cancer that is resistant to one or more cancer therapies other than an sPLA$_2$ hydrolysable, cisplatin-containing liposome, such as doxorubicin, cyclophosphamide, fluorouracil (5-FU), methotrexate, docetaxel, epirubicin, paclitaxel, docetaxel, carboplatin, trastuzumab, vinorelbine, vinorelbin, radiation, and/or surgery. For instance, the breast cancer is medullary carcinoma. The breast cancer may also be, e.g., a metastatic form of breast cancer.

Methods for Detecting Biomarker Levels in Cancer Patients

A cancer patient can be assessed for sensitivity or resistance to an sPLA$_2$ hydrolysable, cisplatin-containing liposome by detecting a level of a biomarker (e.g., one or more of the biomarkers of Tables 1-4) in a biological sample obtained from the cancer patient (e.g., a patient having cancer that is resistant to one or more cancer therapies other than the liposome). Additionally, the detection of sPLA$_2$ and/or a level of PLA2G2A (SEQ ID NO: 380) in a tumor sample from the cancer patient can be used in combination with the level of the biomarker (e.g., one or more of the biomarkers of Tables 1-4) to determine patient sensitivity or resistance to the liposome. The biological sample can include, for example, cells, tissue (e.g., a tissue sample obtained by biopsy), blood, serum, plasma, urine, sputum, cerebrospinal fluid, lymph tissue or fluid, or pancreatic fluid. For example, the biological sample can be fresh frozen or formalin-fixed paraffin embedded (FFPE) tissue obtained from the subject, such as a tumor sample (e.g., a biopsy) from the tissue of interest (e.g., prostate, ovarian, lung, lymph nodes, thymus, spleen, bone marrow, breast, colorectal, pancreatic, cervical, bladder, gastrointestinal, head, or neck tissue).

RNA Extraction and Measurement of Biomarker Levels

Cell samples or tissue samples may be snap frozen in liquid nitrogen until processing. RNA may be extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. or a compatible apparatus, e.g., the GCS3000Dx GeneChip® System from Affymetrix Inc., using the manufacturer's instructions. The resulting biomarker level measurements may be further analyzed as described herein. The procedures described can be implemented using, e.g., R software available from R-Project (www.r-project.org) and supplemented with packages available from Bioconductor (www.bioconductor.org).

The level of one or more of the biomarkers shown in Tables 1-4 (e.g., COL5A2 (SEQ ID NO: 73 or 211)) may be measured in a biological sample (e.g., a tumor sample) obtained from the cancer patient (e.g., a patient having any of the cancer types described herein, such as a patient having cancer that is resistant to one or more cancer therapies other than an sPLA$_2$ hydrolysable, cisplatin-containing liposome) using, e.g., polymerase chain reaction (PCR), reverse transcriptase PCR (RT-PCR), quantitative real-time PCR (qRT-PCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies (e.g., those described in U.S. Patent Application Nos. US 2011/0201515, US 2011/0229888, and US 2013/0017971, each of which is incorporated by reference in its entirety), proteomic techniques (e.g., mass spectrometry or protein arrays), and combinations thereof. In combination with the level of these biomarkers, the level of PLA2G2A (SEQ ID NO: 380) or the gene product thereof (sPLA$_2$) may be detected using, e.g., PCR, RT-PCR, qRT-PCR, an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies, an anti-sPLA$_2$ antibody, proteomic techniques (e.g., mass spectrometry or protein arrays), and combinations thereof.

Devices

Devices of the invention can be used for detecting a level of one or more biomarkers shown in Tables 1-4 and/or a level of PLA2G2A (SEQ ID NO: 380). The device may include at least one (or one type of) single-stranded nucleic acid (e.g., a probe) having at least 85% sequence identity (e.g., 85%, 90%, 95%, 97%, 98%, 99%, or 100% sequence identity) to a nucleic acid sequence that is complementary or identical to at least 5 (e.g., at least 10, at least 15, at least 20, or more) consecutive nucleotides of one or more biomarkers shown in Tables 1-4 (e.g., COL5A2 (SEQ ID NO 73 or 211) or SFN (SEQ ID NO: 96 or 324)) and/or PLA2G2A (SEQ ID NO: 380), in which the at least one single-stranded nucleic acid is sufficient for the detection of the level of the one or more biomarkers. The device may be used to detect the level of a given biomarker by specific hybridization between the single-stranded nucleic acid and the biomarker (e.g., an mRNA, genomic DNA, or non-coding RNA), a nucleic acid of the biomarker (e.g., an mRNA), or a complementary nucleic acid thereof. The device may be or include a microarray. The device may also include or be used with reagents and materials for next generation sequence (e.g., sequencing by synthesis). The device may also include or be used with NanoString reagents and at least one nCounter cartridge. The device may be or include a protein array, which contains one or more protein binding moieties (e.g., proteins, antibodies, nucleic acids, aptamers, affibodies, lipids, phospholipids, small molecules, labeled variants of any of the above, and any other moieties useful for protein detection as well known in the art) capable of detectably binding to the polypeptide product(s) of one or more biomarkers shown in Tables 1-4 and/or PLA2G2A (SEQ ID NO: 380). The device may also be a cartridge for measuring an amplification product resulting from hybridization between one or more nucleic acid molecules from the patient and at least one single-stranded nucleic acid single-stranded nucleic acid molecules of the device, such as a device for performing qRT-PCR.

Microarrays

The levels of the biomarkers (e.g., the biomarkers listed in Tables 1-4 (e.g., COL5A2 (SEQ ID NO: 73 or 211)) and/or PLA2G2A (SEQ ID NO: 380)) may be determined using high-throughput expression profiling platforms, such as microarrays. In particular, a microarray for use in the methods for assessing the responsiveness of a cancer patient (e.g., a patient having cancer that is resistant to one or more cancer therapies other than an sPLA$_2$ hydrolysable, cisplatin-containing liposome) to the liposome contains or is produced by generating oligonucleotide probes (e.g., DNA, cDNA, or RNA probes) capable of hybridizing to one or more biomarkers of interest (e.g., one or more of the biomarkers of Tables 1-4) and/or PLA2G2A (SEQ ID NO: 380) or the complement sequences thereof. Each probe can have, e.g., at least 10, 15, 20, 25, 30, or more contiguous nucleic acid residues (e.g., at least 15) that are complementary or identical to a nucleic acid sequence of a selected biomarker. The probe nucleic sequence can also have at least 85% (e.g., 90%, 95%, 99%, or 100%) sequence identity to the nucleic acid sequence of the gene coding the biomarker (e.g., COL5A2 (SEQ ID NO 73 or 211)) or the complement sequence thereof. In particular, the probe sequences can be complementary to all or a portion of the nucleic acid sequence of the biomarker(s).

For example, microarrays of the invention for determining responsiveness to an sPLA$_2$ hydrolysable, cisplatin-containing liposome can include probes for one or more (e.g., at least 5, 10, 15, or 20 or more (e.g., all)) biomarkers of sensitivity shown in Tables 1 and 3, such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38, or 272), C1QR1 (SEQ ID NO: 13), FNBP1

(SEQ ID NO: 14 or 28), CBFB (SEQ ID NO: 15), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), or LAT2 (SEQ ID NO: 220). Microarrays for determining responsiveness to the liposome can also include probes for one or more (e.g., at least 5, 10, 15, or 20 or more (e.g., all)) biomarkers of resistance listed in Tables 2 and 4, such as SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321).

Microarrays for determining responsiveness to an sPLA$_2$ hydrolysable, cisplatin-containing liposome can also include probes for one or more (e.g., at least 5, 10, 15, or 20 or more (e.g., all)) biomarkers of sensitivity and biomarkers of resistance shown in Tables 1-4, such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38, or 272), C1QR1 (SEQ ID NO: 13), FNBP1 (SEQ ID NO: 14 or 28), CBFB (SEQ ID NO: 15), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), SFN (SEQ ID NO: 96 or 324), LISCH7 (SEQ ID NO: 97), EPB41L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). Additionally, microarrays of the invention for determining responsiveness to the liposome can include one or more probes for PLA2G2A (SEQ ID NO: 380).

A microarray probe may be single-stranded or double-stranded. The probe may be labeled (e.g., detectably labeled with a fluorescent molecule, dye molecule, small molecule, epitope tag, barcode sequence, polypeptide, or any other detectable molecule). Probes can be detectably labeled and immobilized on a solid support to form the microarray. Additionally, probes can be detectably labeled and included in, e.g., a tube, such as probes labeled with a fluorescent molecule. For example, probes can be either prefabricated and spotted to the surface or directly synthesized on to the surface (in situ) of the microarray. The microarray can also be configured such that the sequence and position of each member (e.g., probe) of the array is known. For example, a selection of biomarkers whose levels correlates with an increased likelihood of responsiveness to an sPLA$_2$ hydrolysable, cisplatin-containing liposome can be arrayed on a solid support. Hybridization of a labeled probe with a particular target nucleic acid (e.g., an mRNA corresponding to one or more biomarkers of Tables 1-4 and/or PLA2G2A (SEQ ID NO: 380)) indicates that the sample from which the mRNA was derived expresses that biomarker (e.g., the biomarker of sensitivity or resistance to an sPLA$_2$ hydrolysable, cisplatin-containing liposome).

PCR-Based Techniques

As few as one to thirty (e.g., 5 to 30 or 10 to 30, or at least the first 15 of the biomarkers listed in Tables 1-4) biomarkers, optionally in combination with PLA2G2A (SEQ ID NO: 380), may be used to determine patient responsiveness to an sPLA$_2$ hydrolysable, cisplatin-containing liposome using the methods described herein. Tissue or cell samples from a cancer patient (e.g., a patient having cancer that is resistant to one or more cancer therapies other than an sPLA$_2$ hydrolysable, cisplatin-containing liposome) can be conveniently assayed for levels using PCR analysis, such as quantitative real-time PCR (qRT-PCR), or quantitative loop-mediated isothermal amplification (q-LAMP). For example, an mRNA corresponding to a biomarker of Tables 1-4 and/or PLA2G2A (SEQ ID NO: 380) can be detected in a biological sample by (a) producing cDNA from the sample by reverse transcription using at least one primer; (b) amplifying the cDNA so produced using a target polynucleotide as sense and antisense primers to amplify target cDNAs therein; and (c) detecting the presence of the amplified target cDNA using polynucleotide probes. The primers and probes including the target sequences shown in Tables 1-4, such as COL5A2 (SEQ ID NO 73 or 211) and/or SFN (SEQ ID NO: 96 or 324), and/or the sequence of PLA2G2A (SEQ ID NO: 380) may be used to detect the levels of one or more of the indicated biomarkers using PCR. The methods can include one or more steps that allow determination of the levels of target mRNA in a biological sample (e.g., by simultaneously examining the levels of a comparative control mRNA sequence or "housekeeping" gene, such as an actin family member or GAPDH). The primers for these PCR-based assays may be labeled for detection according to methods known in the art.

Sequencing

The levels of the biomarkers shown in Tables 1-4, such as COL5A2 (SEQ ID NO 73 or 211), SFN (SEQ ID NO: 96 or 324), and/or PLA2G2A (SEQ ID NO: 380) may be determined using sequencing technologies, such as next generation sequencing platforms (e.g., RNA-Seq), as described in Mortazavi et al., Nat. Methods 5: 621-628, 2008, hereby incorporated by reference. RNA-Seq is a robust technology for monitoring biomarker levels by direct sequencing of the RNA molecules in a sample. This methodology may include fragmentation of RNA to an average length of, e.g., 200 nucleotides, conversion to cDNA by random priming, and synthesis of double-stranded cDNA (e.g., using the PRO- TOSCRIPT® First Strand cDNA Synthesis Kit from New England Biosciences). The cDNA may then be converted into a molecular library for sequencing by addition of sequence adapters for each library (e.g., from ILLUMINA®/Solexa), and the resulting 50 to 100 nucleotide reads are mapped onto the genome. Exemplary sequencing platforms suitable for use according to the methods include, e.g., pyrosequencing, ILLUMINA® sequencing by synthesis, SOLID® sequencing, ION TORRENT® sequencing, and SMRT® sequencing.

Methods of Determining Patient Responsiveness to an sPLA$_2$ Hydrolysable, Cisplatin-Containing Liposome The invention features diagnostic methods for the detection and screening of cancer patients (e.g., a patient having cancer that is resistant to one or more cancer therapies other than an sPLA$_2$ hydrolysable, cisplatin-containing liposome) that may be responsive to an sPLA$_2$ hydrolysable, cisplatin-containing liposome using one or more of the biomarkers shown in Tables 1-4 (e.g., COL5A2 (SEQ ID NO 73 or 211) or SFN (SEQ ID NO: 96 or 324)), optionally in combination with PLA2G2A (SEQ ID NO: 380). The methods of the invention may be used for predicting a patient's responsiveness to the liposome, and optionally, treating the cancer patient throughout the progression of cancer and/or in cases of recurrence (e.g., after a first line treatment, a second line treatment, and/or a third line treatment).

The invention provides individual biomarkers (e.g., COL5A2 (SEQ ID NO: 73 or 211) and sets of biomarkers (e.g., two or more of the biomarkers listed in Tables 1-4), the levels of which, as detected in a biological sample (e.g., a tumor sample, such as a biopsy) obtained from a cancer patient (e.g., a human with cancer), are indicative of responsiveness to an sPLA$_2$ hydrolysable, cisplatin-containing liposome. The biomarkers were identified using methods similar to those previously described in, e.g., Chen et al. (*Mol. Cancer Ther.* 11:34-33, 2012), Wang et al. (*J. Nat. Cancer Inst.* 105: 1284-1291, 2013), and Knudsen et al. (*PLoS One*, 9: e87415, 2014), each of which are incorporated by reference herein in their entirety.

In particular, an algorithm based on growth inhibition values (G150) of a cell line (e.g., NCI60 cells) subjected to treatment with an sPLA$_2$ hydrolysable, cisplatin-containing liposome and gene expression is determined (e.g., by microarray analysis, reverse transcriptase polymerase chain reaction (RT-PCR), quantitative real-time PCR (qPCR), or next generation sequencing). After normalization, genes with, e.g., a Pearson correlation coefficient greater than about 0.25 or below about −0.25 can be classified as biomarkers of sensitivity or resistance, respectively. In particular, a correlation coefficient of about 0.25 or greater is a statistically significant cut-off known in the art for establishing whether the levels of the biomarker, e.g., the biomarkers shown in Tables 1-4, correlate with the likelihood of cancer treatment sensitivity, such as sensitivity to the liposome. Thus, a correlation coefficient of about 0.25 or greater or about −0.25 or lower can be used to identify biomarkers, such as the biomarkers of Tables 1-4, for predicting patient responsiveness to treatment with the liposome according to the methods described herein.

Comparison of Biomarker Levels

One or more biomarkers of sensitivity and/or resistance, identified as described herein, can be used to predict responsiveness to an sPLA$_2$ hydrolysable, cisplatin-containing liposome by measuring the level of the biomarkers in a biological sample obtained from the cancer patient, optionally in combination with the level of PLA2G2A (SEQ ID NO: 380) in a tumor sample obtained from the cancer patient. A single biomarker (e.g., any of the biomarkers of Tables 1-4, such as COL5A2 (SEQ ID NO: 73 or 211) or SFN (SEQ ID NO: 96 or 324)) may be used to determine the responsiveness of a cancer patient (e.g., a patient having cancer that is resistant to one or more cancer therapies other than an sPLA$_2$ hydrolysable, cisplatin-containing liposome) to the liposome.

For instance, after determining the level of a biomarker of sensitivity (e.g., any of the biomarkers of Tables 1 and 3, such as COL5A2 (SEQ ID NO: 73 or 211)) in a sample (e.g., a tumor sample) from the cancer patient, the level of the biomarker(s) in the sample may be compared to the level of the biomarker(s) in a cell (e.g., a cancer cell) or tissue (e.g., a tumor tissue) known to be sensitive to treatment with an sPLA$_2$ hydrolysable, cisplatin-containing liposome. If the level of the biomarker(s) in the sample from the cancer patient is substantially similar (e.g., identical to or has the same trend of level) to the level of the biomarker(s) in the cell or tissue known to be sensitive to the liposome, then the cancer patient is predicted to be responsive to treatment with the liposome. Alternatively, if the level of the biomarker(s) in the sample from the cancer patient is substantially dissimilar to the level of the biomarker(s) in the cell or tissue known to be sensitive to the liposome, then the cancer patient is predicted to be non-responsive to treatment with the liposome.

The level of the biomarker of sensitivity (e.g., any of the biomarkers of Tables 1 and 3, such as COL5A2 (SEQ ID NO: 73 or 211)) in a sample (e.g., a tumor sample) from the cancer patient may also be compared to the level of the biomarker(s) in a cell (e.g., a cancer cell) or tissue (e.g., a tumor tissue) known to be resistant to treatment with an sPLA$_2$ hydrolysable, cisplatin-containing liposome. If the level of the biomarker(s) in the sample from the cancer patient is substantially similar to the level of the biomarker(s) in the cell or tissue known to be resistant to an sPLA$_2$ hydrolysable, cisplatin-containing liposome, then the cancer patient is predicted to be non-responsive to treatment with the liposome. Alternatively, if the level of the biomarker(s) in the sample from the cancer patient is substantially dissimilar to the level of the biomarker(s) in the cell or tissue known to be sensitive to an sPLA$_2$ hydrolysable, cisplatin-containing liposome, then the cancer patient is predicted to be responsive to treatment with the liposome.

For instance, after determining the level of a biomarker of resistance (e.g., any of the biomarkers of Tables 2 and 4, such as SFN (SEQ ID NO: 96 or 324)) in a sample (e.g., a tumor sample) from the cancer patient, the level of the biomarker(s) in the sample may be compared to the level of the biomarker(s) in a cell (e.g., a cancer cell) or tissue (e.g., a tumor tissue) known to be sensitive to treatment with an sPLA$_2$ hydrolysable, cisplatin-containing liposome. If the level of the biomarker(s) in the sample from the cancer patient is substantially dissimilar to the level of the biomarker(s) in the cell or tissue known to be sensitive to the liposome, then the cancer patient is predicted to be responsive to treatment with the liposome. Alternatively, if the level of the biomarker(s) in the sample from the cancer patient is substantially similar (e.g., identical to or has the same trend of level) to the level of the biomarker(s) in the cell or tissue known to be sensitive to the liposome, then the cancer patient is predicted to be non-responsive to treatment with the liposome.

The level of a biomarker of resistance (e.g., any of the biomarkers of Tables 2 and 4, such as SFN (SEQ ID NO: 96 or 324)) in a sample (e.g., a tumor sample) from the cancer patient may also be compared to the level of the biomarker(s) in a cell (e.g., a cancer cell) or tissue (e.g., a tumor tissue) known to be resistant to treatment with an sPLA$_2$ hydrolysable, cisplatin-containing liposome. If the level of the biomarker(s) in the sample from the cancer patient is substantially similar to the level of the biomarker(s) in the cell or tissue known to be resistant to an sPLA$_2$ hydrolysable, cisplatin-containing liposome, then the cancer patient is predicted to be responsive to treatment with the liposome. Alternatively, if the level of the biomarker(s) in the sample from the cancer patient is substantially dissimilar to the level of the biomarker(s) in the cell or tissue known to be sensitive to an sPLA$_2$ hydrolysable, cisplatin-containing liposome, then the cancer patient is predicted to be non-responsive to treatment with the liposome.

The responsiveness of a cancer patient (e.g., a patient having cancer that is resistant to one or more cancer therapies other than an sPLA$_2$ hydrolysable, cisplatin-containing liposome) to an sPLA$_2$ hydrolysable, cisplatin-containing liposome can also be predicted by comparing the level of a biomarker (e.g., COL5A2 (SEQ ID NO: 73 or 211)) to the level of the biomarker in one or more cells or tissues (e.g., from a cancer patient population) known to be sensitive to treatment with the liposome and one or more cells or tissues (e.g., from a cancer patient population) known to be resistant to treatment with the liposome. In particular, the patient may be determined to be responsive to treatment with an sPLA$_2$ hydrolysable, cisplatin-containing liposome if the level of the biomarker(s) is more similar to the level of the biomarker(s) in a cell or tissue known to be sensitive to treatment with the liposome than to a cell or tissue known to be resistant to treatment with the liposome. Alternatively, the patient may be determined to be non-responsive to treatment with an sPLA$_2$ hydrolysable, cisplatin-containing liposome if the level of the biomarker(s) is more similar to the level of the biomarker(s) in a cell or tissue known to be resistant to treatment with the liposome than to a cell or tissue known to be sensitive to treatment with the liposome.

Additionally, one or more biomarkers of sensitivity (e.g., one or more of COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38, or 272), C1QR1 (SEQ ID NO: 13), FNBP1 (SEQ ID NO: 14 or 28), CBFB (SEQ ID NO: 15), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), or LAT2 (SEQ ID NO: 220)) and one or more biomarkers of resistance (e.g., one or more of SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321)) may be used in combination to determine the responsiveness of a cancer patient (e.g., a patient having cancer that is resistant to one or more cancer therapies other than an sPLA$_2$ hydrolysable, cisplatin-containing liposome) to treatment with an sPLA$_2$ hydrolysable, cisplatin-containing liposome. For example, the predicted responsiveness of a cancer patient may be determined from, e.g., the difference score, which may be defined as the difference between the mean of the level of the one or more biomarkers of sensitivity of Tables 1 and 3 and the mean of the level of the one or more biomarkers of resistance of Tables 2 and 4.

The difference score of the cancer patient can then be compared to the difference score based on the level of the biomarkers in a cell (e.g., a cancer cell) or tissue (e.g., a tumor tissue) known to be sensitive or resistant to treatment with an sPLA$_2$ hydrolysable, cisplatin-containing liposome. In particular, the patient may be determined to be responsive to treatment with an sPLA$_2$ hydrolysable, cisplatin-containing liposome if the difference score is substantially similar to the level of the biomarkers in a cell or tissue known to be sensitive to treatment with the liposome. Alternatively, the patient may be determined to be non-responsive to treatment with an sPLA$_2$ hydrolysable, cisplatin-containing liposome if the difference score is substantially similar to the level of the biomarkers in a cell or tissue known to be resistant to treatment with the liposome. Additionally, the patient may be determined to be responsive to treatment with the liposome if the difference score is substantially similar to the level of the biomarkers in a cell or tissue known to be sensitive to treatment with the liposome than a cell or tissue known to be resistant to treatment with the liposome. Alternatively, the patient may be determined to be non-responsive to treatment with the liposome if the difference score is substantially similar to the level of the biomarkers in a cell or tissue known to be resistant to treatment with the liposome than a cell or tissue known to be sensitive to treatment with the liposome.

One or more biomarkers of sensitivity and/or resistance, identified as described herein, can be used to predict responsiveness to an sPLA$_2$ hydrolysable, cisplatin-containing liposome by measuring the level of the biomarkers in a biological sample obtained from the cancer patient. A single biomarker (e.g., any of the biomarkers of Tables 1-4, such as COL5A2 (SEQ ID NO: 73 or 211)), may be used to determine the responsiveness of a cancer patient (e.g., a patient having cancer that is resistant to one or more cancer therapies other than an sPLA$_2$ hydrolysable, cisplatin-containing liposome) to an sPLA$_2$ hydrolysable, cisplatin-containing liposome. After determining the level of the biomarker(s) in a sample (e.g., a tumor sample) from the cancer patient, the level of the biomarker(s) in the sample may be compared to the level of the biomarker(s) in a cell (e.g., a cancer cell) or tissue (e.g., a tumor tissue) known to be sensitive to treatment with an sPLA$_2$ hydrolysable, cisplatin-containing liposome. If the level of the biomarker(s) in the sample from the cancer patient corresponds to (e.g., is identical to or has the same trend of level as) the level of the biomarker(s) in the cell or tissue known to be sensitive to an sPLA$_2$ hydrolysable, cisplatin-containing liposome, then the cancer patient is predicted to be responsive to treatment with the liposome. Alternatively, if the level of the biomarker(s) in the sample from the cancer patient does not correspond to the level of the biomarker(s) in the cell or tissue known to be sensitive to an sPLA$_2$ hydrolysable, cisplatin-containing liposome, then the cancer patient is predicted to be non-responsive to treatment with the liposome.

The level of the biomarker (e.g., COL5A2 (SEQ ID NO: 73 or 211)) in a sample from the cancer patient may also be compared to the level of the biomarker in a cell (e.g., a cancer cell) or tissue (e.g., a tumor tissue) known to be resistant to treatment with an sPLA$_2$ hydrolysable, cisplatin-containing liposome. If the level of the biomarker in the sample from the cancer patient corresponds to the level of the biomarker in the cell or tissue known to be resistant to an sPLA$_2$ hydrolysable, cisplatin-containing liposome, then the cancer patient is predicted to be non-responsive to treatment with the liposome. Alternatively, if the level of the biomarker in the sample from the cancer patient does not correspond to the level of the biomarker in the cell or tissue known to be resistant to an sPLA$_2$ hydrolysable, cisplatin-containing liposome, then the cancer patient is predicted to be responsive to treatment with the liposome.

The responsiveness of a cancer patient (e.g., a patient having cancer that is resistant to one or more cancer therapies other than the liposome) to an sPLA$_2$ hydrolysable, cisplatin-containing liposome can also be predicted by comparing the level of a biomarker (e.g., COL5A2 (SEQ ID NO: 73 or 211)) to the level of the biomarker in one or more cells or tissues (e.g., from a cancer patient population) known to be sensitive to treatment with the liposome and one or more cells or tissues (e.g., from a cancer patient population) known to be resistant to treatment with the liposome. In particular, the patient may be responsive to treatment with an sPLA$_2$ hydrolysable, cisplatin-containing liposome if the level of the biomarker(s) corresponds to the level of the biomarker(s) in a cell or tissue known to be sensitive to treatment with the liposome relative to the level of the biomarkers in a cell or tissue known to be resistant to treatment with the liposome. Alternatively, the patient may be non-responsive to treatment with an sPLA$_2$ hydrolysable, cisplatin-containing liposome if the level of the biomarker(s) corresponds to the level of the biomarker(s) in a cell or tissue known to be resistant to treatment with the liposome relative to the level of the biomarkers in a cell or tissue known to be resistant to treatment with the liposome.

For example, the patient may be responsive to treatment with an sPLA$_2$ hydrolysable, cisplatin-containing liposome if the difference score (e.g., the difference between the mean of the level of the one or more biomarkers of sensitivity of Tables 1 and 3 and the mean of the level of the one or more biomarkers of resistance of Tables 2 and 4) corresponds to the level of the biomarkers in a cell or tissue known to be sensitive to treatment with the liposome. Alternatively, the patient may be non-responsive to treatment with an sPLA$_2$ hydrolysable, cisplatin-containing liposome if the difference score corresponds to the level of the biomarkers in a cell or tissue known to be resistant to treatment with the liposome. Additionally, the patient may be responsive to treatment with an sPLA$_2$ hydrolysable, cisplatin-containing liposome if the difference score corresponds to the level of the biomarkers in a cell or tissue known to be sensitive to treatment with the liposome relative to the level of the biomarkers in a cell or tissue known to be resistant to treatment with the liposome. Alternatively, the patient may be non-responsive to treatment with an sPLA$_2$ hydrolysable, cisplatin-containing liposome if the difference score corresponds to the level of the biomarkers in a cell or tissue known to be resistant to treatment with the liposome relative to the level of the biomarkers in a cell or tissue known to be sensitive to treatment with the liposome.

Preferably, the cell or tissue known to be either sensitive or resistant to an sPLA$_2$ hydrolysable, cisplatin-containing liposome is of the same cancer type as the cancer patient with an unknown responsiveness to the liposome. For example, the cancer patient and the cell or tissue known to be either sensitive or resistant to an sPLA$_2$ hydrolysable, cisplatin-containing liposome may both have a cancer type selected from a solid tumor or a hematological cancer, e.g., breast cancer (e.g., a ER-positive breast cancer or medullary carcinoma), prostate cancer, ovarian cancer (e.g., ovarian adenocarcinoma or embryonal carcinoma), liver cancer (e.g., hepatocellular carcinoma (HCC) or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system.

In particular, the cancer of the patient and the cell or tissue with known resistance or sensitivity to an sPLA$_2$ hydrolysable, cisplatin-containing liposome is, e.g., breast cancer (e.g., ERpos breast cancer and/or a metastatic form of breast cancer), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN).

Machine learning techniques such as Neural Networks, Support Vector Machines, K Nearest Neighbor, and Nearest Centroids may also be employed to develop models that discriminate patients sensitive to treatment with an sPLA$_2$ hydrolysable, cisplatin-containing liposome from those resistant to treatment with the liposome using biomarker levels as model variables which assign each patient a classification as sensitive or resistant to treatment with the liposome. Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; V. Tresp et al., "Neural Network Modeling of Physiological Processes," in Hanson S. J. et al. (Eds.), Computational Learning Theory and Natural Learning Systems 2, MIT Press, 1994, each of which are hereby incorporated by reference in their entirety.

Biomarkers of Sensitivity and Resistance

The levels of one or more of the biomarkers of Tables 1-4 can be used to determine cancer patient responsiveness to treatment with an sPLA$_2$ hydrolysable, cisplatin-containing liposome. Once determined to be responsive using the methods of the invention, the patient can be treated with the liposome alone or the liposome and one or more of the other therapies described herein.

TABLE 1 mRNA biomarkers of sensitivity to cisplatin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| ITGA4 | 213416_at | 0.46 | CAGGCCTCTCAGATACAAGGGGAAC | 1 |
| MSN | 200600_at | 0.45 | ATAGCTGCCTTAAAGTCAGTAACTT | 2 |
| FAM46A | 221766_s_at | 0.41 | CACCATGCTGGCTATCCGGGTGTTA | 3 |
| ITGB2 | 202803_s_at | 0.39 | CTCCACTCTGACTGGCACAGTCTTT | 4 |
| DOCK2 | 213160_at | 0.39 | GATTCCTGAACTCAAGGTACCAGCA | 5 |
| EVL | 217838_s_at | 0.39 | GATCATCGACGCCATCAGGCAGGAG | 6 |
| SACS | 213262_at | 0.38 | GTGTGGTTGAACAGGATGCAATCTT | 7 |
| PTPRCAP | 204960_at | 0.37 | GCTTCCCAAGATGCCATGGCTGGAC | 8 |
| EBI2 | 205419_at | 0.37 | GCAGGACTTCCCTTATAAAGCAAAA | 9 |
| PTPRC | 212587_s_at | 0.37 | GATTATAACCGTGTTGAACTCTCTG | 10 |
| ANP32E | 221505_at | 0.37 | GTTTTCGGTCCTATTTTAATGCTCT | 11 |
| SFPQ | 201586_s_at | 0.36 | AAAGACCAACAAATCTCAAGCCCTA | 12 |
| C1QR1 | 202878_s_at | 0.36 | GGTCTGTTCTTGTAGATAATGCCCT | 13 |
| FNBP1 | 213940_s_at | 0.36 | TGCTGGCCACGGATTTTGACGACGA | 14 |
| CBFB | 202370_s_at | 0.35 | GGTGTTGTACAGCTCACATGTTTAC | 15 |
| HCLS1 | 202957_at | 0.35 | GGTTTGCCTCATTGTGCTATTTGCC | 16 |
| IFI16 | 208965_s_at | 0.35 | ATAAGCATTGATTCCTGCATTTCTG | 17 |
| PTPRC | 212588_at | 0.35 | GCATTTAGTCCAATGTCTTTTTAAG | 18 |
| SFRS7 | 213649_at | 0.35 | ATCATGCTGAGGCGCCTTGCAAATC | 19 |
| CAP350 | 204373_s_at | 0.34 | ATGACTGGTATGATAGCTCTTGACA | 20 |
| IGLL1 | 206660_at | 0.34 | CAATCCAAGCATAACTCAGTGACGC | 21 |
| DOCK10 | 219279_at | 0.34 | GAATGTGTAGCTCAAATGCAAACCA | 22 |
| WASPIP | 202664_at | 0.33 | TTCCCTCCTTATAGTCAAGGACCGT | 23 |
| FLI1 | 204236_at | 0.33 | TGACCTCGGTCACAAAAGCAGTTTT | 24 |
| PTPRC | 207238_s_at | 0.33 | GAACAGTTTGTACAGACGTATGCTT | 25 |

TABLE 1-continued mRNA biomarkers of sensitivity to cisplatin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| IFI16 | 208966_x_at | 0.33 | TACAACACTATACATACACACCACC | 26 |
| HDGFRP3 | 209524_at | 0.33 | TTATGCCAGCTTATATTGTGAGAAC | 27 |
| FNBP1 | 212288_at | 0.33 | GAGTTGCCTGTTTGTCTCTGGAGAT | 28 |
| SEPT6 | 212414_s_at | 0.33 | GCTGCAGTGTAGATGGCTCTTGTTT | 29 |
| ARHGAP15 | 218870_at | 0.33 | ACGTTGTCACCGGAGCACTGAAGAT | 30 |
| RASSF2 | 203185_at | 0.32 | ATAGCAGCACACATTTTCACGTTTC | 31 |
| GMFG | 204220_at | 0.32 | AAGACCGGCAGATGGTGGTGCTGGA | 32 |
| SYNCRIP | 209025_s_at | 0.32 | ATTTGGCTCAAGTCCATTTGGCTGT | 33 |
| HDGFRP3 | 209526_s_at | 0.32 | GCATGAAGTTGCCCTTAACCACTAA | 34 |
| ARHGEF6 | 209539_at | 0.32 | TAACCATGCTTACACACTAAACTAT | 35 |
| TMEM5 | 204808_s_at | 0.31 | TGCCCGGTCGGAGTAAACACAGAAT | 36 |
| CENTB1 | 205213_at | 0.31 | GATGTCAACTGGGTCAATGGGGGCC | 37 |
| SFPQ | 214016_s_at | 0.31 | GTTGGCTGATATTGGAGTGCTCATT | 38 |
| BCAT1 | 214452_at | 0.31 | CCTTTTGTACTTCACTCAGATACTA | 39 |
| LCP1 | 208885_at | 0.3 | TAAGCATCCTTAGGGTTCTGCCTCT | 40 |
| CORO1A | 209083_at | 0.3 | CTCATCTCCCTCAAGGATGGCTACG | 41 |
| SLC4A7 | 209884_s_at | 0.3 | TGTGAATCATCCTGCCTTTCAAATT | 42 |
| RAFTLIN | 212646_at | 0.3 | TACAAACCACATTACTTCTGTCACT | 43 |
| CKIP-1 | 218223_s_at | 0.3 | GTCCCGGATCCAGGACCTGGTAGCA | 44 |
| SNRP70 | 201221_s_at | 0.29 | AGTGAAGAGGTCGTCCTCTCCATCT | 45 |
| BNIP3 | 201849_at | 0.29 | GCTGAAGGCACCTACTCAGTATCTT | 46 |
| SLA | 203761_at | 0.29 | TAAGCATTCCGTCCATCTAAGCTCA | 47 |
| MFNG | 204153_s_at | 0.29 | TGATGGAGCATAACGGGTCCCAGCC | 48 |
| LOC57821 | 206721_at | 0.29 | ATGATTTCTTAGGGTCTGTGTACTT | 49 |
| CBLB | 209682_at | 0.29 | GTTCCATTTCTCTCATTCACAAGAT | 50 |
| QKI | 212636_at | 0.29 | GAGGCCAAGAAATTCCATGTTGTTT | 51 |
| ZRF1 | 213097_s_at | 0.29 | AAAGCTGTGAATCTGTTCCCTGCTG | 52 |
| FTL | 213187_x_at | 0.29 | ATGAGCTCCCAGATTCGTCAGAATT | 53 |
| SFRS7 | 214141_x_at | 0.29 | TCCCCATCAGGAAGTCCTCGCAGAA | 54 |
| VIM | 201426_s_at | 0.28 | TGAGTCCCTGGAACGCCAGATGCGT | 55 |
| PWP1 | 201606_s_at | 0.28 | TTAGAGCCAGTCTTCACACTCGGAA | 56 |
| AKAP7 | 205771_s_at | 0.28 | AAAACTTCCCCGGTATGATGATTGT | 57 |
| AF1Q | 211071_s_at | 0.28 | TCAGTGGGCACAGTTCTTCAGCTAC | 58 |
| DICER1 | 213229_at | 0.28 | ACTAGCTCATTATTTCCATCTTTGG | 59 |
| PDE4DIP | 213388_at | 0.28 | AATTATGAGTTTCTATCTGTGTCCA | 60 |
| CAP350 | 213956_at | 0.28 | GGGAAGTCCACATAGCGTCATTAAT | 61 |
| AIF1 | 215051_x_at | 0.28 | TTCAGCTACCCTGACTTTCTCAGGA | 62 |

TABLE 1-continued mRNA biomarkers of sensitivity to cisplatin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| TRAF3 | 221571_at | 0.28 | GGCATGATGTCCGGTGATTTCTGTA | 63 |
| MBNL1 | 201152_s_at | 0.27 | ACTCTTGAGGGTTGATTATGCTGCA | 64 |
| FMNL1 | 204789_at | 0.27 | GGACCTCATCTCTGAGCTGAAACGG | 65 |
| TMEFF1 | 205122_at | 0.27 | GTTGGTGTTTAAAGATCTGAAGTGT | 66 |
| IL6R | 205945_at | 0.27 | GAAGCACCATAACTTTGTTTAGCCC | 67 |
| SIVA | 210792_x_at | 0.27 | ACAGCATGAGGCGGCCGGGGAGCTG | 68 |
| MCAM | 211340_s_at | 0.27 | GCTATGGTTATATTAGCACCAAACT | 69 |
| POLR2I | 212955_s_at | 0.27 | GGCCGACAACAGCTGCATCTATGTC | 70 |
| T3JAM | 213888_s_at | 0.27 | TGAAAAAGGGTTTCTATTCTCTCTG | 71 |
| C1orf24 | 217967_s_at | 0.27 | AGTATCAGTCGGTGCAACAGTTGGC | 72 |
| COL5A2 | 221730_at | 0.27 | TGAAGTTGATCCTGAGACTCTTGAA | 73 |
| LAPTM5 | 201_720_s_at | 0.26 | TACTCAGAGGTGTGACCCTCGCCAG | 74 |
| JARID1A | 202040_s_at | 0.26 | GTCGTACTATCTTACTGAGCCACAG | 75 |
| CUGBP2 | 202156_s_at | 0.26 | AAGGCGTAACGAGTTCATCTTTCTT | 76 |
| PTPN7 | 204852_s_at | 0.26 | CCTTGATACCAGCTCTCTGTGGAAA | 77 |
| LCP2 | 205269_at | 0.26 | AAATCACTAAACCTCGTTTTCTCAG | 78 |
| RASA4 | 212706_at | 0.26 | AGCGTCCTTATCTTTCAGAGCTACA | 79 |
| FTL | 212788_x_at | 0.26 | AAACCCCAGACGCCATGAAAGCTGC | 80 |
| CD3D | 213539_at | 0.26 | GGGAACACTGCTCTCAGACATTACA | 81 |
| EIF4A1 | 214805_at | 0.26 | CTTTTTCCTGGGTCATGCTGCAACA | 82 |
| NKTR | 215338_s_at | 0.26 | GATGGGGTGCATGTAGTCTTTGGAC | 83 |
| C1orf24 | 217966_s_at | 0.26 | GAAGGTGTGATCTGTGGGACTGTCT | 84 |
| C2orf33 | 219137_s_at | 0.26 | GTACGTTTTTACTCAGTTCATGCGT | 85 |
| TMEM22 | 219569_s_at | 0.26 | GCTTCTCGTGCTGCACATATTTCCT | 86 |
| GIMAP6 | 219777_at | 0.26 | GTGAACAGACTTGAAACTCCAGAGC | 87 |
| RAP1B | 200833_s_at | 0.25 | ATCATTTTCAGGCTTCTGCAGCTGT | 88 |
| SRRM1 | 201225_s_at | 0.25 | GCATGTTGTTTGCCAGGACACTGTG | 89 |
| PWP1 | 201608_s_at | 0.25 | TTGTGCTTGCTCTTCAGATGGATGG | 90 |
| EDG1 | 204642_at | 0.25 | TAGCCAGGATCCTTGGTGTCCTAGG | 91 |
| CD47 | 211075_s_at | 0.25 | GCGGCGTGTATACCAATGCATGGCC | 92 |
| CG018 | 213375_s_at | 0.25 | GAATAACTTTGGCTGTTGTGCTAAA | 93 |
| TPK1 | 221218_s_at | 0.25 | TGGCCCGCGTGATTGTGGCATTTAA | 94 |
| COL5A2 | 221729_at | 0.25 | CATAACTGTTAGACTTCCCGTTTCT | 95 |

TABLE 2 mRNA biomarkers of resistance to cisplatin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| SFN | 33323_r_at | -0.48 | TCAATAAAGTTCCCCTGTGACACTC | 96 |
| LISCH7 | 208190_s_at | -0.47 | CTCCCCTATGATGGGCGGCTACTGG | 97 |
| EPB41L4B | 220161_s_at | -0.47 | ATCAGTTGATTCTTGTGCCATTTTT | 98 |
| MST1R | 205455_at | -0.46 | TGAGCCAGTGAGGGCAGTCCTGCAA | 99 |
| ITGB4 | 204990_s_at | -0.45 | GCATCATCACCATAGAGTCCCAGGA | 100 |
| SFN | 209260_at | -0.45 | TCTTGCTCCAAAGGGCTCCGTGGAG | 101 |
| C20orf35 | 218094_s_at | -0.45 | ATACGCCCTTGGCACAGTCGGATGA | 102 |
| SFN | 33322_i_at | -0.45 | GTCTGCTGGGTGTGACCATGTTTCC | 103 |
| TACSTD1 | 201839_s_at | -0.43 | GTGCGTGGGACGAAGACATCTTTGA | 104 |
| C19orf21 | 212925_at | -0.42 | TGGTCCCCTTCACCTGGGAGAAAAG | 105 |
| KRT8 | 209008_x_at | -0.41 | GGGCCAAGCAGGACATGGCGCGGCA | 106 |
| JUP | 201015_s_at | -0.4 | AGCTTCAGACTCAAGTACCCATTCT | 107 |
| KRT18 | 201596_x_at | -0.4 | GAGCTGCTGAGACGACGCTCACAGA | 108 |
| FA2H | 219429_at | -0.39 | GAGAAGCAGTTTGACGGACCTTGTG | 109 |
| MGAT4B | 220189_s_at | -0.38 | GGTGATTCTGAGCGAGATCTTCCTG | 110 |
| DSG2 | 217901_at | -0.37 | GCAGCCTTGGAAACCTAACCTGCCT | 111 |
| LRP5 | 209468_at | -0.36 | CCTGCAGCACCGACGTGTGTGACAG | 112 |
| GJB3 | 215243_s_at | -0.36 | ACTTGGCTCAGTGGAAGCCCTCTTT | 113 |
| TACSTD2 | 202286_s_at | -0.35 | ACATTGCCCGGAAACTCAGTCTATT | 114 |
| LAD1 | 203287_at | -0.35 | GCTGTGGATCTGTTTGGCCAGGGTC | 115 |
| AGR2 | 209173_at | -0.35 | GTTAGAGCCGATATCACTGGAAGAT | 116 |
| HTATIP2 | 209448_at | -0.35 | AGATTTGTCAGCCCTATCTCAAACT | 117 |
| LOC57228 | 209679_s_at | -0.35 | AGGTCTTCCCAGAGGCTGGATACCA | 118 |
| BCL2L1 | 212312_at | -0.35 | GTCTTCCCTACCTCAGGCAGGAAGG | 119 |
| GPX2 | 202831_at | -0.34 | CTACCCTTATGATGACCCATTTTCC | 120 |
| SOX9 | 202935_s_at | -0.34 | AAATGCTCTTATTTTTCCAACAGCT | 121 |
| TPBG | 203476_at | -0.34 | GTGTATAGTGTTTTACCCTCTTCTT | 122 |
| LGALS4 | 204272_at | -0.34 | TCATCAAGGGCTATGTGCCTCCCAC | 123 |
| PHLDA1 | 217996_at | -0.34 | CCCCGCACCAGATCAAGTAGTTTGG | 124 |
| PLEK2 | 218644_at | -0.34 | CCCTCCTACCAGATGACACAGACAA | 125 |
| TNFRSF21 | 218856_at | -0.34 | TGTATGGTTTTCACCTGGACACCGT | 126 |
| IER3 | 201631_s_at | -0.33 | AACTCCGTCTGTCTACTGTGTGAGA | 127 |
| RAI3 | 203108_at | -0.33 | CCCACTGGCCTGAATCTACACTGGA | 128 |
| BENE | 209373_at | -0.33 | ACATTACATCCGTGGATTCTCCTGC | 129 |
| MGC50853 | 212400_at | -0.33 | GGCCCTGGGCCAGGGTGATTGGACT | 130 |
| RAI3 | 212444_at | -0.33 | TTTAGCCCTCATGACTGTATTTTCT | 131 |
| CLIC3 | 219529_at | -0.33 | ACACGCTGCAGATCGAGGACTTTCT | 132 |

TABLE 2-continued mRNA biomarkers of resistance to cisplatin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
| --- | --- | --- | --- | --- |
| CLDN3 | 203954_x_at | -0.32 | ACCGGCAGCCCTGGAAGGGGCACTT | 133 |
| FGFR4 | 204579_at | -0.32 | TACCAGCAGGAGGTTCTGGGCCTCT | 134 |
| PPARG | 208510_s_at | -0.32 | CATCTTTCAGGGCTGCCAGTTTCGC | 135 |
| FBP1 | 209696_at | -0.32 | GGGCTACGCCAAGGACTTTGACCCT | 136 |
| CPNE3 | 202119_s_at | -0.31 | AATCTAGTCACCTAACCTTGTGGTT | 137 |
| AREG | 205239_at | -0.31 | ATTTCAAAATTTCTGCATTCACGGA | 138 |
| VIL1 | 205506_at | -0.31 | AACACCTGTCCATTGAAGATTTCAC | 139 |
| GATA6 | 210002_at | -0.31 | GACATTCTTATGCTTCTTTTACAAC | 140 |
| TCF7L2 | 212761_at | -0.31 | AATGTTTCCTAACAGTTGTGATGTT | 141 |
| PP1201 | 217730_at | -0.31 | GGGTGAAGAGAGACTCGGTGCGGGC | 142 |
| FLJ20847 | 219053_s_at | -0.31 | CGACCGCCTGTATGTTTGTGTAATT | 143 |
| GPR172A | 222155_s_at | -0.31 | AAGGCCTATCAGCTTCTATCAGCCC | 144 |
| ITGA6 | 201656_at | -0.3 | GTCACTGGTCTGTTTGCATTTGATA | 145 |
| ZNF165 | 206683_at | -0.3 | AGCTCAAAACTTGCTAGGCATCAGA | 146 |
| FLNB | 208613_s_at | -0.3 | GCAGCAAAGCTGGCTCCAACATGCT | 147 |
| MCCC2 | 209623_at | -0.3 | AAACACTATCTACTTCCTTTGTCAT | 148 |
| FLJ20273 | 218035_s_at | -0.3 | GAGGATCATGCCCTTAGCAAGTACT | 149 |
| TMEM16A | 218804_at | -0.3 | AACATCATTTTAGCAAAGGCCAGGA | 150 |
| RAB11FIP1 | 219681_s_at | -0.3 | TGTCCTTGTTACATTGAGGTTAAGA | 151 |
| SLC3A2 | 200924_s_at | -0.29 | TCCCTACTGCATGGGGACTTCCACG | 152 |
| EFNA1 | 202023_at | -0.29 | CCACCTTCACCTCGGAGGGACGGAG | 153 |
| SORL1 | 203509_at | -0.29 | TAATTACACGTTCACCGTCCAAGCA | 154 |
| PLS1 | 205190_at | -0.29 | TTCCCTTTCTACCATTGATTTAAAT | 155 |
| GALIG | 208949_s_at | -0.29 | AGTACTGGTTGAACCTGACCACTTC | 156 |
| EHD1 | 209038_s_at | -0.29 | AAATACATAAGCTAGTTTCTGTTCT | 157 |
| NR2F2 | 209120_at | -0.29 | GTAACGTGATTGATTCAGTATCTTA | 158 |
| SERPINB1 | 213572_s_at | -0.29 | AATACATCCGATGCGTAGATTCTTG | 159 |
| PCK2 | 202847_at | -0.28 | AGAATGCTCGGGTGCTAGACTGGAT | 160 |
| ARF6 | 203311_s_at | -0.28 | GGACGGACTCTATGAGGGGCTCACA | 161 |
| TGFA | 205016_at | -0.28 | GGAATGACTCAAATGCCCAAAACCA | 162 |
| CST6 | 206595_at | -0.28 | TCCTCTCAGCTCCTAAAGCACAACT | 163 |
| PXN | 211823_s_at | -0.28 | ACATGTTCGCACCCAAGTGTGGCGG | 164 |
| SORL1 | 212560_at | -0.28 | TTTCAGATGGAGTACCAGCACCGAA | 165 |
| SLC39A4 | 219215_s_at | -0.28 | TGGCACTCGCGGTTGGAGTCAGCGA | 166 |
| GCNT3 | 219508_at | -0.28 | GGCCATCTATGGGACTGAACTTTGA | 167 |
| S100A11 | 200660_at | -0.27 | GAAGAAACTGGACACCAACAGTGAT | 168 |

TABLE 2-continued mRNA biomarkers of resistance to cisplatin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
| --- | --- | --- | --- | --- |
| ITPR3 | 201189_s_at | -0.27 | GCTGTAGCCAGTGCAGACCTCACTG | 169 |
| DHCR7 | 201790_s_at | -0.27 | AGGTGTCCAGTACCTAATCACGCTC | 170 |
| TCIRG1 | 204158_s_at | -0.27 | TTGCCGTGATGACCGTGGCTATCCT | 171 |
| NR2F2 | 209121_x_at | -0.27 | GAATACGTTAGGAGCCAGTACCCCA | 172 |
| SLC25A1 | 210010_s_at | -0.27 | GAAGCTGCTCAACAAAGTGTGGAAG | 173 |
| SERPINB6 | 211474_s_at | -0.27 | GGAATGTCCCAGACAGACCTGTCTC | 174 |
| ARTN | 216052_x_at | -0.27 | CCTTCATGGACGTCAACAGCACCTG | 175 |
| LOC51123 | 218059_at | -0.27 | GGCCCGGATATGGCTCGTGGACAGC | 176 |
| S100A14 | 218677_at | -0.27 | AGGAGTCTCCACCAGAGGGAGGCTC | 177 |
| FCGRT | 218831_s_at | -0.27 | GAGCACCACTACTGCTGCATTGTGC | 178 |
| RAB20 | 219622_at | -0.27 | ACTCTGACATTTCTTGTTCTCAAGC | 179 |
| SPDEF | 220192_x_at | -0.27 | CCAGCATTTCCAGAGCAGAGCCTAC | 180 |
| PNAS-4 | 221648_s_at | -0.27 | GCGTGTCTTGAGTTCCATGCAAATT | 181 |
| PXN | 201087_at | -0.26 | AATGGTGACAGTCCAAACCACTCCA | 182 |
| TPD52L2 | 201379_s_at | -0.26 | GGCCCTGCATGTCAGATGGCGTGGT | 183 |
| ALDH3A2 | 202054_s_at | -0.26 | TGATCATAAATTCTCCCCAACTATA | 184 |
| ARF6 | 203312_x_at | -0.26 | AAAGTTGCCAAGATGCTCCTTGTTG | 185 |
| GPA33 | 205929_at | -0.26 | GTCTCACCCAACTGCAGTTTACTAT | 186 |
| — | 208540_x_at | -0.26 | GACGGAGTTCCTAAGCTTCATGAAT | 187 |
| FLNB | 208614_s_at | -0.26 | TCAGCCTGGGCAGTCTTACCAAAAT | 188 |
| TSPAN-1 | 209114_at | -0.26 | TGCTGTGGCTTCACCAACTATACGG | 189 |
| CDH17 | 209847_at | -0.26 | CCTTGACTCCTTTGGTATTTCACTG | 190 |
| SERPINB1 | 212268_at | -0.26 | ACAGCAGGCATCGCAACTTTCTGCA | 191 |
| LCN2 | 212531_at | -0.26 | CAAGAGCTACAATGTCACCTCCGTC | 192 |
| KIAA0984 | 213913_s_at | -0.26 | GTTTGTCTCTTGTTGTTCTGAAGGA | 193 |
| ACSL5 | 218322_s_at | -0.26 | CTCTCTAGTTAGATATCTGACTTGG | 194 |
| MUC13 | 218687_s_at | -0.26 | TCCAGCCTCGGGGTGTAGGTTTCTG | 195 |
| FAM11B | 219253_at | -0.26 | ACTCGTCTCACGCCGTGTTTGAGAT | 196 |
| SH2D3A | 219513_s_at | -0.26 | GCCAGAGTTCAAATGTGACTCCACC | 197 |
| ANXA2 | 201590_x_at | -0.25 | CAAGCCCCTGTATTTTGCTGATCGG | 198 |
| TM4SF3 | 203824_at | -0.25 | AGACCACAGATATCTTCTAGACATA | 199 |
| NT5E | 203939_at | -0.25 | GTCACTGTAAATCATTCTTAAGCCC | 200 |
| TETRAN | 209215_at | -0.25 | AAGGCTGTCAGGGCTTCTGTTTGTT | 201 |
| CTBP2 | 210835_s_at | -0.25 | GTAGACACCTGCACGCATAGGATTG | 202 |
| SOD | 211708_s_at | -0.25 | TTGCCACTTTCTTGCGATATGCTGT | 203 |

TABLE 2-continued mRNA biomarkers of resistance to cisplatin. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| DNMBP | 212838_at | -0.25 | GCCATTCCAGAAGTAGCTTATCCTA | 204 |
| TMC5 | 219580_s_at | -0.25 | CCAATACCCCACCGTGATGACTTGA | 205 |

TABLE 3 mRNA biomarkers of sensitivity to an sPLA2 hydrolysable, cisplatin-containing liposome. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| CALD1 | 212077_at | 10861321835689.1 | AATTCTCTGTTATCTTTACGAGGTA | 206 |
| COL6A2 | 209156_s_at | 8535698909744.43 | CACGAGAAGGACTATGACAGCCTGG | 207 |
| FERMT2 | 209210_s_at | 5291552917682.63 | TGATTTGCCACAATGTCCTTAACTC | 208 |
| BNIP3 | 201849_at | 5145685657339.48 | GCTGAAGGCACCTACTCAGTATCTT | 209 |
| RAB31 | 217762_s_at | 4734688539598.5 | AGACCTGGCACTTCAGTAACTCAGC | 210 |
| COL5A2 | 221730_at | 4647176466910.36 | GACTCTTGAAGTAATGGCTGATCCT | 211 |
| MPO | 203948_s_at | 4518211644157.6 | GGGACTTTGTCAACTGCAGTACACT | 212 |
| SRPX | 204955_at | 4340511505629.07 | CCTTTCTTTACTCCATCATGGCTGG | 213 |
| ARHGDIB | 201288_at | 4263392661779.67 | ATCACTAACAGGTCTTTGACTCAGG | 214 |
| TMEM47 | 209656_s_at | 4156685173988.01 | GAATTCATGGTATCCTGGTTATTTT | 215 |
| CSRP2 | 207030_s_at | 3960151282910.27 | AACTACTGTGAAATTCTACCAGCAT | 216 |
| DPYSL3 | 201431_s_at | 3876388962016.02 | GACACCTGAGCCTGGATTTTCACTC | 217 |
| HTRA1 | 201185_at | 3845854940391.73 | TCAAACGGCCGAAGTTGCCTCTTTT | 218 |
| SLC39A6 | 202088_at | 3547148987590.88 | ATACTAGGCCTGTCTGTGGCATTCT | 219 |
| LAT2 | 221581_s_at | 3545380986375.43 | GGATTTAGGATAAGCTGTCACCCAG | 220 |
| ENAH | 217820_s_at | 3385939870513.75 | GGTCAGCAACCTCTTTTGATTTTGT | 221 |
| RPS4Y1 | 201909_at | 3384951327956.31 | GACAGGTGAACATTTCCGCCTGGTC | 222 |
| DOCK2 | 213160_at | 3367491706976.35 | GATTCCTGAACTCAAGGTACCAGCA | 223 |
| COL1A1 | 202311_s_at | 3222960671378.67 | TGTTCCTTTTTGTTCAAAGTCTATT | 224 |
| GMFG | 204220_at | 3013566458581.29 | AGGTGTTCGAAATCCGCACCACTGA | 225 |
| CYR61 | 201289_at | 2999506373414.97 | GTGGAGTTGATGACTTTCTGTTTTC | 226 |
| RHOB | 212099_at | 2978300392812.93 | TGCAGGTCATGCACACAGTTTTGAT | 227 |
| CORO1A | 209083_at | 2968352455386.15 | GCTCCAGAAGCGCTTGGACAGGCTG | 228 |
| ID4 | 209291_at | 2948241975028.96 | GGCATAATGGCAAATCCTTCAAGCA | 229 |
| RARRES2 | 209496_at | 2907180844659.6 | CCCCATAGAGACCCAAGTTCTGCGG | 230 |
| SOX4 | 201417_at | 2862450307972.36 | GTAAACCACATCTTTTTTGCACTTT | 231 |
| NID1 | 202007_at | 2798544570884.12 | CACTTTTTGTATTTATCGTTTCATA | 232 |
| CALD1 | 201616_s_at | 2776573094080.12 | GACGCAGGACGAGCTCAGTTGTAGA | 233 |

TABLE 3-continued mRNA biomarkers of sensitivity to an sPLA2 hydrolysable, cisplatin-containing liposome.
Dashes mean that the Affymetrix probeset has not been mapped to a specific gene.
Affymetrix IDs refer to the array type HG-U133A.

| Gene | Affymetrix ID | Correlation | Affymetrix Probe Sequence | SEQ ID NO: |
|---|---|---|---|---|
| SERPINE2 | 212190_at | 2767126943194.04 | TGTTGTGCAGTGTGCCTGTCACTAC | 234 |
| CTSL1 | 202087_s_at | 2681524741399.96 | CACTTACTGACTTTGCATTTTCGTT | 235 |
| C3orf14 | 219288_at | 2679480387909.32 | GGTGGTTTCTCTTGAGACTCGTTAC | 236 |
| DKK3 | 202196_s_at | 2608335983440.84 | TTGGCAGTTGCATTAGTAACTTTGA | 237 |
| SCRN1 | 201462_at | 2582074623391.62 | TCATGTGCACATGCCGTTGCAGCAC | 238 |
| MT1M | 217546_at | 2555792977629.17 | CGTTGGAGAACTGCAGCTGCTGTGC | 239 |
| PLAU | 205479_s_at | 2529115320523.6 | AGCAGCTGAGGTCTCTTGAGGGAGC | 240 |
| NREP | 201310_s_at | 2514590941976.06 | CATTGGCCTGAGTTTCTTGTGCATT | 241 |
| HLA-B | 208729_x_at | 2501423496784.03 | GAGCCTACCTGGAGGGCGAGTGCGT | 242 |
| PTPRC | 212588_at | 2494855639496.51 | GTTTTCAATTTTGCATGCTCGATTA | 243 |
| HDGFRP3 | 209524_at | 2438222715080.89 | TTATGTGTACATTATTGTTGCTATT | 244 |
| CELF2 | 202157_s_at | 2427790438608.2 | CTTCCCGGTCACTGGTAACAATAGC | 245 |
| SFRP1 | 202037_s_at | 2413217767593.8 | GTACCTGTGGGTTAGCATCAAGTTC | 246 |
| HLA-B | 211911_x_at | 2358346288074.42 | CTGAGAGCCTACCTGGAGGGCCTGT | 247 |
| LOX | 215446_s_at | 2354236167712.24 | TTGGGCCTTTTATCTGTCTATCCAT | 248 |
| CLU | 208791_at | 2341547177698.15 | CAGTGTGACAAGTGCCGGGAGATCT | 249 |
| SH3BGRL | 201312_s_at | 2249866543302.91 | AGAATCTTTTCTATGCCTCTATTCC | 250 |
| INHBA | 210511_s_at | 2238550007854.02 | GCCATATAGCAGGCACGTCCGGGTC | 251 |
| MMP1 | 204475_at | 2203074303300.14 | GGCAAGGGATAACTCTTCTAACACA | 252 |
| WIPF1 | 202664_at | 2194537285288.12 | TTCCCTCCTTATAGTCAAGGACCGT | 253 |
| ADAMTS1 | 222162_s_at | 2144423953975.08 | AATAACGCAAATGGCTTCCTCTTTC | 254 |
| THY1 | 208850_s_at | 2141423198789.74 | GGCCTAGCACGGACATGGTCTGTCC | 255 |
| UCHL1 | 201387_s_at | 2140899985376.98 | TGATGGACGAATGCCTTTTCCGGTG | 256 |
| MYH10 | 212372_at | 2139390916542.17 | GATCCTCTGCAATGTGCTTGAAAAC | 257 |
| TYMS | 202589_at | 2131876162229.91 | TCACAAGCTATTCCCTCAAATCTGA | 258 |
| HCLS1 | 202957_at | 2089924252642.24 | TGATGAGCTTTCCTTTGATCCGGAC | 259 |
| HLA-B | 209140_x_at | 2085546519988.6 | GAGACAGCTGTCTTGTGAGGGACTG | 260 |
| IFI16 | 208966_x_at | 2061722348570.95 | TACACACCACCATATATACTAGCTG | 261 |
| PRKCB | 207957_s_at | 2037662863122.06 | GTGTAGGTGAATGCAAACTCCATCG | 262 |
| BNIP3 | 201848_s_at | 2008580245730.46 | TTCCTCTTTAAACACCCGAAGCGCA | 263 |
| TUSC3 | 213423_x_at | 1987545095813.27 | AACTGTTCCTGACTTTATACTATTT | 264 |
| WNT5A | 205990_s_at | 1982235386738.35 | GCATAATGATATTCACATCCCCTCA | 265 |
| CALD1 | 201617_x_at | 1981280027254.5 | TGTTGTTTCTGCACTTTATAATAAA | 266 |
| HLA-C | 216526_x_at | 1955999731784.71 | AGAGGTGGGGCTGGATGTCTCCATC | 267 |
| URI | 202948_at | 1955342562611.76 | AAGTGCAAAGTTATTCCCCATCTTC | 268 |
| AUTS2 | 212599_at | 1927738178390.84 | TACTTACACCCAAACAGATCCTGAA | 269 |
| THBS2 | 203083_at | 1912997768879.9 | TTGCGTGTGGAGCTGTATTCCCGAG | 270 |

TABLE 3-continued mRNA biomarkers of sensitivity to an sPLA2 hydrolysable, cisplatin-containing liposome.
Dashes mean that the Affymetrix probeset has not been mapped to a specific gene.
Affymetrix IDs refer to the array type HG-U133A.

| Gene | Affymetrix ID | Correlation | Affymetrix Probe Sequence | SEQ ID NO: |
|---|---|---|---|---|
| CHRDL1 | 209763_at | 1895325557387.3 | CCCTTTCACTGTTCTCACAGGACAT | 271 |
| SFPQ | 214016_s_at | 1886539698542.15 | GTTGGCTGATATTGGAGTGCTCATT | 272 |
| CXCL12 | 209687_at | 1857308403453.12 | CAGCAGGGTTTCAGGTTCCAATCAG | 273 |
| HOXC6 | 206858_s_at | 1831591158444.48 | CTGTATTTGTGGTCTCTGTATTTAT | 274 |
| PLAGL1 | 209318_x_at | 1827870818957.99 | ACATCCAAAATGACGGCTGCTATAT | 275 |
| RDX | 212397_at | 1815278384492.07 | GTGGACCCTACTATTCATGTTTTGA | 276 |
| HNRNPH1 | 213619_at | 1813815711802.08 | GCTTAAACTTACGTGCCTTACAGGT | 277 |
| KRAS | 214352_s_at | 1802923545775.42 | CATGCAGACTGTTAGCTTTTACCTT | 278 |
| IL8 | 211506_s_at | 1788698391848.43 | GTCAGTGCATAAAGACATACTCCAA | 279 |
| FAM46A | 221766_s_at | 1787987145165.06 | GGAGTCCTATTTGCAGAACCACTTT | 280 |
| QKI | 212265_at | 1787672566876.18 | ATAACCAACCTATTGCCTATGAGAA | 281 |
| CD53 | 203416_at | 1777870731216.97 | CGAATTAGTCTCCAGCCTCTAAATA | 282 |
| LAPTM5 | 201720_s_at | 1763708973603.65 | TCGGGTCTCTCCATAATTCAGCCCA | 283 |
| FOXG1 | 206018_at | 1752375753099.1 | ACGATTGCCTTCAGTTTGTGTTGTG | 284 |
| MST4 | 218499_at | 1732353014841.79 | AATTCTTTTTATTGGTGCCTATATT | 285 |
| GAPDH GAPDH | AFFX-HUMGAPDH/M33197_M_at | 1692594771893.01 | AAGCTCACTGGCATGGCCTTCCGTG | 286 |
| TUBB2B | 214023_x_at | 1672014039622.35 | GAGATATTTCTGAATTACTGTTGTA | 287 |
| GAPDH | 212581_x_at | 1649610188507.54 | TTTGACGCTGGGGCTGGCATTGCCC | 288 |
| CEBPD | 203973_s_at | 1623762464226.23 | GGACAGCAGACTGCCGGTAACGCGC | 289 |
| PLAU | 211668_s_at | 1604895332856.59 | GCTCTGAAGTCACCACCAAAATGCT | 290 |
| CAV1 | 203065_s_at | 1604187716818.41 | GGTGCCAATTTCAAGTTCCAAGTTG | 291 |
| GAPDH GAPDH | AFFX-HUMGAPDH/M33197_3_at | 1601834913853.31 | TAGGGAGCCGCACCTTGTCATGTAC | 292 |
| — | 213158_at | 1597303398144.17 | ACGTATATTTACCTGTGACTTGTAT | 293 |
| ARHGEF6 | 209539_at | 1586970619512.16 | TAAACTGCTGCCCGTAGAGGCCTTT | 294 |
| PRKCB | 209685_s_at | 1580850725622.13 | TGGATGTTAGCGGTACTCTTCCACT | 295 |
| SRGN | 201859_at | 1549790579490.15 | TTTTCCTGGATATCTGTGTATTTTC | 296 |
| TLE4 | 204872_at | 1549011037374.17 | ACTGTGCGTTGTACATAGTTCTAAT | 297 |
| LOC100506558 MATN2 | 202350_s_at | 1544181853329.71 | GAACACTGGCCATAGGAAATGCTGT | 298 |
| BHLHE40 | 201170_s_at | 1537151135133.25 | GATCCTTTCTGTAGGCTAATTCCTC | 299 |
| SGCE | 204688_at | 1519398433064.38 | AACGCAGCAGAACTTGCCACATCAG | 300 |
| — | 222288_at | 1511518722955.02 | GAAGCTTGGCTTTAGTGGTAGAATG | 301 |
| PCBP2 | 204031_s_at | 1507948521040.68 | AGCCTGGCTCAATATCTAATCAATG | 302 |
| TFAP2A | 204653_at | 1493277682055.65 | GAACTTCAAACATTTGGGACCACCT | 303 |

TABLE 3-continued mRNA biomarkers of sensitivity to an sPLA2 hydrolysable, cisplatin-containing liposome. Dashes mean that the Affymetrix probeset has not been mapped to a specific gene. Affymetrix IDs refer to the array type HG-U133A.

| Gene | Affymetrix ID | Correlation | Affymetrix Probe Sequence | SEQ ID NO: |
|---|---|---|---|---|
| SPON1 | 209436_at | 1472949317341.51 | CCACCCTAGTGTCTCATGTTTGTAT | 304 |
| COL4A2 | 211966_at | 1468135692764.19 | TGGTGATGTCTGCTACTATGCCAGC | 305 |

TABLE 4 mRNA biomarkers of sensitivity to the liposome. Dashes mean that the Affymetrix probeset has not been mapped to a specific gene. Affymetrix IDs refer to the array type HG-U133A.

| Gene NO: | Affymetrix ID | Covariance | Affymetrix Probe Sequence | SEQ ID |
|---|---|---|---|---|
| KRT18 | 201596_x_at | -22426211704708.5 | AAGCTGGAGGCTGAGATCGCCACCT | 306 |
| LGALS3 | 208949_s_at | -11456296973610.8 | CACTTTAACCCACGCTTCAATGAGA | 307 |
| DSP | 200606_at | -10269594517738.5 | TGGAATGAGTCTCCTTTAGTTTCAG | 308 |
| IGFBP4 | 201508_at | -8435796702432.14 | AGAGACATGTACCTTGACCATCGTC | 309 |
| SPINT2 | 210715_s_at | -8294729535462.05 | TGGAAATCCTCTAGGAGGCTCCTCC | 310 |
| CDH1 | 201131_s_at | -7786548077136.61 | TGTGTGGGTGCTGATAATTGTGTAT | 311 |
| DSG2 | 217901_at | -7061991934030.4 | TACTCTTCCATCATCTAGAATTGTT | 312 |
| RAB25 | 218186_at | -6195270978776.59 | GCACCCTCAGGGTCTTAAGGTCTTC | 313 |
| PTPRF | 200636_s_at | -6131832886305.69 | GTACACAGTCTGTTTTCTATTTGTT | 314 |
| SOX9 | 202936_s_at | -5835576205162.92 | TGGGCTGCCTTATATTGTGTGTGTG | 315 |
| LYZ | 213975_s_at | -5458342909996.32 | TAACCCAGACTTAATCTTGAATGAT | 316 |
| IER3 | 201631_s_at | -5365171123958.73 | GAGACTTCGGCGGACCATTAGGAAT | 317 |
| PERP | 217744_s_at | -5097068499548.16 | ATGCACGTGAAACTTAACACTTTAT | 318 |
| SOX9 | 202935_s_at | -5050052756141.07 | AGTTGAACAGTGTGCCCTAGCTTTT | 319 |
| ATP1B1 | 201243_s_at | -4753436553865.35 | GATCTTGTATTCAGTCAGGTTAAAA | 320 |
| IFI27 | 202411_at | -4636709898452.9 | CCAAAGTGGTCAGGGTGGCCTCTGG | 321 |
| PHLDA2 | 209803_s_at | -4623467982538.76 | GGACGAGTCGGACCGAGGCTAGGAC | 322 |
| CTTN | 201059_at | -4563342040423.69 | ATTTGTGGCCACTCACTTTGTAGGA | 323 |
| SFN | 209260_at | -4455761701170.73 | TCTTGCTCCAAAGGGCTCCGTGGAG | 324 |
| MALL | 209373_at | -4327230558082.54 | CTCCTCCATGAGTCTGACATCTCGG | 325 |
| S100A11 | 200660_at | -4322815561525.15 | GGTTGAGGAGAGGCTCCAGACCCGC | 326 |
| TSPAN13 | 217979_at | -4261036366041.2 | ACAGCAACTTGTCAAACCTAAGCAT | 327 |
| AKR1C3 | 209160_at | -4207721689216.25 | ACGCAGAGGACGTCTCTATGCCGGT | 328 |
| FAT1 | 201579_at | -4082641838983.11 | GTAGTCATTCATTTCTAGCTGTACA | 329 |
| DSTN | 201021_s_at | -4020978397283.39 | GTAGCTGATGAAGTATGTCGCATTT | 330 |
| EFEMP1 | 201842_s_at | -3992766849062.55 | GATGATCTTCTGTGGTGCTTAAGGA | 331 |
| TFF3 | 204623_at | -3853023482644 | CTGTGATTGCTGCCAGGCACTGTTC | 332 |
| HSPB1 | 201841_s_at | -3835026328384.26 | TTCACGCGGAAATACACGCTGCCCC | 333 |
| SDC1 | 201286_at | -3731984524505.92 | TCATCTGCTGGTCCGTGGGACGGTG | 334 |

TABLE 4-continued mRNA biomarkers of sensitivity to the liposome. Dashes mean that the Affymetrix probeset has not been mapped to a specific gene. Affymetrix IDs refer to the array type HG-U1 33A.

| Gene NO: | Affymetrix ID | Covariance | Affymetrix Probe Sequence | SEQ ID |
|---|---|---|---|---|
| PLAC8 | 219014_at | -3720610591317.68 | GAAGGAGAGCCATGCGTACTTTCTA | 335 |
| TPBG | 203476_at | -3655713541808.07 | GTGTATAGTGTTTTACCCTCTTCTT | 336 |
| LCN2 | 212531_at | -3340240709988.96 | CAGGACTTTTGTTCCAGGTTGCCAG | 337 |
| CEACAM6 | 203757_s_at | -3279054777343.26 | GTGCAGTTTCTGACACTTGTTGTTG | 338 |
| ELF3 | 210827_s_at | -3241469160886.13 | GGGAGCACCGTGATGGAGAGGACAG | 339 |
| CLDN3 | 203953_s_at | -3192796314939.69 | AAGGCCAAGATCACCATCGTGGCAG | 340 |
| TPD52L1 | 203786_s_at | -3049121447681.89 | TATTCAAATGGCCCCTCCAGAAAGT | 341 |
| VAMP8 | 202546_at | -2969692217517 | AAGCCACATCTGAGCACTTCAAGAC | 342 |
| C1orf106 | 219010_at | -2931724791122.81 | GTTCCAAGAACTCTGGTGTCTGACC | 343 |
| RBM47 | 218035_s_at | -2891974033193.95 | GAGGATCATGCCCTTAGCAAGTACT | 344 |
| C3 | 217767_at | -2846605120573.62 | GGTCTACGCCTATTACAACCTGGAG | 345 |
| CAPN2 | 208683_at | -2829130992700.86 | AATCGTTCTCCTTACAATCAAGTTC | 346 |
| ERBB3 | 202454_s_at | -2788407249074.31 | GGAACTAGGCTCTTATGTGTGCCTT | 347 |
| SLPI | 203021_at | -2755718313124.09 | TCTGTCCTCCTAAGAAATCTGCCCA | 348 |
| SPATS2L | 222154_s_at | -2729322838596.83 | GAGGCTCAGTTAGCAACCTGTGTTG | 349 |
| ERBB2 | 216836_s_at | -2698032874395.93 | AGACTGTCCCTGAAACCTAGTACTG | 350 |
| SERPINB1 | 212268_at | -2694341115802.62 | ACTTTCTGCATGTTGATGCCCGAAG | 351 |
| CEACAM6 | 211657_at | -2643169692661.57 | GTTCTTGTATTGTATTGCCCAGGGG | 352 |
| AKR1B10 | 206561_s_at | -2617913243059.4 | AAAAACCGCAGCCCAGGTTCTGATC | 353 |
| ID1 | 208937_s_at | -2607302720347.48 | GACATGAACGGCTGTTACTCACGCC | 354 |
| PPAP2C | 209529_at | -2576535604785.95 | TGTTCTTGGCGCTGTATGTGCAGGC | 355 |
| AQP3 | 39248_at | -2561344001860.94 | CTTCTACAGGCTTTTGGGAAGTAGG | 356 |
| PODXL | 201578_at | -2559443301040.98 | TGGAGGACACAGATGACTCTTTGGT | 357 |
| PRR15L | 219127_at | -2483388299723.69 | GAGTGGGTGGGGAATTTTCTCCTCT | 358 |
| EMP2 | 204975_at | -2470436470609.79 | CTGCACCTTCATCAGCGGCATGATG | 359 |
| MYO10 | 201976_s_at | -2463058577194.03 | TATAAACCACTCTTCAACAGCTGGC | 360 |
| SERPINB1 | 213572_s_at | -2374385129062.88 | AATACATCCGATGCGTAGATTCTTG | 361 |
| SDC4 | 202071_at | -2371552687950.61 | TGGCTTAGCCTGGGCAGGTCGTGTC | 362 |
| CRABP2 | 202575_at | -2354608471952.81 | GAGCAGGGTCTCTCTAAAGGGGACT | 363 |
| HTATIP2 | 209448_at | -2354028532889.45 | GTCTCTGAGTTACAAAAGTGCTAAT | 364 |
| DBNDD2 SYS1 SYS1-DBNDD2 | 218094_s_at | -2352744142308.53 | ACCAGTTTTGGCTTACTCCTGAGA | 365 |
| ESRP1 | 219121_s_at | -2312028194710.22 | TTGTCTACACTCAGGCTGCAGTATT | 366 |
| HSD17B11 | 217989_at | -2304068718020.79 | TCCTGAGAGATACCTCACATTCCAA | 367 |
| GFPT1 | 202722_s_at | -2272343431090.56 | GGTTAGCCTTAGTTTCTCAGACTTG | 368 |
| S100A14 | 218677_at | -2240432231078.46 | TGTCCTCATCTCTGCAAAGTTCAGC | 369 |
| IGFBP7 | 201162_at | -2225724813680 | TTCCCAAGGACAGGCTTCAGCATCA | 370 |

TABLE 4-continued mRNA biomarkers of sensitivity to the liposome. Dashes mean that the Affymetrix probeset has not been mapped to a specific gene. Affymetrix IDs refer to the array type HG-U133A.

| Gene NO: | Affymetrix ID | Covariance | Affymetrix Probe Sequence | SEQ ID |
|---|---|---|---|---|
| PTPRF | 200637_s_at | -2190473907894.45 | CTCCTACGCAGATGCTGTCACTGGC | 371 |
| HMGA1 | 206074_s_at | -2178312788057.87 | TGAGCAAGGGGCCCGAATCGACCA | 372 |
| YWHAZ | 200641_s_at | -2145016988259.93 | AAGCCTGCTCTCTTGCAAAGACAGC | 373 |
| SCD | 200832_s_at | -2143962895648.8 | TAACTATAAGGTGCCTCAGTTTTCC | 374 |
| SH3YL1 | 204019_s_at | -2139236372988.65 | CATATGGCATCTCTCAACTTTTCTT | 375 |
| UCP2 | 208998_at | -2139031352031.13 | GAAAGTTCAGCCAGAATCTTCGTCC | 376 |
| F3 | 204363_at | -2113802654784.93 | GGGCAGCTTCCTAATATGCTTTACA | 377 |
| AZGP1 | 209309_at | -2089576575474.55 | GCCTGTCTTGAGTAGACTTGGACCC | 378 |
| LIMCH1 | 212327_at | -2089195209441.08 | GATCCACCTCATATGTGAGTCCGTC | 379 |
| PLA2G2A | 203649_s_at | -2069037053701.26 | CGCTGCTGTGTCACTCATGACTGTT | 380 |
| ITGB5 | 201125_s_at | -2028321449243.62 | GCCTGTTGAAGGTACATCGTTTGCA | 381 |
| ABCC3 | 208161_s_at | -2007168680009.07 | TCTCCCGATTCCCAACTGAGTGTTA | 382 |
| DDR1 MIR4640 | 207169_x_at | -2000582844983.07 | AGGCAATTTTAATCCCCTGCACTAG | 383 |
| GATA3 | 209604_s_at | -1995114130212.84 | GGACAAACTGCCAGTTTTGTTTCCT | 384 |
| CYB561 | 209163_at | -1981172434786.63 | GTTCTTCAATCAGCTGGCACACACT | 385 |
| C10orf116 | 203571_s_at | -1962923571527.29 | ACCACCCAGGAAACCATCGACAAGA | 386 |
| PTPRF | 200635_s_at | -1924144465806.05 | AAGGACAGAACATTGCCTTCCTCGT | 387 |
| DKK1 | 204602_at | -1893211415469.31 | GGATATACAAGTTCTGTGGTTTCAG | 388 |
| SERPINB5 | 204855_at | -1863934443254.52 | GTGGTTGGCACTAGACTGGTGGCAG | 389 |
| ARHGAP29 | 203910_at | -1818117319379.63 | ATGTACTTGTTCTACCTGGATTGTC | 390 |
| GAS6 | 202177_at | -1817533234900.07 | CGCGGCTGCATGACACTGGAGGTCA | 391 |
| LAMB3 | 209270_at | -1817170377879.96 | GGTGCCCGGATCCAGAGTGTGAAGA | 392 |
| KLF5 | 209212_s_at | -1814910338390.4 | CTCCATCCTATGCTGCTACAATTGC | 393 |
| MAOA | 212741_at | -1811716715860.48 | TGAATGCCAGTCCAGATGTGCCTAG | 394 |
| NET1 | 201830_s_at | -1789348130490.25 | TTACATTCATTTAACCTGCCGATTA | 395 |
| CYBA | 203028_s_at | -1775049034494.02 | CACCCAGTGGTACTTTGGTGCCTAC | 396 |
| TGM2 | 201042_at | -1772139742186.19 | AGTGCTGGTCACTAACCAACAAGGT | 397 |
| ALDH2 | 201425_at | -1757839520621.92 | CTCTCTGAAACGCTTCCTATAACTC | 398 |
| HSPA1A HSPA1B | 200799_at | -1730673434053.48 | TTGTCAGTTCTCAATTTCCTGTGTT | 399 |
| JUP | 201015_s_at | -1729139912998.84 | ATTATCGCTTTATGTTTTTGGTTAT | 400 |
| HSPA1A HSPA1B | 200800_s_at | -1722098969341.57 | GGGGCTCAAGGGCAAGATCAGCGAG | 401 |
| F11R | 221664_s_at | -1642391094616.93 | GAATAGGTATCTTGAGCTTGGTTCT | 402 |

TABLE 4-continued mRNA biomarkers of sensitivity to the liposome. Dashes mean that the Affymetrix probeset has not been mapped to a specific gene. Affymetrix IDs refer to the array type HG-U1 33A.

| Gene NO: | Affymetrix ID | Covariance | Affymetrix Probe Sequence | SEQ ID |
|---|---|---|---|---|
| HBG1 HBG2 LOC100653006 LOC100653319 | 204419_x_at | -1595966820539.76 | ACACTCGCTTCTGGAACGTCTGAGG | 403 |
| KLF4 | 221841_s_at | -1553919884310.19 | AATCTATATTTGTCTTCCGATCAAC | 404 |
| CA12 | 214164_x_at | -1551710888005.42 | ACAAGGCCCAGGCTGGGGCCAGGGC | 405 |

The biomarker COL5A2 (SEQ ID NO 73 or 211) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker COL5A2 (SEQ ID NO 73 or 211) may be assessed using nucleic acid amplification methods (e.g., PCR, such as qRT-PCR) or a device (e.g., a microarray). As is described above, the level of COL5A2 (SEQ ID NO 73 or 211) in the patient sample may then be compared, e.g., to the level of COL5A2 (SEQ ID NO 73 or 211) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker COL5A2 (SEQ ID NO 73 or 211) may be used as the sole biomarker to predict cancer patient responsiveness to treatment with the liposome or in combination with one or more additional biomarkers (e.g., one, two, three, four, five, ten, or all of the biomarkers shown in Tables 1-4), such as ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker COL5A2 (SEQ ID NO 73 or 211). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker ITGA4 (SEQ ID NO: 1) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker ITGA4 (SEQ ID NO: 1) may be assessed using nucleic acid amplification methods (e.g., PCR, such as qRT-PCR) or a device (e.g., a microarray). As is described above, the level of ITGA4 (SEQ ID NO: 1) in the patient sample may then be compared, e.g., to the level of ITGA4 (SEQ ID NO: 1) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker ITGA4 (SEQ ID NO: 1) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker ITGA4 (SEQ ID NO: 1). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker MSN (SEQ ID NO: 2) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker MSN (SEQ ID NO: 2) may be assessed using nucleic acid amplification methods (e.g., PCR, such as qRT-PCR) or a device (e.g., a microarray). As is described above, the level of MSN (SEQ ID NO: 2) in the patient sample may then be compared, e.g., to the level of MSN (SEQ ID NO: 2) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker MSN (SEQ ID NO: 2) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker MSN (SEQ ID NO: 2). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker FAM46A (SEQ ID NO: 3 or 280) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker FAM46A (SEQ ID NO: 3 or 280) may be assessed using nucleic acid amplification methods (e.g., PCR, such as qRT-PCR) or a device (e.g., a microarray). As is described above, the level of FAM46A (SEQ ID NO: 3 or 280) in the patient sample may then be compared, e.g., to the level of FAM46A (SEQ ID NO: 3 or 280) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker FAM46A (SEQ ID NO: 3 or 280) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO:

100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker FAM46A (SEQ ID NO: 3 or 280). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker ITGB2 (SEQ ID NO: 4) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker ITGB2 (SEQ ID NO: 4) may be assessed using nucleic acid amplification methods (e.g., PCR, such as qRT-PCR) or a device (e.g., a microarray). As is described above, the level of ITGB2 (SEQ ID NO: 4) in the patient sample may then be compared, e.g., to the level of ITGB2 (SEQ ID NO: 4) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker ITGB2 (SEQ ID NO: 4) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker ITGB2 (SEQ ID NO: 4). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker DOCK2 (SEQ ID NO: 5 or 223) may be used to assess a cancer patient's (e.g, a patient having cancer that is resistant to one or more cancer, such as one or more cancer therapies other than an sPLA$_2$ hydrolysable, cisplatin-containing liposome) responsiveness to an sPLA$_2$ hydrolysable, cisplatin-containing liposome. The level of the biomarker DOCK2 (SEQ ID NO: 5 or 223) may be assessed using nucleic acid amplification methods (e.g., PCR, such as qRT-PCR) or a device (e.g., a microarray). As is described above, the level of DOCK2 (SEQ ID NO: 5 or 223) in the patient sample may then be compared, e.g., to the level of DOCK2 (SEQ ID NO: 5 or 223) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker DOCK2 (SEQ ID NO: 5 or 223) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO:

100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker DOCK2 (SEQ ID NO: 5 or 223). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker EVL (SEQ ID NO: 6) may be used to assess a cancer patient's (e.g., a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker EVL (SEQ ID NO: 6) may be assessed using nucleic acid amplification methods (e.g., PCR, such as qRT-PCR) or a device (e.g., a microarray). As is described above, the level of EVL (SEQ ID NO: 6) in the patient sample may then be compared, e.g., to the level of EVL (SEQ ID NO: 6) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker EVL (SEQ ID NO: 6) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker EVL (SEQ ID NO: 6). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SACS (SEQ ID NO: 7) may be used to assess a cancer patient's (e.g., a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker SACS (SEQ ID NO: 7) may be assessed using nucleic acid amplification methods (e.g., PCR, such as qRT-PCR) or a device (e.g., a microarray). As is described above, the level of SACS (SEQ ID NO: 7) in the patient sample may then be compared, e.g., to the level of SACS (SEQ ID NO: 7) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SACS (SEQ ID NO: 7) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SACS (SEQ ID NO: 7). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker PTPRCAP (SEQ ID NO: 8) may be used to assess a cancer patient's (e.g., a patient having cancer that is resistant to one or more cancer therapies, such as one or more cancer therapies other than an sPLA$_2$ hydrolysable, cisplatin-containing liposome) responsiveness to the liposome. The level of the biomarker PTPRCAP (SEQ ID NO: 8) may be assessed using nucleic acid amplification methods (e.g., PCR, such as qRT-PCR) or a device (e.g., a microarray). As is described above, the level of PTPRCAP (SEQ ID NO: 8) in the patient sample may then be compared, e.g., to the level of PTPRCAP (SEQ ID NO: 8) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker PTPRCAP (SEQ ID NO: 8) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker PTPRCAP (SEQ ID NO: 8). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker EBI2 (SEQ ID NO: 9) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker EBI2 (SEQ ID NO: 9) may be assessed using nucleic acid amplification methods (e.g., PCR, such as qRT-PCR) or a device (e.g., a microarray). As is described above, the level of EBI2 (SEQ ID NO: 9) in the patient sample may then be compared, e.g., to the level of EBI2 (SEQ ID NO: 9) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker EBI2 (SEQ ID NO: 9) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker EBI2 (SEQ ID NO: 9). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker PTPRC (SEQ ID NO: 10, 18, 25, or 243) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker PTPRC (SEQ ID NO: 10, 18, 25, or 243) may be assessed using nucleic acid amplification methods (e.g., PCR, such as qRT-PCR) or a device (e.g., a microarray). As is described above, the level of PTPRC (SEQ ID NO: 10, 18, 25, or 243) in the patient sample may then be compared, e.g., to the level of PTPRC (SEQ ID NO: 10, 18, 25, or 243) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker PTPRC (SEQ ID NO: 10, 18, 25, or 243) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker PTPRC (SEQ ID NO: 10, 18, 25, or 243). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker ANP32E (SEQ ID NO: 11) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker ANP32E (SEQ ID NO: 11) may be assessed using nucleic acid amplification methods (e.g., PCR, such as qRT-PCR) or a device (e.g., a microarray). As is described above, the level of ANP32E (SEQ ID NO: 11) in the patient sample may then be compared, e.g., to the level of ANP32E (SEQ ID NO: 11) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker ANP32E (SEQ ID NO: 11) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker ANP32E (SEQ ID NO: 11). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SFPQ (SEQ ID NO: 12, 38 or 272) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker SFPQ (SEQ ID NO: 12, 38 or 272) may be assessed using nucleic acid amplification methods (e.g., PCR, such as qRT-PCR) or a device (e.g., a microarray). As is described above, the level of SFPQ (SEQ ID NO: 12, 38 or 272) in the patient sample may then be compared, e.g., to the level of SFPQ (SEQ ID NO: 12, 38 or 272) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SFPQ (SEQ ID NO: 12, 38 or 272) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SFPQ (SEQ ID NO: 12, 38 or 272). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker C1QR1 (SEQ ID NO: 13) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker C1QR1 (SEQ ID NO: 13) may be assessed using nucleic acid amplification methods (e.g., PCR, such as qRT-PCR) or a device (e.g., a microarray). As is described above, the level of C1QR1 (SEQ ID NO: 13) in the patient sample may then be compared, e.g., to the level of C1QR1 (SEQ ID NO: 13) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker C1QR1 (SEQ ID NO: 13) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker C1QR1 (SEQ ID NO: 13). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker FNBP1 (SEQ ID NO: 14 or 28) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker FNBP1 (SEQ ID NO: 14 or 28) may be assessed using nucleic acid amplification methods (e.g., PCR, such as qRT-PCR) or a device (e.g., a microarray). As is described above, the level of FNBP1 (SEQ ID NO: 14 or 28) in the patient sample may then be compared, e.g., to the level of FNBP1 (SEQ ID NO: 14 or 28) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker FNBP1 (SEQ ID NO: 14 or 28) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker FNBP1 (SEQ ID NO: 14 or 28). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SFN (SEQ ID NO: 96 or 324) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker SFN (SEQ ID NO: 96 or 324) may be assessed using nucleic acid amplification methods (e.g., PCR, such as qRT-PCR) or a device (e.g., a microarray). As is described above, the level of SFN (SEQ ID NO: 96 or 324) in the patient sample may then be compared, e.g., to the level of SFN (SEQ ID NO: 96 or 324) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SFN (SEQ ID NO: 96 or 324) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SFN (SEQ ID NO: 96 or 324). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker LISCH7 (SEQ ID NO: 97) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker LISCH7 (SEQ ID NO: 97) may be assessed using nucleic acid amplification methods (e.g., PCR, such as qRT-PCR) or a device (e.g., a microarray). As is described above, the level of LISCH7 (SEQ ID NO: 97) in the patient sample may then be compared, e.g., to the level of LISCH7 (SEQ ID NO: 97) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker LISCH7 (SEQ ID NO: 97) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker LISCH7 (SEQ ID NO: 97). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker EPB41 L4B (SEQ ID NO: 98) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker EPB41 L4B (SEQ ID NO: 98) may be assessed using nucleic acid amplification methods (e.g., PCR, such as qRT-PCR) or a device (e.g., a microarray). As is described above, the level of EPB41 L4B (SEQ ID NO: 98) in the patient sample may then be compared, e.g., to the level of EPB41 L4B (SEQ ID NO: 98) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker EPB41 L4B (SEQ ID NO: 98) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker EPB41 L4B (SEQ ID NO: 98). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker MST1R (SEQ ID NO: 99) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker MST1R (SEQ ID NO: 99) may be assessed using nucleic acid amplification methods (e.g., PCR, such as qRT-PCR) or a device (e.g., a microarray). As is described above, the level of MST1R (SEQ ID NO: 99) in the patient sample may then be compared, e.g., to the level of MST1R (SEQ ID NO: 99) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker MST1R (SEQ ID NO: 99) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker MST1R (SEQ ID NO: 99). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker ITGB4 (SEQ ID NO: 100) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker ITGB4 (SEQ ID NO: 100) may be assessed using nucleic acid amplification methods (e.g., PCR, such as qRT-PCR) or a device (e.g., a microarray). As is described above, the level of ITGB4 (SEQ ID NO: 100) in the patient sample may then be compared, e.g., to the level of ITGB4 (SEQ ID NO: 100) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker ITGB4 (SEQ ID NO: 100) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker ITGB4 (SEQ ID NO: 100). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker DBNDD2 (SEQ ID NO: 102 or 365) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker DBNDD2 (SEQ ID NO: 102 or 365) may be assessed using nucleic acid amplification methods (e.g., PCR, such as qRT-PCR) or a device (e.g., a microarray). As is described above, the level of DBNDD2 (SEQ ID NO: 102 or 365) in the patient sample may then be compared, e.g., to the level of DBNDD2 (SEQ ID NO: 102 or 365) in a cell (e.g., a cancer cell) or tissue (e.g., a tumor tissue) known to be sensitive or resistant to treatment with the liposome and, which can be used as a reference to determine the cancer patient's responsiveness to the liposome.

The biomarker DBNDD2 (SEQ ID NO: 102 or 365) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker DBNDD2 (SEQ ID NO: 102 or 365). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker TACSTD1 (SEQ ID NO: 104) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker TACSTD1 (SEQ ID NO: 104) may be assessed using nucleic acid amplification methods (e.g., PCR, such as qRT-PCR) or a device (e.g., a microarray). As is described above, the level of TACSTD1 (SEQ ID NO: 104) in the patient sample may then be compared, e.g., to the level of TACSTD1 (SEQ ID NO: 104) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker TACSTD1 (SEQ ID NO: 104) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker TACSTD1 (SEQ ID NO: 104). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker MISP (SEQ ID NO: 105) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker MISP (SEQ ID NO: 105) may be assessed using nucleic acid amplification methods (e.g., PCR, such as qRT-PCR) or a device (e.g., a microarray). As is described above, the level of MISP (SEQ ID NO: 105) in the patient sample may then be compared, e.g., to the level of MISP (SEQ ID NO: 105) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker MISP (SEQ ID NO: 105) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker MISP (SEQ ID NO: 105). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker KRT8 (SEQ ID NO: 106) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker KRT8 (SEQ ID NO: 106 (SEQ ID NO: 314 or 386) may be assessed using nucleic acid amplification methods (e.g., PCR, such as qRT-PCR) or a device (e.g., a microarray). As is described above, the level of KRT8 (SEQ ID NO: 106) in the patient sample may then be compared, e.g., to the level of KRT8 (SEQ ID NO: 106) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker KRT8 (SEQ ID NO: 106) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker KRT8 (SEQ ID NO: 106). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome The biomarker JUP (SEQ ID NO: 107 or 400) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA$_2$ hydrolysable, cisplatin-containing liposome. The level of the biomarker JUP (SEQ ID NO: 107 or 400) may be assessed using nucleic acid amplification methods (e.g., PCR, such as qRT-PCR) or a device (e.g., a microarray). As is described above, the level of JUP (SEQ ID NO: 107 or 400) in the patient sample may then be compared, e.g., to the level of JUP (SEQ ID NO: 107 or 400) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker JUP (SEQ ID NO: 107 or 400) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker JUP (SEQ ID NO: 107 or 400). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker KRT18 (SEQ ID NO: 108 or 306) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker KRT18 (SEQ ID NO: 108 or 306) may be assessed using nucleic acid amplification methods (e.g., PCR, such as qRT-PCR) or a device (e.g., a microarray). As is described above, the level of KRT18 (SEQ ID NO: 108 or 306) in the patient sample may then be compared, e.g., to the level of KRT18 (SEQ ID NO: 108 or 306) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker KRT18 (SEQ ID NO: 108 or 306) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO:

7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker KRT18 (SEQ ID NO: 108 or 306). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker FA2H (SEQ ID NO: 109) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker FA2H (SEQ ID NO: 109) may be assessed using nucleic acid amplification methods (e.g., PCR, such as qRT-PCR) or a device (e.g., a microarray). As is described above, the level of FA2H (SEQ ID NO: 109) in the patient sample may then be compared, e.g., to the level of FA2H (SEQ ID NO: 109) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker FA2H (SEQ ID NO: 109) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker FA2H (SEQ ID NO: 109). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker MGAT4B (SEQ ID NO: 110) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker MGAT4B (SEQ ID NO: 110) may be assessed using nucleic acid amplification methods (e.g., PCR, such as qRT-PCR) or a device (e.g., a microarray). As is described above, the level of MGAT4B (SEQ ID NO: 110) in the patient sample may then be compared, e.g., to the level of MGAT4B (SEQ ID NO: 110) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker MGAT4B (SEQ ID NO: 110) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker MGAT4B (SEQ ID NO: 110). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker DSG2 (SEQ ID NO: 111 or 312) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker DSG2 (SEQ ID NO: 111 or 312) may be assessed using nucleic acid amplification methods (e.g., PCR, such as qRT-PCR) or a device (e.g., a microarray). As is described above, the level of DSG2 (SEQ ID NO: 111 or 312) in the patient sample may then be compared, e.g., to the level of DSG2 (SEQ ID NO: 111 or 312) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker DSG2 (SEQ ID NO:111 or 312) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker COL5A2 (SEQ ID NO 73 or 211). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker LRP5 (SEQ ID NO: 112) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker LRP5 (SEQ ID NO: 112) may be assessed using nucleic acid amplification methods (e.g., PCR, such as qRT-PCR) or a device (e.g., a microarray). As is described above, the level of LRP5 (SEQ ID NO: 112) in the patient sample may then be compared, e.g., to the level of LRP5 (SEQ ID NO: 112) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker LRP5 (SEQ ID NO: 112) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker LRP5 (SEQ ID NO: 112). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SFRS7 (SEQ ID NO: 19 or 54) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker SFRS7 (SEQ ID NO: 19 or 54) may be assessed using nucleic acid amplification methods (e.g., PCR, such as qRT-PCR) or a device (e.g., a microarray). As is described above, the level of SFRS7 (SEQ ID NO: 19 or 54) in the patient sample may then be compared, e.g., to the level of SFRS7 (SEQ ID NO: 19 or 54) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SFRS7 (SEQ ID NO: 19 or 54) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SFRS7 (SEQ ID NO: 19 or 54). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker CAP350 (SEQ ID NO: 20 or 61) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker CAP350 (SEQ ID NO: 20 or 61) may be assessed using nucleic acid amplification methods (e.g., PCR, such as qRT-PCR) or a device (e.g., a microarray). As is described above, the level of CAP350 (SEQ ID NO: 20 or 61) in the patient sample may then be compared, e.g., to the level of CAP350 (SEQ ID NO: 20 or 61) in a cell (e.g., a cancer cell) or tissue (e.g., a tumor tissue) known to be sensitive or resistant to treatment with the liposome, which can be used as a reference to determine the cancer patient's responsiveness to the liposome.

The biomarker CAP350 (SEQ ID NO: 20 or 61) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker CAP350 (SEQ ID NO: 20 or 61). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker CALD1 (SEQ ID NO: 206) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The expression level of the biomarker CALD1 (SEQ ID NO: 206) may be assessed using nucleic acid amplification methods (e.g., PCR, such as qRT-PCR) or a device (e.g., a microarray). As is described above, the expression level of CALD1 (SEQ ID NO: 206) in the patient sample may then be compared, e.g., to the expression level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker CALD1 (SEQ ID NO: 206) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker CALD1 (SEQ ID NO: 206). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker COL6A2 (SEQ ID NO: 207) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The expression level of the biomarker COL6A2 (SEQ ID NO: 207) may be assessed using nucleic acid amplification methods (e.g., PCR, such as qRT-PCR) or a device (e.g., a microarray). As is described above, the expression level of COL6A2 (SEQ ID NO: 207) in the patient sample may then be compared, e.g., to the expression level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker COL6A2 (SEQ ID NO: 207) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker COL6A2 (SEQ ID NO: 207). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker FERMT2 (SEQ ID NO: 208) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker FERMT2 (SEQ ID NO: 208) may be assessed using nucleic acid amplification methods (e.g., PCR, such as qRT-PCR) or a device (e.g., a microarray). As is described above, the level of FERMT2 (SEQ ID NO: 208) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker FERMT2 (SEQ ID NO: 208) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker FERMT2 (SEQ ID NO: 208). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker BNIP3 (SEQ ID NO: 209 or 263) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker BNIP3 (SEQ ID NO: 209 or 263) may be assessed using nucleic acid amplification methods (e.g., PCR, such as qRT-PCR) or a device (e.g., a microarray). As is described above, the level of BNIP3 (SEQ ID NO: 209 or 263) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker BNIP3 (SEQ ID NO: 209 or 263) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker BNIP3 (SEQ ID NO: 209 or 263). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker RAB31 (SEQ ID NO: 210) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker RAB31 (SEQ ID NO: 210) may be assessed using nucleic acid amplification methods (e.g., PCR, such as qRT-PCR) or a device (e.g., a microarray). As is described above, the level of RAB31 (SEQ ID NO: 210) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker RAB31 (SEQ ID NO: 210) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker RAB31 (SEQ ID NO: 210). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker MPO (SEQ ID NO: 212) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker MPO (SEQ ID NO: 212) may be assessed using nucleic acid amplification methods (e.g., PCR, such as qRT-PCR) or a device (e.g., a microarray). As is described above, the level of MPO (SEQ ID NO: 212) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker MPO (SEQ ID NO: 212) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker MPO (SEQ ID NO: 212). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SRPX (SEQ ID NO: 213) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker SRPX (SEQ ID NO: 213) may be assessed using nucleic acid amplification methods (e.g., PCR, such as qRT-PCR) or a device (e.g., a microarray). As is described above, the level of SRPX (SEQ ID NO: 213) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SRPX (SEQ ID NO: 213) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SRPX (SEQ ID NO: 213). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker ARHGDIB (SEQ ID NO: 214) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker ARHGDIB (SEQ ID NO: 214) may be assessed using nucleic acid amplification methods (e.g., PCR, such as qRT-PCR) or a device (e.g., a microarray). As is described above, the level of ARHGDIB (SEQ ID NO: 214) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker ARHGDIB (SEQ ID NO: 214) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker ARHGDIB (SEQ ID NO: 214). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker TMEM47 (SEQ ID NO: 215) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker TMEM47 (SEQ ID NO: 215) may be assessed using nucleic acid amplification methods (e.g., PCR, such as qRT-PCR) or a device (e.g., a microarray). As is described above, the level of TMEM47 (SEQ ID NO: 215) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker TMEM47 (SEQ ID NO: 215) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker TMEM47 (SEQ ID NO: 215). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker CSRP2 (SEQ ID NO: 216) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker CSRP2 (SEQ ID NO: 216) may be assessed using nucleic acid amplification methods (e.g., PCR, such as qRT-PCR) or a device (e.g., a microarray). As is described above, the level of CSRP2 (SEQ ID NO: 216) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker CSRP2 (SEQ ID NO: 216) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker CSRP2 (SEQ ID NO: 216). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker DPYSL3 (SEQ ID NO: 217) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker DPYSL3 (SEQ ID NO: 217) may be assessed using nucleic acid amplification methods (e.g., PCR, such as qRT-PCR) or a device (e.g., a microarray). As is described above, the level of DPYSL3 (SEQ ID NO: 217) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker DPYSL3 (SEQ ID NO: 217) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker DPYSL3 (SEQ ID NO: 217). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker HTRA1 (SEQ ID NO: 218) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker HTRA1 (SEQ ID NO: 218) may be assessed using nucleic acid amplification methods (e.g., PCR, such as qRT-PCR) or a device (e.g., a microarray). As is described above, the level of HTRA1 (SEQ ID NO: 218) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker HTRA1 (SEQ ID NO: 218) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker HTRA1 (SEQ ID NO: 218). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SLC39A6 (SEQ ID NO: 219) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker SLC39A6 (SEQ ID NO: 219) may be assessed using nucleic acid amplification methods (e.g., PCR, such as qRT-PCR) or a device (e.g., a microarray). As is described above, the level of SLC39A6 (SEQ ID NO: 219) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SLC39A6 (SEQ ID NO: 219) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SLC39A6 (SEQ ID NO: 219). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker LAT2 (SEQ ID NO: 220) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker LAT2 (SEQ ID NO: 220) may be assessed using nucleic acid amplification methods (e.g., PCR, such as qRT-PCR) or a device (e.g., a microarray). As is described above, the level of LAT2 (SEQ ID NO: 220) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker LAT2 (SEQ ID NO: 220) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker LAT2 (SEQ ID NO: 220). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker LGALS3 (SEQ ID NO: 307) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker LGALS3 (SEQ ID NO: 307) may be assessed using nucleic acid amplification methods (e.g., PCR, such as qRT-PCR) or a device (e.g., a microarray). As is described above, the level of LGALS3 (SEQ ID NO: 307) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker LGALS3 (SEQ ID NO: 307) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker LGALS3 (SEQ ID NO: 307). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker IGFBP4 (SEQ ID NO: 309) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker IGFBP4 (SEQ ID NO: 309) may be assessed using nucleic acid amplification methods (e.g., PCR, such as qRT-PCR) or a device (e.g., a microarray). As is described above, the level of IGFBP4 (SEQ ID NO: 309) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker IGFBP4 (SEQ ID NO: 309) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker IGFBP4 (SEQ ID NO: 309). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SPINT2 (SEQ ID NO: 310) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker SPINT2 (SEQ ID NO: 310) may be assessed using nucleic acid amplification methods (e.g., PCR, such as qRT-PCR) or a device (e.g., a microarray). As is described above, the level of SPINT2 (SEQ ID NO: 310) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SPINT2 (SEQ ID NO: 310) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SPINT2 (SEQ ID NO: 310). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker CDH1 (SEQ ID NO: 311) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker CDH1 (SEQ ID NO: 311) may be assessed using nucleic acid amplification methods (e.g., PCR, such as qRT-PCR) or a device (e.g., a microarray). As is described above, the level of CDH1 (SEQ ID NO: 311) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker CDH1 (SEQ ID NO: 311) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker CDH1 (SEQ ID NO: 311). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker RAB25 (SEQ ID NO: 313) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker RAB25 (SEQ ID NO: 313) may be assessed using nucleic acid amplification methods (e.g., PCR, such as qRT-PCR) or a device (e.g., a microarray). As is described above, the level of RAB25 (SEQ ID NO: 313) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker RAB25 (SEQ ID NO: 313) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker RAB25 (SEQ ID NO: 313). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker TMEM47 (SEQ ID NO: 215) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker TMEM47 (SEQ ID NO: 215) may be assessed using nucleic acid amplification methods (e.g., PCR, such as qRT-PCR) or a device (e.g., a microarray). As is described above, the level of TMEM47 (SEQ ID NO: 215) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker TMEM47 (SEQ ID NO: 215) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), CSRP2 (SEQ ID NO: 216), TMEM47 (SEQ ID NO: 215), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker TMEM47 (SEQ ID NO: 215). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker CSRP2 (SEQ ID NO: 216) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker CSRP2 (SEQ ID NO: 216) may be assessed using nucleic acid amplification methods (e.g., PCR, such as qRT-PCR) or a device (e.g., a microarray). As is described above, the level of CSRP2 (SEQ ID NO: 216) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker CSRP2 (SEQ ID NO: 216) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker CSRP2 (SEQ ID NO: 216). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker DPYSL3 (SEQ ID NO: 217) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker DPYSL3 (SEQ ID NO: 217) may be assessed using nucleic acid amplification methods (e.g., PCR, such as qRT-PCR) or a device (e.g., a microarray). As is described above, the level of DPYSL3 (SEQ ID NO: 217) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker DPYSL3 (SEQ ID NO: 217) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker DPYSL3 (SEQ ID NO: 217). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker HTRA1 (SEQ ID NO: 218) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker HTRA1 (SEQ ID NO: 218) may be assessed using nucleic acid amplification methods (e.g., PCR, such as qRT-PCR) or a device (e.g., a microarray). As is described above, the level of HTRA1 (SEQ ID NO: 218) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker HTRA1 (SEQ ID NO: 218) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker HTRA1 (SEQ ID NO: 218). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SLC39A6 (SEQ ID NO: 219) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker SLC39A6 (SEQ ID NO: 219) may be assessed using nucleic acid amplification methods (e.g., PCR, such as qRT-PCR) or a device (e.g., a microarray). As is described above, the level of SLC39A6 (SEQ ID NO: 219) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SLC39A6 (SEQ ID NO: 219) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SLC39A6 (SEQ ID NO: 219). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker LAT2 (SEQ ID NO: 220) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker LAT2 (SEQ ID NO: 220) may be assessed using nucleic acid amplification methods (e.g., PCR, such as qRT-PCR) or a device (e.g., a microarray). As is described above, the level of LAT2 (SEQ ID NO: 220) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker LAT2 (SEQ ID NO: 220) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker LAT2 (SEQ ID NO: 220). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker LGALS3 (SEQ ID NO: 307) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker LGALS3 (SEQ ID NO: 307) may be assessed using nucleic acid amplification methods (e.g., PCR, such as qRT-PCR) or a device (e.g., a microarray). As is described above, the level of LGALS3 (SEQ ID NO: 307) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker LGALS3 (SEQ ID NO: 307) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker LGALS3 (SEQ ID NO: 307). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker DSP (SEQ ID NO: 308) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker DSP (SEQ ID NO: 308) may be assessed using nucleic acid amplification methods (e.g., PCR, such as qRT-PCR) or a device (e.g., a microarray). As is described above, the level of DSP (SEQ ID NO: 308) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker DSP (SEQ ID NO: 308) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker DSP (SEQ ID NO: 308). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker IGFBP4 (SEQ ID NO: 309) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker IGFBP4 (SEQ ID NO: 309) may be assessed using nucleic acid amplification methods (e.g., PCR, such as qRT-PCR)) or a device (e.g., a microarray). As is described above, the level of IGFBP4 (SEQ ID NO: 309) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker IGFBP4 (SEQ ID NO: 309) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker IGFBP4 (SEQ ID NO: 309). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SPINT2 (SEQ ID NO: 310) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker SPINT2 (SEQ ID NO: 310) may be assessed using nucleic acid amplification methods (e.g., PCR, such as qRT-PCR) or a device (e.g., a microarray). As is described above, the level of SPINT2 (SEQ ID NO: 310) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SPINT2 (SEQ ID NO: 310) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SPINT2 (SEQ ID NO: 310). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker CDH1 (SEQ ID NO: 311) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker CDH1 (SEQ ID NO: 311) may be assessed using nucleic acid amplification methods (e.g., PCR, such as qRT-PCR) or a device (e.g., a microarray). As is described above, the level of CDH1 (SEQ ID NO: 311) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker CDH1 (SEQ ID NO: 311) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker CDH1 (SEQ ID NO: 311). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker PTPRF (SEQ ID NO: 314, 371, or 387) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker PTPRF (SEQ ID NO: 314, 371, or 387) may be assessed using nucleic acid amplification methods (e.g., PCR, such as qRT-PCR) or a device (e.g., a microarray). As is described above, the level of PTPRF (SEQ ID NO: 314, 371, or 387) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker PTPRF (SEQ ID NO: 314, 371, or 387) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker PTPRF (SEQ ID NO: 314, 371, or 387). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker SOX9 (SEQ ID NO: 121, 315, or 319) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker SOX9 (SEQ ID NO: 121, 315, or 319) may be assessed using nucleic acid amplification methods (e.g., PCR, such as qRT-PCR) or a device (e.g., a microarray). As is described above, the level of SOX9 (SEQ ID NO: 121, 315, or 319) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker SOX9 (SEQ ID NO: 121, 315, or 319) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), LYZ (SEQ ID NO: 316), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker SOX9 (SEQ ID NO: 121, 315, or 319). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker LYZ (SEQ ID NO: 316) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The expression level of the biomarker LYZ (SEQ ID NO: 316) may be assessed using nucleic acid amplification methods (e.g., PCR, such as qRT-PCR) or a device (e.g., a microarray). As is described above, the expression level of LYZ (SEQ ID NO: 316) in the patient sample may then be compared, e.g., to the expression level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker LYZ (SEQ ID NO: 316) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), IER3 (SEQ ID NO: 127 or 317), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker LYZ (SEQ ID NO: 316). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker IER3 (SEQ ID NO: 127 or 317) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker IER3 (SEQ ID NO: 127 or 317) may be assessed using nucleic acid amplification methods (e.g., PCR, such as qRT-PCR) or a device (e.g., a microarray). As is described above, the level of IER3 (SEQ ID NO: 127 or 317) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker IER3 (SEQ ID NO: 127 or 317) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), PERP (SEQ ID NO: 318), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker IER3 (SEQ ID NO: 127 or 317). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker PERP (SEQ ID NO: 318) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker PERP (SEQ ID NO: 318) may be assessed using nucleic acid amplification methods (e.g., PCR, such as qRT-PCR) or a device (e.g., a microarray). As is described above, the level of PERP (SEQ ID NO: 318) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker PERP (SEQ ID NO: 318) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), ATP1B1 (SEQ ID NO: 320), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker PERP (SEQ ID NO: 318). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker ATP1B1 (SEQ ID NO: 320) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker ATP1B1 (SEQ ID NO: 320) may be assessed using nucleic acid amplification methods (e.g., PCR, such as qRT-PCR) or a device (e.g., a microarray). As is described above, the level of ATP1B1 (SEQ ID NO: 320) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker ATP1B1 (SEQ ID NO: 320) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), or IFI27 (SEQ ID NO: 321). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker ATP1B1 (SEQ ID NO: 320). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

The biomarker IFI27 (SEQ ID NO: 321) may be used to assess a cancer patient's (e.g, a patient having cancer that is resistant to one or more cancer therapies, such as one or more cancer therapies other than an sPLA$_2$ hydrolysable, cisplatin-containing liposome) responsiveness to an sPLA2 hydrolysable, cisplatin-containing liposome. The level of the biomarker IFI27 (SEQ ID NO: 321) may be assessed using nucleic acid amplification methods (e.g., PCR, such as qRT-PCR) or a device (e.g., a microarray). As is described above, the level of IFI27 (SEQ ID NO: 321) in the patient sample may then be compared, e.g., to the level of in a cell (e.g., a cancer cell) or tissue (e.g., a tumor tissue) known to be sensitive or resistant to treatment with the liposome, which can be used as a reference to determine the cancer patient's responsiveness to the liposome.

The biomarker IFI27 (SEQ ID NO: 321) may be used as the sole biomarker to predict cancer patient responsiveness to treatment with the liposome or in combination with one or more additional biomarkers (e.g., one, two, three, four, five, ten, or all of the biomarkers shown in Tables 1-4), such as COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38 or 272), C1QR1 (SEQ ID NO: 13), FNBP1 (SEQ ID NO: 14 or 28), CBFB (SEQ ID NO: 15), SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), RAB25 (SEQ ID NO: 313), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), LAT2 (SEQ ID NO: 220), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), or ATP1B1 (SEQ ID NO: 320). The level of the biomarker(s) may be determined using, e.g., a microarray, PCR, or other techniques described herein, for example, using a nucleic acid probe sequence based on the target sequences shown in Tables 1-4. Optionally, the level of PLA2G2A (SEQ ID NO: 380) or sPLA$_2$ may be detected in a tumor sample from the patient and used to determine the cancer patient's responsiveness to the liposome in combination with the biomarker IFI27 (SEQ ID NO: 321). In particular, the patient is determined to be responsive to the liposome if the level of the biomarker or the complement thereof is substantially similar to the level of the biomarker or the complement thereof in a cell or tissue known to be sensitive to the liposome and/or the level of the biomarker or the complement thereof is substantially dissimilar to the level of the biomarker or the complement thereof in a cell or tissue known to be resistant to the liposome.

Methods of Treatment

The diagnostic methods of the invention permit the assessment of whether a patient is likely to be responsive to treatment with an sPLA$_2$ hydrolysable, cisplatin-containing liposome, and can thus be used to direct the patient's treatment (e.g., as a first line therapy and/or as a second or third line therapy). A patient to be treated or tested for responsiveness to an sPLA$_2$ hydrolysable, cisplatin-containing liposome according to the methods may include, e.g., a patient that has been diagnosed with cancer, a patient that has not received a cancer treatment (e.g., the liposome, an anti-cancer agent other than the liposome, or radiation), a patient that has received a cancer treatment (e.g., an anti-cancer agent other than the liposome or radiation), or a patient during treatment with the liposome. For example, the patient may have a solid tumor or a hematological cancer, such as a cancer type selected from breast cancer (e.g., medullary carcinoma, ER-positive breast cancer, and/or a metastatic form of breast cancer), prostate cancer, ovarian cancer (e.g., ovarian adenocarcinoma or embryonal carcinoma), liver cancer (e.g., hepatocellular carcinoma (HCC)

or hepatoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient is, e.g., breast cancer (e.g., ERpos breast cancer and/or a metastatic form of breast cancer), acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, renal cell carcinoma (RCC), esophageal cancer, melanoma, glioma, pancreatic cancer, gastrointestinal stromal tumors (GIST), sarcoma, non-small cell lung carcinoma (NSCLC), prostate cancer, ovarian cancer, colon cancer, bladder cancer, or squamous cell carcinoma of the head and neck (SCCHN).

The patient may have a cancer (e.g., breast cancer, such as an ERpos breast cancer and/or a metastatic form of breast cancer) that is resistant to one or more cancer therapies other than an sPLA$_2$ hydrolysable, cisplatin-containing liposome (e.g., docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab), surgery, or radiation. The patient may also have experienced a recurrence following a treatment with a cancer therapy other than the liposome, surgery, or radiation.

A patient found to be responsive to an sPLA$_2$ hydrolysable, cisplatin-containing liposome according to the methods of the invention may be preferentially selected for treatment with the liposome. For example, a patient can be identified as responsive to an sPLA$_2$ hydrolysable, cisplatin-containing liposome by determining the level of one or more biomarkers (e.g., one or more of the biomarkers shown in Tables 1-4, such as COL5A2 (SEQ ID NO: 73 or 211)) in a biological sample (e.g., a tumor sample) obtained from the patient, and subsequently administered the liposome. Optionally, the level of one or more of the biomarkers (e.g., one or more of the biomarkers shown in Tables 1-4, such as COL5A2 (SEQ ID NO: 73 or 211)) can be used in combination with the level of PLA2G2A (SEQ ID NO: 380) or sPLA$_2$ to identify patients responsive to an sPLA$_2$ hydrolysable, cisplatin-containing liposome. Alternatively, a patient can be identified as less likely to be responsive to an sPLA$_2$ hydrolysable, cisplatin-containing liposome by determining the level of one or more biomarkers (e.g., one or more of the biomarkers shown in Tables 1-4, such as COL5A2 (SEQ ID NO: 73 or 211)) in a biological sample obtained from the patient. Likewise, a patient may be less likely to be responsive to an sPLA$_2$ hydrolysable, cisplatin-containing liposome if the level of PLA2G2A (SEQ ID NO: 380) or sPLA$_2$ is not detected in a tumor sample from the patient.

If the patient exhibits levels of one or more biomarkers indicative of non-responsiveness to an sPLA$_2$ hydrolysable, cisplatin-containing liposome, the patient may be treated with or offered a treatment with an agent other than the liposome. Additionally, the patient may be treated with or offered a treatment with an agent other than the liposome if the level of PLA2G2A (SEQ ID NO: 380) or sPLA$_2$ is not detected in a tumor sample from the patient. In particular, the patient may be treated with, e.g., radiation and/or administration of a therapeutic agent, such as docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab.

Administration of an $sPLA_2$ Hydrolysable, Cisplatin-Containing Liposome

Once a patient has been determined to be responsive to an $sPLA_2$ hydrolysable, cisplatin-containing liposome, according to the methods described herein, the liposome may be administered to the patient, for example, parenterally or enterally. Enteral routes of the liposome administration include oral, buccal, sublabial, sublingual, or by inhalation. Parenteral routes of the liposome administration include intravenous, transdermal, intradermal, intramuscular, intraarterial, intracranial, subcutaneous, intraorbital, intraventricular, intraspinal, intraperitoneal, or intranasal. The preferred route for administration of the $sPLA_2$ hydrolysable, cisplatin-containing liposome may be intravenous, such as intravenous infusion or as a bolus injection. For example, the $sPLA_2$ hydrolysable, cisplatin-containing liposome is administered by intravenous infusion over a time period of, e.g., 15 minutes, 30 minutes, 45 minutes, 60 minutes, 75 minutes, 90 minutes, 105 minutes, 120 minutes, 135 minutes, 150 minutes, 180 minutes, or more. The $sPLA_2$ hydrolysable, cisplatin-containing liposome may also be administered as, e.g., a bolus injection.

An $sPLA_2$ hydrolysable, cisplatin-containing liposome can be administered at, e.g., a dose of about 60 mg/m$^2$ to 120 mg/m$^2$ of cisplatin, such as about 75 mg/m$^2$ of cisplatin. For example, an $sPLA_2$ hydrolysable, cisplatin-containing liposome may be administered at a dose of about 60 mg/m$^2$ of cisplatin, 65 mg/m$^2$ of cisplatin, 70 mg/m$^2$ of cisplatin, 75 mg/m$^2$ of cisplatin, 80 mg/m$^2$ of cisplatin, 85 mg/m$^2$ of cisplatin, 90 mg/m$^2$ of cisplatin, 95 mg/m$^2$ of cisplatin, 100 mg/m$^2$ of cisplatin, 105 mg/m$^2$ of cisplatin, 110 mg/m$^2$ of cisplatin, 115 mg/m$^2$ of cisplatin, or 120 mg/m$^2$ of cisplatin. An $sPLA_2$ hydrolysable, cisplatin-containing liposome may be administered at a frequency of, e.g., at least once hourly, once daily, twice daily, once weekly, once every two weeks, once every three weeks, once every four weeks, once monthly, once every two months, once every three months, once every six months, or once every year.

In particular, an $sPLA_2$ hydrolysable, cisplatin-containing liposome may be administered at a treatment regimen of, e.g., about 75 mg/m$^2$ of cisplatin on day 1 and day 8 of a 3 week cycle (1 cycle) for 1 to 3 cycles or more. Additionally, the $sPLA_2$ hydrolysable, cisplatin-containing liposome may be administered at a treatment regimen of, e.g., about 60 mg/m$^2$ of cisplatin on day 1 and day 8 of a 3 week cycle (1 cycle) for 1 to 3 cycles or more. The $sPLA_2$ hydrolysable, cisplatin-containing liposome may also be administered at a treatment regimen of, e.g., about 90 mg/m$^2$ of cisplatin on day 1 and day 8 of a 3 week cycle (1 cycle) for 1 to 3 cycles or more. The treatment regimen may be repeated one to five times, one to ten times, one to fifteen times, one to twenty times, or more. The administration of the $sPLA_2$ hydrolysable, cisplatin-containing liposome can be repeated at such a frequency for a certain period of time, followed by a period without treatment. Such repeated administrations can occur over a course of therapy lasting a specified length of time (e.g., at least 1 week, 2 weeks, 3 weeks, 1 month, 2 months, 3 months, 6 months, 8 months, 10 months, 12 months, 18 months, 24 months, 36 months, 48 months, or 60 months).

An $sPLA_2$ hydrolysable, cisplatin-containing liposome can be administered in a pharmaceutical composition that includes one or more pharmaceutically acceptable carriers, excipients, or diluents. Examples of suitable carriers, excipients, or diluents of the liposome include, but are not limited to, sodium chloride solution, saline, sterile water, polyalkylene glycols, oils of vegetable origin, hydrogenated napthalenes, suitable buffer, 1,3-butanediol, and/or Ringer's solution. In particular, the $sPLA_2$ hydrolysable, cisplatin-containing liposome is administered in a pharmaceutical composition that includes about 0.9% sodium chloride. Other exemplary carriers, excipients, or diluents are described in the Handbook of Pharmaceutical Excipients, 6th Edition, Rowe et al., Eds., Pharmaceutical Press (2009), hereby incorporated by reference in its entirety.

$sPLA_2$ Hydrolysable Liposomes

An $sPLA_2$ hydrolysable, cisplatin-containing liposome for use in the methods may include anionic lipids, neutral phospholipids, and polymer-conjugated lipids. For example, the liposome includes about 40% to about 75% (mol/mol) of a neutral phospholipid, about 20% to about 45% (mol/mol) of an anionic lipid, and about 3% to about 6% (mol/mol) of a polymer-conjugated lipid. In particular, the liposome includes distearoyl phosphatidyl glycerol (DSPG) in an amount of about 25% (mol/mol), distearoyl phosphatidyl choline (DSPC) in an amount of about 70% (mol/mol), and [poly(ethylene glycol)]-distearoyl phosphatidyl ethanolamine (DSPE-PEG) in an amount of about 5% (mol/mol).

The $sPLA_2$ hydrolysable liposome may include, e.g., about 20% to about 45% (mol/mol) of an anionic lipid, such as about 20% to about 40% (mol/mol) anionic lipid, about 20% to about 30% (mol/mol) anionic lipid, about 25% to about 40% (mol/mol) anionic lipid, about 25% to about 35% (mol/mol) anionic lipid, or about 25% to about 30% (mol/mol) anionic lipid. The anionic lipid may include one or more phospholipids, such as phosphatidyl inositol (PI), phosphatidyl serine (PS), bisphosphatidyl glycerol (DPG), phosphatidic acid (PA), phosphatidyl alcohol (PEON), or phosphatidyl glycerol (PG). In particular, the anionic phospholipid is PG including stearoyl chains, such has DSPG in an amount of about 25% (mol/mol) of the liposomal composition.

The $sPLA_2$ hydrolysable, cisplatin-containing liposome may also include one or more neutral phospholipids, such as phosphatidyl choline (PC) or phosphatidylethanolamine (PE), in an amount of about 40% to about 75% (mol/mol) of the liposomal composition. Preferably, the neutral phospholipid is PC, such as PC in an amount of about 50% to about 70% (mol/mol). In particular, the neutral lipid also includes stearoyl chains, such as the liposome includes DSPC in an amount of about 70% (mol/mol).

Additionally, the liposome may include one or more polymer-conjugated lipid, such as PEG [poly(ethylene glycol)], PAcM [poly(N-acryloylmorpholine)], PVP [poly(vinylpyrrolidone)], PLA [poly(lactide)], PG [poly(glycolide)], POZO [poly(2-methyl-2-oxazoline)], PVA [poly(vinyl alcohol)], HPMC (hydroxypropylmethylcellulose), PEO [poly (ethylene oxide)], chitosan [poly(D-glucosamine)], PAA [poly(aminoacid)], polyHEMA [Poly(2-hydroxyethylmethacrylate)], and co-polymers thereof. Preferably, the liposome includes a polymer-conjugated lipid in an amount of at least 2%, such as an amount of polymer-conjugated lipid of at least 5% and no more than 15% (mol/mol) or at least 3% and no more than 6% (mol/mol). For example, the liposome includes DSPE-PEG in an amount of about 5% (mol/mol).

Kits

Kits of the invention can be used for determining the responsiveness of a cancer patient (e.g., a patient having a solid tumor cancer, such as breast cancer, or a hematological cancer, such as lymphoma (e.g., cutaneous T-cell lymphoma (CTCL)) to an sPLA$_2$ hydrolysable, cisplatin-containing liposome. Kits of the invention can include reagents and/or materials for, e.g., collecting and/or purifying nucleic acids from biological samples (such as those obtained from a patient to be treated with a target drug(s) of the invention), reagents for amplifying such nucleic acids to produce an amplified sample, and/or at least one device of the invention. Reagents for amplifying nucleic acids may include, e.g., PCR reagents, including but not limited to DNA polymerase, RNA polymerase, PCR buffer, magnesium chloride solutions, nucleic acid primers (e.g., primers designed to target particular biomarkers of responsiveness to a target drug(s) of interest), and/or any other PCR reagents as are well known in the art. In particular, kits useful in the method may include one or more of the following: a kit for RNA extraction from tumors (e.g., Trizol for mRNA, mirVana miRNA isolation kit from Ambion Inc), a kit for RNA labeling (e.g., MessageAmp from Ambion Inc., FlashTag from Genisphere Inc), a microarray for measuring biomarker levels (e.g., HG-U133A, HG-U133_Plus2 or miRNA-1.0 from Affymetrix Inc), a microarray hybridization station and scanner (e.g., GeneChip System 3000Dx from Affymetrix Inc), and/or software for analyzing the levels of biomarkers as described in herein (e.g., implemented in R from R-Project or S-Plus from Insightful Corp.).

For example, a kit of the invention can include one or more probes capable of detecting one or more biomarkers of Tables 1-4 (e.g., the kit may include probes for one or more of the biomarkers of Tables 1-4) and, optionally, one or more probes for detecting PLA2G2A (SEQ ID NO: 380). Such probes can, for example, include nucleic acids capable of specifically hybridizing to the biomarker(s) based on nucleic acid sequence complementarity. In particular, a probe has at least 85% sequence identity (e.g., 85%, 90%, 95%, 97%, 98%, 99%, or 100% sequence identity) to a nucleic acid sequence that is complementary or identical to at least 5 (e.g., at least 15 or more) consecutive nucleotides of one or more biomarkers. The probes can be attached to a solid surface, such as a microarray. The kit may include NanoString capture probes, NanoString reporter probes, and/or one or more nCounter cartridges. The kit may include reagents for next generation sequencing, including but not limited to poly(T) oligonucleotides, dye terminators, sequencing adapters, adapter ligation reagents, reverse transcriptase, primers (e.g., random primers), DNA-cleaving enzymes, polymerases, and/or any combination thereof. The kit may also be one that includes a protein array and/or reagents for detection of the polypeptide product(s) of one or more biomarkers of Tables 1-4 (e.g., antibodies or antigen-binding fragments that specifically bind to the one or more biomarkers), and optionally, an anti-sPLA$_2$ antibody for detecting the sPLA$_2$ protein.

The following examples are intended to illustrate, rather than limit, the invention.

EXAMPLES

Example 1. Identification of Biomarkers of Sensitivity and Resistance to Cisplatin Using Affymetrix HG-U133A Arrays DNA chip measurements of the 60 cancer cell lines of the NCI60 data set were performed using Affymetrix HG-U133A arrays and logit normalized. For each array, the logit transformation was performed followed by a Z-transformation to mean zero and SD 1, and correlated to growth inhibition (log(G150)). Growth inhibition data of cisplatin against the same cell lines were downloaded from the National Cancer Institute. Each gene's expression in each cell line was correlated to the growth of those cell lines (log(G150)) in the presence of cisplatin. The Pearson correlation coefficient was then determined to identify genes positively and negatively correlated to sensitivity to cisplatin. Tables 1 and 2 show the top positively correlated genes (the biomarkers of sensitivity) and negatively correlated genes (the biomarkers of resistance) using the Affymetrix HG-U133A arrays. These biomarkers of sensitivity and resistance shown in Tables 1 and 2, respectively, may be used individually or in combination to identify patients that are responsive to an sPLA$_2$ hydrolysable, cisplatin-containing liposome.

Example 2. Identification of Biomarkers of Sensitivity and Resistance to an sPLA$_2$ Hydrolysable, Cisplatin-Containing Liposome Using Affymetrix HG-U133A Arrays DNA chip measurements of the 60 cancer cell lines of the NCI60 data set were also performed using HG-U133_Plus_2 arrays and logit normalized. For each array, the logit transformation was performed followed by a Z-transformation to mean zero and SD 1, and correlated to growth inhibition (log(G150)). Growth inhibition data of a sPLA$_2$ hydrolysable, cisplatin-containing liposome against the same cell lines were downloaded from the National Cancer Institute. Each gene's expression in each cell line was correlated to the growth of those cell lines (log(G150)) in the presence of the liposome. The covariance (Pearson correlation coefficient multiplied by standard deviation) was then determined to identify genes positively and negatively correlated to sensitivity to the liposome. Tables 3 and 4 show the top positively correlated genes (the biomarkers of sensitivity) and negatively correlated genes (the biomarkers of resistance) using the Affymetrix HG-U133A arrays, respectively. These biomarkers of sensitivity and resistance shown in Tables 3 and 4, respectively, may be used individually or in combination to identify patients that are responsive to an sPLA$_2$ hydrolysable, cisplatin-containing liposome.

Example 3. Predicting Responsiveness to an sPLA$_2$ Hydrolysable, Cisplatin-Containing Liposome in Various Cancer Patient Populations An mRNA-based predictor of responsiveness to an sPLA$_2$ hydrolysable, cisplatin-containing liposome developed according to the methods of the invention was applied to 3,522 patients having a variety of cancers. Each patient had a pre-treatment measurement of gene expression with an Affymetrix array. The predicted liposome sensitivity of each patient was calculated as the difference between the mean of the levels of the biomarkers of sensitivity (Table 1) and the mean of the levels of the biomarkers of resistance (Table 2) for the patient. When the patients were grouped by cancer types, and cancer types predicted to be more responsive to the liposome were identified (FIG. 1). Of 27 different cancer types, patients with hematological cancer types were predicted to be responsive to the liposome treatment than patients with solid tumor cancers.

The median of the boxplots shown in FIG. 1 is a cutoff that may be used to separate patients predicted to be responsive to treatment with the sPLA$_2$ hydrolysable, cisplatin-containing liposome from patients predicted to be non-responsive to the liposome treatment for a given cancer type. Values above the median indicate patients predicted to be responsive to the liposome, while values below the median indicate patients predicted to be non-responsive to the liposome. For a test sample from an individual patient, it is useful to compare the test sample to the reference population for the same cancer type. If the test sample is above the median for the reference population of the same cancer type, then the patient is predicted to be responsive to the liposome treatment. If the test sample is below the median for the reference population of the same cancer type, then the patient is predicted to be non-responsive to the liposome treatment. This method for predicting patient responsiveness can also be used when the reference cancer population consists of only two patients: a patient responsive to the liposome treatment and a patient non-responsive to the liposome treatment.

Example 4. Determining the Presence of Secreted Phospholipase A$_2$ (sPLA$_2$)

The presence of secreted sPLA$_2$ in the tumor tissue of a patient having cancer can be used in combination with the expression of the biomarkers listed in Tables 1-4 to determine the responsiveness of a patient to an sPLA$_2$ hydrolysable, cisplatin-containing liposome. Expression of the enzyme sPLA$_2$ is required for degradation of the liposomes that deliver cisplatin to the tumor tissue of the patient and can be measured using standard immunocytochemistry techniques with a monoclonal antibody against sPLA2-IIA, e.g. Clone SCACC353 from Cayman Chemical. Any staining in this assay indicates the presence of sPLA$_2$ and suggests susceptibility to the liposome. Alternatively, the expression of sPLA2-IIA can be detected using a microarray including one or more probes for PLA2G2A (SEQ ID NO: 380) or qRT-PCR to determine a level of PLA2G2A (SEQ ID NO: 380) in a tumor sample from the patient. While there is a negative covariance between PLA2G2A (SEQ ID NO: 380) and the liposome response in cancer cell lines in vitro, there is a positive correlation between detection of a level of PLA2G2A in a tumor tissue sample (Mirtti et al. APMIS 117: 151-161, 2009; hereby incorporated by reference).

Example 5. Predicting Responsiveness of Breast Cancer Patients to the Liposome The diagnostic methods of the present invention can be used to predict the responsiveness of a breast cancer patient to treatment with an sPLA$_2$ hydrolysable, cisplatin-containing liposome. In particular, the breast cancer patient may be one that has not previously received any cancer treatment or one that has received a cancer treatment other than the liposome. Moreover, the patient may be one diagnosed with breast cancer and/or one with recurrence of breast cancer. A biological sample (e.g., a breast cancer tissue sample) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A or HG-U133_Plus_2 array, for one or more of the biomarkers shown in Tables 1-4. One or more of the biomarkers shown in Tables 1-4 can also be measured, e.g., by sequencing or PCR-based techniques, such as those described herein.

For example, the level of one or more biomarkers of sensitivity to the liposome can be determined in the sample from the patient, such as one or more of COL5A2 (SEQ ID NO 73 or 211), ITGA4 (SEQ ID NO: 1), MSN (SEQ ID NO: 2), FAM46A (SEQ ID NO: 3 or 280), ITGB2 (SEQ ID NO: 4), DOCK2 (SEQ ID NO: 5 or 223), EVL (SEQ ID NO: 6), SACS (SEQ ID NO: 7), PTPRCAP (SEQ ID NO: 8), EBI2 (SEQ ID NO: 9), PTPRC (SEQ ID NO: 10, 18, 25, or 243), ANP32E (SEQ ID NO: 11), SFPQ (SEQ ID NO: 12, 38, or 272), C1QR1 (SEQ ID NO: 13), FNBP1 (SEQ ID NO: 14 or 28), CBFB (SEQ ID NO: 15), SFRS7 (SEQ ID NO: 19 or 54), CAP350 (SEQ ID NO: 20 or 61), CALD1 (SEQ ID NO: 206), COL6A2 (SEQ ID NO: 207), FERMT2 (SEQ ID NO: 208), BNIP3 (SEQ ID NO: 209 or 263), RAB31 (SEQ ID NO: 210), MPO (SEQ ID NO: 212), SRPX (SEQ ID NO: 213), ARHGDIB (SEQ ID NO: 214), TMEM47 (SEQ ID NO: 215), CSRP2 (SEQ ID NO: 216), DPYSL3 (SEQ ID NO: 217), HTRA1 (SEQ ID NO: 218), SLC39A6 (SEQ ID NO: 219), and LAT2 (SEQ ID NO: 220). In particular, the biomarker is COL5A2 (SEQ ID NO 73 or 211). The level of one or more biomarkers of resistance to the liposome can also be determined in the sample from the patient, such as one or more of SFN (SEQ ID NO: 96 or 324), LISCH7 (SEQ ID NO: 97), EPB41 L4B (SEQ ID NO: 98), MST1R (SEQ ID NO: 99), ITGB4 (SEQ ID NO: 100), DBNDD2 (SEQ ID NO: 102 or 365), TACSTD1 (SEQ ID NO: 104), MISP (SEQ ID NO: 105), KRT8 (SEQ ID NO: 106), JUP (SEQ ID NO: 107 or 400), KRT18 (SEQ ID NO: 108 or 306), FA2H (SEQ ID NO: 109), MGAT4B (SEQ ID NO: 110), DSG2 (SEQ ID NO:111 or 312), LRP5 (SEQ ID NO: 112), LGALS3 (SEQ ID NO: 307), DSP (SEQ ID NO: 308), IGFBP4 (SEQ ID NO: 309), SPINT2 (SEQ ID NO: 310), CDH1 (SEQ ID NO: 311), RAB25 (SEQ ID NO: 313), PTPRF (SEQ ID NO: 314, 371, or 387), SOX9 (SEQ ID NO: 121, 315, or 319), LYZ (SEQ ID NO: 316), IER3 (SEQ ID NO: 127 or 317), PERP (SEQ ID NO: 318), ATP1B1 (SEQ ID NO: 320), and IFI27 (SEQ ID NO: 321). In particular, the biomarker is SFN (SEQ ID NO: 96 or 324). The breast cancer patient may be responsive to the liposome if the level of one or more of the biomarkers of sensitivity is substantially similar to the level of the biomarkers of sensitivity in a cell or tissue known to be sensitive to the liposome. The breast cancer patient may also be responsive to the liposome if the level of one or more of the biomarkers of resistance is substantially dissimilar to the level of the biomarkers of resistance in a cell or tissue known to be resistant to the liposome.

Additionally, the presence of secreted phospholipase A$_2$ (sPLA2-IIA) in the tumor tissue of a patient having breast cancer can be used in combination with one or more of the biomarkers of Tables 1-4 to determine the responsiveness of the breast cancer patient to the sPLA$_2$ hydrolysable, cisplatin-containing liposome. The presence of sPLA$_2$ can be measured using standard immunocytochemistry techniques with a monoclonal antibody against sPLA-IIA, such as Clone SCACC353 from Cayman Chemical. Any staining of the tumor tissue using an anti-sPLA$_2$ antibody indicates the presence of sPLA$_2$ and suggests that the breast cancer patient may be responsive to treatment with the liposome. Alternatively, the expression of sPLA2-IIA can be detected using a microarray including one or more probes that are capable of specifically hybridizing with PLA2G2A (SEQ ID NO: 380) or using qRT-PCR to determine the level of PLA2G2A (SEQ ID NO: 380).

If the breast cancer patient is predicted to be responsive to treatment with the sPLA$_2$ hydrolysable, cisplatin-containing liposome, then the patient can be administered the liposome, such as intravenous administration of the liposome at about 60 to about 120 mg/m² on day 1 and day 8 of a three week regimen (e.g., 75 mg/m² of the liposome). Conversely, if the patient is predicted to be non-responsive to treatment with the liposome, then the patient can be treated with one or more therapies other than the liposome, such as surgery, radiation, or a non-liposome therapeutic agent (e.g., docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, or rituximab).

Example 6. Clinical Validation of Identified Biomarkers of Resistance and Sensitivity The biomarkers of sensitivity and resistance identified in Example 1 and shown in Tables 1 and 2 have been validated in five clinical trials. Table 5 below summarizes the results of these studies. In each trial, the overall response rate (ORR) or overall survival (OS) is substantially higher in the top 10% of patients identified as responsive to treatment (e.g., the sPLA$_2$ hydrolysable, cisplatin-containing liposome) using the biomarkers of sensitivity and resistance than in the bottom 10% of patients identified as responsive to treatment using the biomarkers of sensitivity and resistance.

Trials 1-3 are retrospective analyses of published data including Affymetrix assays of pre-treatment biopsies from patients treated with platinum, cisplatin, or cisplatin and vinorelbine, respectively, having ovarian cancer, breast cancer, or non-small cell lung carcinoma (NSCLC), respectively. In Trial 3, the biomarkers of sensitivity and resistance were used to evaluate responsiveness to cisplatin without an additional predictor of responsiveness to vinorelbine. In Trial 4, the biomarkers of sensitivity and resistance were used to analyze archived tumor samples of NSCLC patients. Trial 5 is a prospective trial of tumor samples from breast cancer patients screened with the biomarkers of sensitivity and resistance of Tables 1 and 2, respectively, prior to treatment with the sPLA$_2$ hydrolysable, cisplatin-containing liposome. Only the breast cancer patients in the top 67% of patients predicted to be responsive to liposome treatment and positive for sPLA$^2$ presence in a tumor sample from the patient, as determined using an immunohistochemistry assay, were treated with the liposome (trial ongoing until N=15). All studies were conducted with the Affymetrix HG-U133A or HG-U133Plus2 array.

TABLE 5

Summary of clinical trials conducted using biomarkers of sensitivity and resistance (Tables 1 and 2, respectively) to treatment, such as the sPLA$_2$ hydrolysable, cisplatin-containing liposome. The overall response rate (ORR) and overall survival (OS) are shown for patients predicted to be in the top 10% or bottom 10% of responsiveness to the treatment for each respective trial.

| Trial No. | 1 | 2 | 3 | 4 | 5 |
|---|---|---|---|---|---|
| Cancer | Ovarian | Breast | NSCLC | NSCLC | Breast, etc. |
| Drug | Platinum | Cisplatin | Cisplatin and Vinorelbine | Cisplatin and Vinorelbine | sPLA$_2$ hydrolysable, cisplatin-containing liposome |
| Level of Evidence | Retrospective | Retrospective | Retrospective | Prospective archival | Prospective screening |
| Setting | adjuvant | neoadj | adjuvant | adjuvant | metastat |
| Assay | Fresh | Fresh | Fresh | FFPE | FFPE |
| N | 28 | 24 | 71 | 95 | 11 (so far) |
| Top 10% | ORR 100% | ORR 100% | 3Y OS 100% | 3Y OS 100% | ORR 100% |
| Bottom 10% | ORR 67% | ORR 50% | 3Y OS 71% | 3Y OS 55% | 0% |

As shown in Table 5, the ORR and OS in the top 10% of patients predicted to be responsive to treatment was 100% and the bottom 10% of patients predicted to be responsive to treatment was substantially lower, ranging from 50% to 71%, in all trials including patients with ovarian cancer, breast cancer, and NSCLC. In trial number 5, also with a cutoff of 33% (top 67%) there is a 67% probability of response and a median of 18 weeks to progression of disease, whereas patients below this cutoff have a 0% probability of response and a median of 3 weeks to progression. These five clinical trials indicate that the biomarkers of sensitivity and resistance of Tables 1-4 can be used singly or in combination with detection of sPLA$_2$ in patient tumor samples to identify cancer patients that are likely to be responsive to treatment with, e.g., a sPLA$_2$ hydrolysable, cisplatin-containing liposome.

Other Embodiments

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. For example, it is anticipated that measuring the level of proteins, metabolites, identifying genetic mutations and DNA copy number variations, all will be useful in determining patient responsiveness.

The invention claimed is:

1. A method of treating cancer in a subject in need thereof comprising administering a secretory phospholipase $A_2$ ($sPLA_2$) hydrolysable, cisplatin-containing liposome to the subject, wherein the cancer is selected from the group consisting of liver cancer, colorectal cancer, lung cancer, esophageal cancer, skin cancer, pancreatic cancer, prostate cancer, or breast cancer and wherein the subject has been determined to be responsive to the sPLA2-hydrolysable, cisplatin-containing liposome according to a method comprising:
   (a) contacting a tumor sample from the subject comprising nucleic acid molecules with a device comprising:
      i) single-stranded nucleic acid molecules capable of specifically hybridizing with nucleotides of biomarkers of sensitivity, wherein the biomarkers of sensitivity are ITGA4, MSN, FAM46A, and ITGB2, and
      ii) single-stranded nucleic acid molecules capable of specifically hybridizing with nucleotides of biomarkers of resistance, wherein the biomarkers of resistance are SFN, LISCH7, EPB41L4B, and MST1R; and
   (b) detecting a level of expression of the biomarkers of sensitivity and the biomarkers of resistance; and
   (c) calculating a difference score for the subject by subtracting a mean of the level of expression of the biomarkers of resistance from a mean of the level of expression of the biomarkers of sensitivity, wherein the difference score is above a cutoff value.

2. The method of claim 1, further comprising administering one or more additional cancer therapies other than the liposome to the subject prior to, concurrently with, or after administration of the liposome.

3. The method of claim 2, wherein the one or more additional cancer therapies is selected from the group consisting of docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

4. The method of claim 1, wherein the liposome is administered to the subject intravenously, intramuscularly, transdermally, intradermally, intra-arterially, intracranially, subcutaneously, intraorbitally, intraventricularly, intraspinally, intraperitoneally, or intranasally.

5. The method of claim 1, wherein the liposome is administered to the subject at a dose of about 60 mg/m$^2$ to about 120 mg/m$^2$ of cisplatin.

6. The method of claim 1, comprising administering the liposome to the subject in a treatment regimen at least once per one, two, or three weeks or on day 1 and day 8 of a 3 week treatment regimen.

7. The method of claim 1, wherein the subject is resistant to one or more additional cancer therapies other than the sPLA$_2$ hydrolysable, cisplatin-containing liposome.

8. The method of claim 1, wherein the subject exhibits cancer relapse after treatment with one or more cancer therapies other than the liposome.

9. The method of claim 1, wherein the subject has not been determined to be resistant to the sPLA$_2$ hydrolysable, cisplatin-containing liposome.

10. The method of claim 1, wherein the one or more single-stranded nucleic acid molecules of the device have a length in the range of 10 to 100 nucleotides.

11. The method of claim 1, wherein the cutoff value is at a $50^{th}$ percentile or greater of the difference score in a reference population with the same diagnosis as the subject.

12. The method of claim 1, wherein the device is a microarray or is for performing a quantitative reverse transcriptase polymerase chain reaction (qRT-PCR) reaction; and the level of the biomarkers of sensitivity are detected by performing microarray analysis or qRT-PCR.

13. The method of claim 1, wherein the nucleic acid molecules of the sample comprise mRNA or a cDNA thereof.

14. The method of claim 2, wherein the one or more additional cancer therapies comprise surgery, radiation, or a therapeutic agent.

15. The method of claim 6, wherein the treatment regimen is repeated two to twenty times.

16. The method of claim 1, wherein the cancer is breast cancer.

17. The method of claim 16, wherein the breast cancer is an estrogen receptor-positive (ERpos) breast cancer and/or a metastatic form of breast cancer.

18. The method of claim 1, wherein the detecting occurs by performing microarray analysis or qRT-PCR.

19. The method of claim 1, wherein the subject exhibits cancer relapse after a first treatment with a cancer therapy other than the liposome and prior to treatment with the liposome.

20. The method of claim 1, wherein the subject has not been administered a treatment for cancer.

21. The method of claim 10, wherein the length of the one or more single-stranded nucleic acid molecules of the device is in the range of 20 to 60 nucleotides.

22. The method of claim 1, wherein the one or more single-stranded nucleic acid molecules of the device are labeled or immobilized on a solid substrate.

23. The method of claim 11, wherein the cutoff value is at a $60^{th}$ percentile or greater of the difference score in the reference population.

24. The method of claim 23, wherein the cutoff value is at a $70^{th}$ percentile or greater of the difference score in the reference population.

25. The method of claim 24, wherein the cutoff value is at an $80^{th}$ percentile or greater of the difference score in the reference population.

26. The method of claim 25, wherein the cutoff value is at a $90^{th}$ percentile or greater of the difference score in the reference population.

* * * * *

SEQUENCE LISTING

```
<160> NUMBER OF SEQ ID NOS: 405

<210> SEQ ID NO 1
<211> LENGTH: 25
<212> TYPE: DNA
<213> ORGANISM: Homo sapiens

<400> SEQUENCE: 1
caggcctctc agatacaagg ggaac                                              25

<210> SEQ ID NO 2
<211> LENGTH: 25
<212> TYPE: DNA
<213> ORGANISM: Homo sapiens

<400> SEQUENCE: 2
atagctgcct taaagtcagt aactt                                              25

<210> SEQ ID NO 3
<211> LENGTH: 25
<212> TYPE: DNA
<213> ORGANISM: Homo sapiens

<400> SEQUENCE: 3
caccatgctg gctatccggg tgtta                                              25

<210> SEQ ID NO 4
<211> LENGTH: 25
<212> TYPE: DNA
<213> ORGANISM: Homo sapiens

<400> SEQUENCE: 4
ctccactctg actggcacag tcttt                                              25

<210> SEQ ID NO 5
<211> LENGTH: 25
<212> TYPE: DNA
<213> ORGANISM: Homo sapiens

<400> SEQUENCE: 5
gattcctgaa ctcaaggtac cagca                                              25

<210> SEQ ID NO 6
<211> LENGTH: 25
<212> TYPE: DNA
<213> ORGANISM: Homo sapiens

<400> SEQUENCE: 6
gatcatcgac gccatcaggc aggag                                              25

<210> SEQ ID NO 7
<211> LENGTH: 25
<212> TYPE: DNA
<213> ORGANISM: Homo sapiens

<400> SEQUENCE: 7
gtgtggttga acaggatgca atctt                                              25
```

<210> SEQ ID NO 8
<211> LENGTH: 25
<212> TYPE: DNA
<213> ORGANISM: Homo sapiens

<400> SEQUENCE: 8
gcttcccaag atgccatggc tggac                                         25

<210> SEQ ID NO 9
<211> LENGTH: 25
<212> TYPE: DNA
<213> ORGANISM: Homo sapiens

<400> SEQUENCE: 9
gcaggacttc ccttataaag caaaa                                         25

<210> SEQ ID NO 10
<211> LENGTH: 25
<212> TYPE: DNA
<213> ORGANISM: Homo sapiens

<400> SEQUENCE: 10
gattataacc gtgttgaact ctctg                                         25

<210> SEQ ID NO 11
<211> LENGTH: 25
<212> TYPE: DNA
<213> ORGANISM: Homo sapiens

<400> SEQUENCE: 11
gttttcggtc ctattttaat gctct                                         25

<210> SEQ ID NO 12
<211> LENGTH: 25
<212> TYPE: DNA
<213> ORGANISM: Homo sapiens

<400> SEQUENCE: 12
aaagaccaac aaatctcaag cccta                                         25

<210> SEQ ID NO 13
<211> LENGTH: 25
<212> TYPE: DNA
<213> ORGANISM: Homo sapiens

<400> SEQUENCE: 13
ggtctgttct tgtagataat gccct                                         25

<210> SEQ ID NO 14
<211> LENGTH: 25
<212> TYPE: DNA
<213> ORGANISM: Homo sapiens

<400> SEQUENCE: 14
tgctggccac ggattttgac gacga                                         25

<210> SEQ ID NO 15
<211> LENGTH: 25
<212> TYPE: DNA
<213> ORGANISM: Homo sapiens

<400> SEQUENCE: 15
ggtgttgtac agctcacatg tttac                                      25

<210> SEQ ID NO 16
<211> LENGTH: 25
<212> TYPE: DNA
<213> ORGANISM: Homo sapiens

<400> SEQUENCE: 16
ggtttgcctc attgtgctat ttgcc                                      25

<210> SEQ ID NO 17
<211> LENGTH: 25
<212> TYPE: DNA
<213> ORGANISM: Homo sapiens

<400> SEQUENCE: 17
ataagcattg attcctgcat ttctg                                      25

<210> SEQ ID NO 18
<211> LENGTH: 25
<212> TYPE: DNA
<213> ORGANISM: Homo sapiens

<400> SEQUENCE: 18
gcatttagtc caatgtcttt ttaag                                      25

<210> SEQ ID NO 19
<211> LENGTH: 25
<212> TYPE: DNA
<213> ORGANISM: Homo sapiens

<400> SEQUENCE: 19
atcatgctga ggcgccttgc aaatc                                      25

<210> SEQ ID NO 20
<211> LENGTH: 25
<212> TYPE: DNA
<213> ORGANISM: Homo sapiens

<400> SEQUENCE: 20
atgactggta tgatagctct tgaca                                      25

<210> SEQ ID NO 21
<211> LENGTH: 25
<212> TYPE: DNA
<213> ORGANISM: Homo sapiens

<400> SEQUENCE: 21
caatccaagc ataactcagt gacgc                                      25

<210> SEQ ID NO 22
<211> LENGTH: 25
<212> TYPE: DNA
<213> ORGANISM: Homo sapiens

<400> SEQUENCE: 22
gaatgtgtag ctcaaatgca aacca                                      25

<210> SEQ ID NO 23
<211> LENGTH: 25
<212> TYPE: DNA
<213> ORGANISM: Homo sapiens

<400> SEQUENCE: 23

```
ttccctcctt atagtcaagg accgt                                          25

<210> SEQ ID NO 24
<211> LENGTH: 25
<212> TYPE: DNA
<213> ORGANISM: Homo sapiens

<400> SEQUENCE: 24
tgacctcggt cacaaaagca gtttt                                          25

<210> SEQ ID NO 25
<211> LENGTH: 25
<212> TYPE: DNA
<213> ORGANISM: Homo sapiens

<400> SEQUENCE: 25
gaacagtttg tacagacgta tgctt                                          25

<210> SEQ ID NO 26
<211> LENGTH: 25
<212> TYPE: DNA
<213> ORGANISM: Homo sapiens

<400> SEQUENCE: 26
tacaacacta tacatacaca ccacc                                          25

<210> SEQ ID NO 27
<211> LENGTH: 25
<212> TYPE: DNA
<213> ORGANISM: Homo sapiens

<400> SEQUENCE: 27
ttatgccagc ttatattgtg agaac                                          25

<210> SEQ ID NO 28
<211> LENGTH: 25
<212> TYPE: DNA
<213> ORGANISM: Homo sapiens

<400> SEQUENCE: 28
gagttgcctg tttgtctctg gagat                                          25

<210> SEQ ID NO 29
<211> LENGTH: 25
<212> TYPE: DNA
<213> ORGANISM: Homo sapiens

<400> SEQUENCE: 29
gctgcagtgt agatggctct tgttt                                          25

<210> SEQ ID NO 30
<211> LENGTH: 25
<212> TYPE: DNA
<213> ORGANISM: Homo sapiens

<400> SEQUENCE: 30
acgttgtcac cggagcactg aagat                                          25

<210> SEQ ID NO 31
<211> LENGTH: 25
<212> TYPE: DNA
<213> ORGANISM: Homo sapiens
```

```
<400> SEQUENCE: 31
atagcagcac acattttcac gtttc                                          25

<210> SEQ ID NO 32
<211> LENGTH: 25
<212> TYPE: DNA
<213> ORGANISM: Homo sapiens

<400> SEQUENCE: 32
aagaccggca gatggtggtg ctgga                                          25

<210> SEQ ID NO 33
<211> LENGTH: 25
<212> TYPE: DNA
<213> ORGANISM: Homo sapiens

<400> SEQUENCE: 33
atttggctca agtccatttg gctgt                                          25

<210> SEQ ID NO 34
<211> LENGTH: 25
<212> TYPE: DNA
<213> ORGANISM: Homo sapiens

<400> SEQUENCE: 34
gcatgaagtt gcccttaacc actaa                                          25

<210> SEQ ID NO 35
<211> LENGTH: 25
<212> TYPE: DNA
<213> ORGANISM: Homo sapiens

<400> SEQUENCE: 35
taaccatgct tacacactaa actat                                          25

<210> SEQ ID NO 36
<211> LENGTH: 25
<212> TYPE: DNA
<213> ORGANISM: Homo sapiens

<400> SEQUENCE: 36
tgcccggtcg gagtaaacac agaat                                          25

<210> SEQ ID NO 37
<211> LENGTH: 25
<212> TYPE: DNA
<213> ORGANISM: Homo sapiens

<400> SEQUENCE: 37
gatgtcaact gggtcaatgg gggcc                                          25

<210> SEQ ID NO 38
<211> LENGTH: 25
<212> TYPE: DNA
<213> ORGANISM: Homo sapiens

<400> SEQUENCE: 38
gttggctgat attggagtgc tcatt                                          25

<210> SEQ ID NO 39
<211> LENGTH: 25
<212> TYPE: DNA
<213> ORGANISM: Homo sapiens
```

```
<400> SEQUENCE: 39
ccttttgtac ttcactcaga tacta                                      25

<210> SEQ ID NO 40
<211> LENGTH: 25
<212> TYPE: DNA
<213> ORGANISM: Homo sapiens

<400> SEQUENCE: 40
taagcatcct tagggttctg cctct                                      25

<210> SEQ ID NO 41
<211> LENGTH: 25
<212> TYPE: DNA
<213> ORGANISM: Homo sapiens

<400> SEQUENCE: 41
ctcatctccc tcaaggatgg ctacg                                      25

<210> SEQ ID NO 42
<211> LENGTH: 25
<212> TYPE: DNA
<213> ORGANISM: Homo sapiens

<400> SEQUENCE: 42
tgtgaatcat cctgcctttc aaatt                                      25

<210> SEQ ID NO 43
<211> LENGTH: 25
<212> TYPE: DNA
<213> ORGANISM: Homo sapiens

<400> SEQUENCE: 43
tacaaaccac attacttctg tcact                                      25

<210> SEQ ID NO 44
<211> LENGTH: 25
<212> TYPE: DNA
<213> ORGANISM: Homo sapiens

<400> SEQUENCE: 44
gtcccggatc caggacctgg tagca                                      25

<210> SEQ ID NO 45
<211> LENGTH: 25
<212> TYPE: DNA
<213> ORGANISM: Homo sapiens

<400> SEQUENCE: 45
agtgaagagg tcgtcctctc catct                                      25

<210> SEQ ID NO 46
<211> LENGTH: 25
<212> TYPE: DNA
<213> ORGANISM: Homo sapiens

<400> SEQUENCE: 46
gctgaaggca cctactcagt atctt                                      25

<210> SEQ ID NO 47
<211> LENGTH: 25
<212> TYPE: DNA
```

```
<213> ORGANISM: Homo sapiens

<400> SEQUENCE: 47
taagcattcc gtccatctaa gctca                                          25

<210> SEQ ID NO 48
<211> LENGTH: 25
<212> TYPE: DNA
<213> ORGANISM: Homo sapiens

<400> SEQUENCE: 48
tgatggagca taacgggtcc cagcc                                          25

<210> SEQ ID NO 49
<211> LENGTH: 25
<212> TYPE: DNA
<213> ORGANISM: Homo sapiens

<400> SEQUENCE: 49
atgatttctt agggtctgtg tactt                                          25

<210> SEQ ID NO 50
<211> LENGTH: 25
<212> TYPE: DNA
<213> ORGANISM: Homo sapiens

<400> SEQUENCE: 50
gttccatttc tctcattcac aagat                                          25

<210> SEQ ID NO 51
<211> LENGTH: 25
<212> TYPE: DNA
<213> ORGANISM: Homo sapiens

<400> SEQUENCE: 51
gaggccaaga aattccatgt tgttt                                          25

<210> SEQ ID NO 52
<211> LENGTH: 25
<212> TYPE: DNA
<213> ORGANISM: Homo sapiens

<400> SEQUENCE: 52
aaagctgtga atctgttccc tgctg                                          25

<210> SEQ ID NO 53
<211> LENGTH: 25
<212> TYPE: DNA
<213> ORGANISM: Homo sapiens

<400> SEQUENCE: 53
atgagctccc agattcgtca gaatt                                          25

<210> SEQ ID NO 54
<211> LENGTH: 25
<212> TYPE: DNA
<213> ORGANISM: Homo sapiens

<400> SEQUENCE: 54
tccccatcag gaagtcctcg cagaa                                          25

<210> SEQ ID NO 55
<211> LENGTH: 25
```

```
<212> TYPE: DNA
<213> ORGANISM: Homo sapiens

<400> SEQUENCE: 55
tgagtccctg gaacgccaga tgcgt                                   25

<210> SEQ ID NO 56
<211> LENGTH: 25
<212> TYPE: DNA
<213> ORGANISM: Homo sapiens

<400> SEQUENCE: 56
ttagagccag tcttcacact cggaa                                   25

<210> SEQ ID NO 57
<211> LENGTH: 25
<212> TYPE: DNA
<213> ORGANISM: Homo sapiens

<400> SEQUENCE: 57
aaaacttccc cggtatgatg attgt                                   25

<210> SEQ ID NO 58
<211> LENGTH: 25
<212> TYPE: DNA
<213> ORGANISM: Homo sapiens

<400> SEQUENCE: 58
tcagtgggca cagttcttca gctac                                   25

<210> SEQ ID NO 59
<211> LENGTH: 25
<212> TYPE: DNA
<213> ORGANISM: Homo sapiens

<400> SEQUENCE: 59
actagctcat tatttccatc tttgg                                   25

<210> SEQ ID NO 60
<211> LENGTH: 25
<212> TYPE: DNA
<213> ORGANISM: Homo sapiens

<400> SEQUENCE: 60
aattatgagt ttctatctgt gtcca                                   25

<210> SEQ ID NO 61
<211> LENGTH: 25
<212> TYPE: DNA
<213> ORGANISM: Homo sapiens

<400> SEQUENCE: 61
gggaagtcca catagcgtca ttaat                                   25

<210> SEQ ID NO 62
<211> LENGTH: 25
<212> TYPE: DNA
<213> ORGANISM: Homo sapiens

<400> SEQUENCE: 62
ttcagctacc ctgactttct cagga                                   25

<210> SEQ ID NO 63
```

```
<211> LENGTH: 25
<212> TYPE: DNA
<213> ORGANISM: Homo sapiens

<400> SEQUENCE: 63
ggcatgatgt ccggtgattt ctgta                                      25

<210> SEQ ID NO 64
<211> LENGTH: 25
<212> TYPE: DNA
<213> ORGANISM: Homo sapiens

<400> SEQUENCE: 64
actcttgagg gttgattatg ctgca                                      25

<210> SEQ ID NO 65
<211> LENGTH: 25
<212> TYPE: DNA
<213> ORGANISM: Homo sapiens

<400> SEQUENCE: 65
ggacctcatc tctgagctga aacgg                                      25

<210> SEQ ID NO 66
<211> LENGTH: 25
<212> TYPE: DNA
<213> ORGANISM: Homo sapiens

<400> SEQUENCE: 66
gttggtgttt aaagatctga agtgt                                      25

<210> SEQ ID NO 67
<211> LENGTH: 25
<212> TYPE: DNA
<213> ORGANISM: Homo sapiens

<400> SEQUENCE: 67
gaagcaccat aactttgttt agccc                                      25

<210> SEQ ID NO 68
<211> LENGTH: 25
<212> TYPE: DNA
<213> ORGANISM: Homo sapiens

<400> SEQUENCE: 68
acagcatgag gcggccgggg agctg                                      25

<210> SEQ ID NO 69
<211> LENGTH: 25
<212> TYPE: DNA
<213> ORGANISM: Homo sapiens

<400> SEQUENCE: 69
gctatggtta tattagcacc aaact                                      25

<210> SEQ ID NO 70
<211> LENGTH: 25
<212> TYPE: DNA
<213> ORGANISM: Homo sapiens

<400> SEQUENCE: 70
ggccgacaac agctgcatct atgtc                                      25
```

```
<210> SEQ ID NO 71
<211> LENGTH: 25
<212> TYPE: DNA
<213> ORGANISM: Homo sapiens

<400> SEQUENCE: 71
tgaaaaaggg tttctattct ctctg                                    25

<210> SEQ ID NO 72
<211> LENGTH: 25
<212> TYPE: DNA
<213> ORGANISM: Homo sapiens

<400> SEQUENCE: 72
agtatcagtc ggtgcaacag ttggc                                    25

<210> SEQ ID NO 73
<211> LENGTH: 25
<212> TYPE: DNA
<213> ORGANISM: Homo sapiens

<400> SEQUENCE: 73
tgaagttgat cctgagactc ttgaa                                    25

<210> SEQ ID NO 74
<211> LENGTH: 25
<212> TYPE: DNA
<213> ORGANISM: Homo sapiens

<400> SEQUENCE: 74
tactcagagg tgtgaccctc gccag                                    25

<210> SEQ ID NO 75
<211> LENGTH: 25
<212> TYPE: DNA
<213> ORGANISM: Homo sapiens

<400> SEQUENCE: 75
gtcgtactat cttactgagc cacag                                    25

<210> SEQ ID NO 76
<211> LENGTH: 25
<212> TYPE: DNA
<213> ORGANISM: Homo sapiens

<400> SEQUENCE: 76
aaggcgtaac gagttcatct ttctt                                    25

<210> SEQ ID NO 77
<211> LENGTH: 25
<212> TYPE: DNA
<213> ORGANISM: Homo sapiens

<400> SEQUENCE: 77
ccttgatacc agctctctgt ggaaa                                    25

<210> SEQ ID NO 78
<211> LENGTH: 25
<212> TYPE: DNA
<213> ORGANISM: Homo sapiens

<400> SEQUENCE: 78
aaatcactaa acctcgtttt ctcag                                    25
```

<210> SEQ ID NO 79
<211> LENGTH: 25
<212> TYPE: DNA
<213> ORGANISM: Homo sapiens

<400> SEQUENCE: 79
agcgtcctta tctttcagag ctaca                                    25

<210> SEQ ID NO 80
<211> LENGTH: 25
<212> TYPE: DNA
<213> ORGANISM: Homo sapiens

<400> SEQUENCE: 80 aaacccaga cgccatgaaa gctgc                                     25

<210> SEQ ID NO 81
<211> LENGTH: 25
<212> TYPE: DNA
<213> ORGANISM: Homo sapiens

<400> SEQUENCE: 81
gggaacactg ctctcagaca ttaca                                    25

<210> SEQ ID NO 82
<211> LENGTH: 25
<212> TYPE: DNA
<213> ORGANISM: Homo sapiens

<400> SEQUENCE: 82 cttttcctg ggtcatgctg caaca                                     25

<210> SEQ ID NO 83
<211> LENGTH: 25
<212> TYPE: DNA
<213> ORGANISM: Homo sapiens

<400> SEQUENCE: 83
gatggggtgc atgtagtctt tggac                                    25

<210> SEQ ID NO 84
<211> LENGTH: 25
<212> TYPE: DNA
<213> ORGANISM: Homo sapiens

<400> SEQUENCE: 84
gaaggtgtga tctgtgggac tgtct                                    25

<210> SEQ ID NO 85
<211> LENGTH: 25
<212> TYPE: DNA
<213> ORGANISM: Homo sapiens

<400> SEQUENCE: 85
gtacgttttt actcagttca tgcgt                                    25

<210> SEQ ID NO 86
<211> LENGTH: 25
<212> TYPE: DNA
<213> ORGANISM: Homo sapiens

<400> SEQUENCE: 86
gcttctcgtg ctgcacatat ttcct                                    25

<210> SEQ ID NO 87
<211> LENGTH: 25
<212> TYPE: DNA
<213> ORGANISM: Homo sapiens

<400> SEQUENCE: 87
gtgaacagac ttgaaactcc agagc    25

<210> SEQ ID NO 88
<211> LENGTH: 25
<212> TYPE: DNA
<213> ORGANISM: Homo sapiens

<400> SEQUENCE: 88
atcattttca ggcttctgca gctgt    25

<210> SEQ ID NO 89
<211> LENGTH: 25
<212> TYPE: DNA
<213> ORGANISM: Homo sapiens

<400> SEQUENCE: 89
gcatgttgtt tgccaggaca ctgtg    25

<210> SEQ ID NO 90
<211> LENGTH: 25
<212> TYPE: DNA
<213> ORGANISM: Homo sapiens

<400> SEQUENCE: 90
ttgtgcttgc tcttcagatg gatgg    25

<210> SEQ ID NO 91
<211> LENGTH: 25
<212> TYPE: DNA
<213> ORGANISM: Homo sapiens

<400> SEQUENCE: 91
tagccaggat ccttggtgtc ctagg    25

<210> SEQ ID NO 92
<211> LENGTH: 25
<212> TYPE: DNA
<213> ORGANISM: Homo sapiens

<400> SEQUENCE: 92
gcggcgtgta taccaatgca tggcc    25

<210> SEQ ID NO 93
<211> LENGTH: 25
<212> TYPE: DNA
<213> ORGANISM: Homo sapiens

<400> SEQUENCE: 93
gaataacttt tggctgttgt gctaa    25

<210> SEQ ID NO 94
<211> LENGTH: 25
<212> TYPE: DNA
<213> ORGANISM: Homo sapiens

<400> SEQUENCE: 94
tggcccgcgt gattgtggca tttaa    25

<210> SEQ ID NO 95
<211> LENGTH: 25
<212> TYPE: DNA
<213> ORGANISM: Homo sapiens

<400> SEQUENCE: 95
cataactgtt agacttcccg tttct    25

<210> SEQ ID NO 96
<211> LENGTH: 25
<212> TYPE: DNA
<213> ORGANISM: Homo sapiens

<400> SEQUENCE: 96
tcaataaagt tccctgtga cactc    25

<210> SEQ ID NO 97
<211> LENGTH: 25
<212> TYPE: DNA
<213> ORGANISM: Homo sapiens

<400> SEQUENCE: 97
ctcccctatg atgggcggct actgg    25

<210> SEQ ID NO 98
<211> LENGTH: 25
<212> TYPE: DNA
<213> ORGANISM: Homo sapiens

<400> SEQUENCE: 98
atcagttgat tcttgtgcca ttttt    25

<210> SEQ ID NO 99
<211> LENGTH: 25
<212> TYPE: DNA
<213> ORGANISM: Homo sapiens

<400> SEQUENCE: 99
tgagccagtg agggcagtcc tgcaa    25

<210> SEQ ID NO 100
<211> LENGTH: 25
<212> TYPE: DNA
<213> ORGANISM: Homo sapiens

<400> SEQUENCE: 100
gcatcatcac catagagtcc cagga    25

<210> SEQ ID NO 101
<211> LENGTH: 25
<212> TYPE: DNA
<213> ORGANISM: Homo sapiens

<400> SEQUENCE: 101
tcttgctcca aagggctccg tggag    25

<210> SEQ ID NO 102
<211> LENGTH: 25
<212> TYPE: DNA
<213> ORGANISM: Homo sapiens

<400> SEQUENCE: 102
atacgccctt ggcacagtcg gatga					25

<210> SEQ ID NO 103
<211> LENGTH: 25
<212> TYPE: DNA
<213> ORGANISM: Homo sapiens

<400> SEQUENCE: 103
gtctgctggg tgtgaccatg tttcc					25

<210> SEQ ID NO 104
<211> LENGTH: 25
<212> TYPE: DNA
<213> ORGANISM: Homo sapiens

<400> SEQUENCE: 104
gtgcgtggga cgaagacatc tttga					25

<210> SEQ ID NO 105
<211> LENGTH: 25
<212> TYPE: DNA
<213> ORGANISM: Homo sapiens

<400> SEQUENCE: 105
tggtcccctt cacctgggag aaaag					25

<210> SEQ ID NO 106
<211> LENGTH: 25
<212> TYPE: DNA
<213> ORGANISM: Homo sapiens

<400> SEQUENCE: 106
gggccaagca ggacatggcg cggca					25

<210> SEQ ID NO 107
<211> LENGTH: 25
<212> TYPE: DNA
<213> ORGANISM: Homo sapiens

<400> SEQUENCE: 107
agcttcagac tcaagtaccc attct					25

<210> SEQ ID NO 108
<211> LENGTH: 25
<212> TYPE: DNA
<213> ORGANISM: Homo sapiens

<400> SEQUENCE: 108
gagctgctga gacgacgctc acaga					25

<210> SEQ ID NO 109
<211> LENGTH: 25
<212> TYPE: DNA
<213> ORGANISM: Homo sapiens

<400> SEQUENCE: 109
gagaagcagt ttgacggacc ttgtg					25

<210> SEQ ID NO 110
<211> LENGTH: 25
<212> TYPE: DNA
<213> ORGANISM: Homo sapiens

```
<400> SEQUENCE: 110
ggtgattctg agcgagatct tcctg                                           25

<210> SEQ ID NO 111
<211> LENGTH: 25
<212> TYPE: DNA
<213> ORGANISM: Homo sapiens

<400> SEQUENCE: 111
gcagccttgg aaacctaacc tgcct                                           25

<210> SEQ ID NO 112
<211> LENGTH: 25
<212> TYPE: DNA
<213> ORGANISM: Homo sapiens

<400> SEQUENCE: 112
cctgcagcac cgacgtgtgt gacag                                           25

<210> SEQ ID NO 113
<211> LENGTH: 25
<212> TYPE: DNA
<213> ORGANISM: Homo sapiens

<400> SEQUENCE: 113
acttggctca gtggaagccc tcttt                                           25

<210> SEQ ID NO 114
<211> LENGTH: 25
<212> TYPE: DNA
<213> ORGANISM: Homo sapiens

<400> SEQUENCE: 114
acattgcccg gaaactcagt ctatt                                           25

<210> SEQ ID NO 115
<211> LENGTH: 25
<212> TYPE: DNA
<213> ORGANISM: Homo sapiens

<400> SEQUENCE: 115
gctgtggatc tgtttggcca gggtc                                           25

<210> SEQ ID NO 116
<211> LENGTH: 25
<212> TYPE: DNA
<213> ORGANISM: Homo sapiens

<400> SEQUENCE: 116
gttagagccg atatcactgg aagat                                           25

<210> SEQ ID NO 117
<211> LENGTH: 25
<212> TYPE: DNA
<213> ORGANISM: Homo sapiens

<400> SEQUENCE: 117
agatttgtca gccctatctc aaact                                           25

<210> SEQ ID NO 118
<211> LENGTH: 25
<212> TYPE: DNA
<213> ORGANISM: Homo sapiens
```

```
<400> SEQUENCE: 118
aggtcttccc agaggctgga tacca                                        25

<210> SEQ ID NO 119
<211> LENGTH: 25
<212> TYPE: DNA
<213> ORGANISM: Homo sapiens

<400> SEQUENCE: 119
gtcttcccta cctcaggcag gaagg                                        25

<210> SEQ ID NO 120
<211> LENGTH: 25
<212> TYPE: DNA
<213> ORGANISM: Homo sapiens

<400> SEQUENCE: 120
ctacccttat gatgacccat tttcc                                        25

<210> SEQ ID NO 121
<211> LENGTH: 25
<212> TYPE: DNA
<213> ORGANISM: Homo sapiens

<400> SEQUENCE: 121
aaatgctctt atttttccaa cagct                                        25

<210> SEQ ID NO 122
<211> LENGTH: 25
<212> TYPE: DNA
<213> ORGANISM: Homo sapiens

<400> SEQUENCE: 122
gtgtatagtg ttttaccctc ttctt                                        25

<210> SEQ ID NO 123
<211> LENGTH: 25
<212> TYPE: DNA
<213> ORGANISM: Homo sapiens

<400> SEQUENCE: 123
tcatcaaggg ctatgtgcct cccac                                        25

<210> SEQ ID NO 124
<211> LENGTH: 25
<212> TYPE: DNA
<213> ORGANISM: Homo sapiens

<400> SEQUENCE: 124
ccccgcacca gatcaagtag tttgg                                        25

<210> SEQ ID NO 125
<211> LENGTH: 25
<212> TYPE: DNA
<213> ORGANISM: Homo sapiens

<400> SEQUENCE: 125
ccctcctacc agatgacaca gacaa                                        25

<210> SEQ ID NO 126
<211> LENGTH: 25
<212> TYPE: DNA
```

```
<213> ORGANISM: Homo sapiens

<400> SEQUENCE: 126
tgtatggttt tcacctggac accgt                                          25

<210> SEQ ID NO 127
<211> LENGTH: 25
<212> TYPE: DNA
<213> ORGANISM: Homo sapiens

<400> SEQUENCE: 127
aactccgtct gtctactgtg tgaga                                          25

<210> SEQ ID NO 128
<211> LENGTH: 25
<212> TYPE: DNA
<213> ORGANISM: Homo sapiens

<400> SEQUENCE: 128
cccactggcc tgaatctaca ctgga                                          25

<210> SEQ ID NO 129
<211> LENGTH: 25
<212> TYPE: DNA
<213> ORGANISM: Homo sapiens

<400> SEQUENCE: 129
acattacatc cgtggattct cctgc                                          25

<210> SEQ ID NO 130
<211> LENGTH: 25
<212> TYPE: DNA
<213> ORGANISM: Homo sapiens

<400> SEQUENCE: 130
ggccctgggc cagggtgatt ggact                                          25

<210> SEQ ID NO 131
<211> LENGTH: 25
<212> TYPE: DNA
<213> ORGANISM: Homo sapiens

<400> SEQUENCE: 131
tttagccctc atgactgtat tttct                                          25

<210> SEQ ID NO 132
<211> LENGTH: 25
<212> TYPE: DNA
<213> ORGANISM: Homo sapiens

<400> SEQUENCE: 132
acacgctgca gatcgaggac tttct                                          25

<210> SEQ ID NO 133
<211> LENGTH: 25
<212> TYPE: DNA
<213> ORGANISM: Homo sapiens

<400> SEQUENCE: 133
accggcagcc ctggaagggg cactt                                          25

<210> SEQ ID NO 134
<211> LENGTH: 25
```

```
<212> TYPE: DNA
<213> ORGANISM: Homo sapiens

<400> SEQUENCE: 134
taccagcagg aggttctggg cctct                                   25

<210> SEQ ID NO 135
<211> LENGTH: 25
<212> TYPE: DNA
<213> ORGANISM: Homo sapiens

<400> SEQUENCE: 135
catctttcag ggctgccagt ttcgc                                   25

<210> SEQ ID NO 136
<211> LENGTH: 25
<212> TYPE: DNA
<213> ORGANISM: Homo sapiens

<400> SEQUENCE: 136
gggctacgcc aaggactttg accct                                   25

<210> SEQ ID NO 137
<211> LENGTH: 25
<212> TYPE: DNA
<213> ORGANISM: Homo sapiens

<400> SEQUENCE: 137
aatctagtca cctaaccttg tggtt                                   25

<210> SEQ ID NO 138
<211> LENGTH: 25
<212> TYPE: DNA
<213> ORGANISM: Homo sapiens

<400> SEQUENCE: 138
atttcaaaat ttctgcattc acgga                                   25

<210> SEQ ID NO 139
<211> LENGTH: 25
<212> TYPE: DNA
<213> ORGANISM: Homo sapiens

<400> SEQUENCE: 139
aacacctgtc cattgaagat ttcac                                   25

<210> SEQ ID NO 140
<211> LENGTH: 25
<212> TYPE: DNA
<213> ORGANISM: Homo sapiens

<400> SEQUENCE: 140
gacattctta tgcttctttt acaac                                   25

<210> SEQ ID NO 141
<211> LENGTH: 25
<212> TYPE: DNA
<213> ORGANISM: Homo sapiens

<400> SEQUENCE: 141
aatgtttcct aacagttgtg atgtt                                   25

<210> SEQ ID NO 142
```

-continued

```
<211> LENGTH: 25
<212> TYPE: DNA
<213> ORGANISM: Homo sapiens

<400> SEQUENCE: 142
gggtgaagag agactcggtg cgggc                                              25

<210> SEQ ID NO 143
<211> LENGTH: 25
<212> TYPE: DNA
<213> ORGANISM: Homo sapiens

<400> SEQUENCE: 143
cgaccgcctg tatgtttgtg taatt                                              25

<210> SEQ ID NO 144
<211> LENGTH: 25
<212> TYPE: DNA
<213> ORGANISM: Homo sapiens

<400> SEQUENCE: 144
aaggcctatc agcttctatc agccc                                              25

<210> SEQ ID NO 145
<211> LENGTH: 25
<212> TYPE: DNA
<213> ORGANISM: Homo sapiens

<400> SEQUENCE: 145
gtcactggtc tgtttgcatt tgata                                              25

<210> SEQ ID NO 146
<211> LENGTH: 25
<212> TYPE: DNA
<213> ORGANISM: Homo sapiens

<400> SEQUENCE: 146
agctcaaaac ttgctaggca tcaga                                              25

<210> SEQ ID NO 147
<211> LENGTH: 25
<212> TYPE: DNA
<213> ORGANISM: Homo sapiens

<400> SEQUENCE: 147
gcagcaaagc tggctccaac atgct                                              25

<210> SEQ ID NO 148
<211> LENGTH: 25
<212> TYPE: DNA
<213> ORGANISM: Homo sapiens

<400> SEQUENCE: 148
aaacactatc tacttccttt gtcat                                              25

<210> SEQ ID NO 149
<211> LENGTH: 25
<212> TYPE: DNA
<213> ORGANISM: Homo sapiens

<400> SEQUENCE: 149
gaggatcatg cccttagcaa gtact                                              25
```

```
<210> SEQ ID NO 150
<211> LENGTH: 25
<212> TYPE: DNA
<213> ORGANISM: Homo sapiens

<400> SEQUENCE: 150
aacatcattt tagcaaaggc cagga                                         25

<210> SEQ ID NO 151
<211> LENGTH: 25
<212> TYPE: DNA
<213> ORGANISM: Homo sapiens

<400> SEQUENCE: 151
tgtccttgtt acattgaggt taaga                                         25

<210> SEQ ID NO 152
<211> LENGTH: 25
<212> TYPE: DNA
<213> ORGANISM: Homo sapiens

<400> SEQUENCE: 152
tccctactgc atggggactt ccacg                                         25

<210> SEQ ID NO 153
<211> LENGTH: 25
<212> TYPE: DNA
<213> ORGANISM: Homo sapiens

<400> SEQUENCE: 153
ccaccttcac ctcggaggga cggag                                         25

<210> SEQ ID NO 154
<211> LENGTH: 25
<212> TYPE: DNA
<213> ORGANISM: Homo sapiens

<400> SEQUENCE: 154
taattacacg ttcaccgtcc aagca                                         25

<210> SEQ ID NO 155
<211> LENGTH: 25
<212> TYPE: DNA
<213> ORGANISM: Homo sapiens

<400> SEQUENCE: 155
ttccctttct accattgatt taaat                                         25

<210> SEQ ID NO 156
<211> LENGTH: 25
<212> TYPE: DNA
<213> ORGANISM: Homo sapiens

<400> SEQUENCE: 156
agtactggtt gaacctgacc acttc                                         25

<210> SEQ ID NO 157
<211> LENGTH: 25
<212> TYPE: DNA
<213> ORGANISM: Homo sapiens

<400> SEQUENCE: 157
aaatacataa gctagtttct gttct                                         25
```

```
<210> SEQ ID NO 158
<211> LENGTH: 25
<212> TYPE: DNA
<213> ORGANISM: Homo sapiens

<400> SEQUENCE: 158
gtaacgtgat tgattcagta tctta                                25

<210> SEQ ID NO 159
<211> LENGTH: 25
<212> TYPE: DNA
<213> ORGANISM: Homo sapiens

<400> SEQUENCE: 159
aatacatccg atgcgtagat tcttg                                25

<210> SEQ ID NO 160
<211> LENGTH: 25
<212> TYPE: DNA
<213> ORGANISM: Homo sapiens

<400> SEQUENCE: 160
agaatgctcg ggtgctagac tggat                                25

<210> SEQ ID NO 161
<211> LENGTH: 25
<212> TYPE: DNA
<213> ORGANISM: Homo sapiens

<400> SEQUENCE: 161
ggacggactc tatgaggggc tcaca                                25

<210> SEQ ID NO 162
<211> LENGTH: 25
<212> TYPE: DNA
<213> ORGANISM: Homo sapiens

<400> SEQUENCE: 162
ggaatgactc aaatgcccaa aacca                                25

<210> SEQ ID NO 163
<211> LENGTH: 25
<212> TYPE: DNA
<213> ORGANISM: Homo sapiens

<400> SEQUENCE: 163
tcctctcagc tcctaaagca caact                                25

<210> SEQ ID NO 164
<211> LENGTH: 25
<212> TYPE: DNA
<213> ORGANISM: Homo sapiens

<400> SEQUENCE: 164
acatgttcgc acccaagtgt ggcgg                                25

<210> SEQ ID NO 165
<211> LENGTH: 25
<212> TYPE: DNA
<213> ORGANISM: Homo sapiens

<400> SEQUENCE: 165
tttcagatgg agtaccagca ccgaa                                25
```

<210> SEQ ID NO 166
<211> LENGTH: 25
<212> TYPE: DNA
<213> ORGANISM: Homo sapiens

<400> SEQUENCE: 166
tggcactcgc ggttggagtc agcga                                          25

<210> SEQ ID NO 167
<211> LENGTH: 25
<212> TYPE: DNA
<213> ORGANISM: Homo sapiens

<400> SEQUENCE: 167
ggccatctat gggactgaac tttga                                          25

<210> SEQ ID NO 168
<211> LENGTH: 25
<212> TYPE: DNA
<213> ORGANISM: Homo sapiens

<400> SEQUENCE: 168
gaagaaactg gacaccaaca gtgat                                          25

<210> SEQ ID NO 169
<211> LENGTH: 25
<212> TYPE: DNA
<213> ORGANISM: Homo sapiens

<400> SEQUENCE: 169
gctgtagcca gtgcagacct cactg                                          25

<210> SEQ ID NO 170
<211> LENGTH: 25
<212> TYPE: DNA
<213> ORGANISM: Homo sapiens

<400> SEQUENCE: 170
aggtgtccag tacctaatca cgctc                                          25

<210> SEQ ID NO 171
<211> LENGTH: 25
<212> TYPE: DNA
<213> ORGANISM: Homo sapiens

<400> SEQUENCE: 171
ttgccgtgat gaccgtggct atcct                                          25

<210> SEQ ID NO 172
<211> LENGTH: 25
<212> TYPE: DNA
<213> ORGANISM: Homo sapiens

<400> SEQUENCE: 172
gaatacgtta ggagccagta cccca                                          25

<210> SEQ ID NO 173
<211> LENGTH: 25
<212> TYPE: DNA
<213> ORGANISM: Homo sapiens

<400> SEQUENCE: 173
gaagctgctc aacaaagtgt ggaag                                              25

<210> SEQ ID NO 174
<211> LENGTH: 25
<212> TYPE: DNA
<213> ORGANISM: Homo sapiens

<400> SEQUENCE: 174
ggaatgtccc agacagacct gtctc                                              25

<210> SEQ ID NO 175
<211> LENGTH: 25
<212> TYPE: DNA
<213> ORGANISM: Homo sapiens

<400> SEQUENCE: 175
ccttcatgga cgtcaacagc acctg                                              25

<210> SEQ ID NO 176
<211> LENGTH: 25
<212> TYPE: DNA
<213> ORGANISM: Homo sapiens

<400> SEQUENCE: 176
ggcccggata tggctcgtgg acagc                                              25

<210> SEQ ID NO 177
<211> LENGTH: 25
<212> TYPE: DNA
<213> ORGANISM: Homo sapiens

<400> SEQUENCE: 177
aggagtctcc accagaggga ggctc                                              25

<210> SEQ ID NO 178
<211> LENGTH: 25
<212> TYPE: DNA
<213> ORGANISM: Homo sapiens

<400> SEQUENCE: 178
gagcaccact actgctgcat tgtgc                                              25

<210> SEQ ID NO 179
<211> LENGTH: 25
<212> TYPE: DNA
<213> ORGANISM: Homo sapiens

<400> SEQUENCE: 179
actctgacat ttcttgttct caagc                                              25

<210> SEQ ID NO 180
<211> LENGTH: 25
<212> TYPE: DNA
<213> ORGANISM: Homo sapiens

<400> SEQUENCE: 180
ccagcatttc cagagcagag cctac                                              25

<210> SEQ ID NO 181
<211> LENGTH: 25
<212> TYPE: DNA
<213> ORGANISM: Homo sapiens

<400> SEQUENCE: 181

```
gcgtgtcttg agttccatgc aaatt                                                25

<210> SEQ ID NO 182
<211> LENGTH: 25
<212> TYPE: DNA
<213> ORGANISM: Homo sapiens

<400> SEQUENCE: 182
aatggtgaca gtccaaacca ctcca                                                25

<210> SEQ ID NO 183
<211> LENGTH: 25
<212> TYPE: DNA
<213> ORGANISM: Homo sapiens

<400> SEQUENCE: 183
ggccctgcat gtcagatggc gtggt                                                25

<210> SEQ ID NO 184
<211> LENGTH: 25
<212> TYPE: DNA
<213> ORGANISM: Homo sapiens

<400> SEQUENCE: 184
tgatcataaa ttctccccaa ctata                                                25

<210> SEQ ID NO 185
<211> LENGTH: 25
<212> TYPE: DNA
<213> ORGANISM: Homo sapiens

<400> SEQUENCE: 185
aaagttgcca agatgctcct tgttg                                                25

<210> SEQ ID NO 186
<211> LENGTH: 25
<212> TYPE: DNA
<213> ORGANISM: Homo sapiens

<400> SEQUENCE: 186
gtctcaccca actgcagttt actat                                                25

<210> SEQ ID NO 187
<211> LENGTH: 25
<212> TYPE: DNA
<213> ORGANISM: Homo sapiens

<400> SEQUENCE: 187
gacggagttc ctaagcttca tgaat                                                25

<210> SEQ ID NO 188
<211> LENGTH: 25
<212> TYPE: DNA
<213> ORGANISM: Homo sapiens

<400> SEQUENCE: 188
tcagcctggg cagtcttacc aaaat                                                25

<210> SEQ ID NO 189
<211> LENGTH: 25
<212> TYPE: DNA
<213> ORGANISM: Homo sapiens
```

```
<400> SEQUENCE: 189
tgctgtggct tcaccaacta tacgg                                   25

<210> SEQ ID NO 190
<211> LENGTH: 25
<212> TYPE: DNA
<213> ORGANISM: Homo sapiens

<400> SEQUENCE: 190
ccttgactcc tttggtattt cactg                                   25

<210> SEQ ID NO 191
<211> LENGTH: 25
<212> TYPE: DNA
<213> ORGANISM: Homo sapiens

<400> SEQUENCE: 191
acagcaggca tcgcaacttt ctgca                                   25

<210> SEQ ID NO 192
<211> LENGTH: 25
<212> TYPE: DNA
<213> ORGANISM: Homo sapiens

<400> SEQUENCE: 192
caagagctac aatgtcacct ccgtc                                   25

<210> SEQ ID NO 193
<211> LENGTH: 25
<212> TYPE: DNA
<213> ORGANISM: Homo sapiens

<400> SEQUENCE: 193
gtttgtctct tgttgttctg aagga                                   25

<210> SEQ ID NO 194
<211> LENGTH: 25
<212> TYPE: DNA
<213> ORGANISM: Homo sapiens

<400> SEQUENCE: 194
ctctctagtt agatatctga cttgg                                   25

<210> SEQ ID NO 195
<211> LENGTH: 25
<212> TYPE: DNA
<213> ORGANISM: Homo sapiens

<400> SEQUENCE: 195
tccagcctcg gggtgtaggt ttctg                                   25

<210> SEQ ID NO 196
<211> LENGTH: 25
<212> TYPE: DNA
<213> ORGANISM: Homo sapiens

<400> SEQUENCE: 196
actcgtctca cgccgtgttt gagat                                   25

<210> SEQ ID NO 197
<211> LENGTH: 25
<212> TYPE: DNA
<213> ORGANISM: Homo sapiens
```

<400> SEQUENCE: 197
gccagagttc aaatgtgact ccacc					25

<210> SEQ ID NO 198
<211> LENGTH: 25
<212> TYPE: DNA
<213> ORGANISM: Homo sapiens

<400> SEQUENCE: 198
caagcccctg tattttgctg atcgg					25

<210> SEQ ID NO 199
<211> LENGTH: 25
<212> TYPE: DNA
<213> ORGANISM: Homo sapiens

<400> SEQUENCE: 199
agaccacaga tatcttctag acata					25

<210> SEQ ID NO 200
<211> LENGTH: 25
<212> TYPE: DNA
<213> ORGANISM: Homo sapiens

<400> SEQUENCE: 200
gtcactgtaa atcattctta agccc					25

<210> SEQ ID NO 201
<211> LENGTH: 25
<212> TYPE: DNA
<213> ORGANISM: Homo sapiens

<400> SEQUENCE: 201
aaggctgtca gggcttctgt ttgtt					25

<210> SEQ ID NO 202
<211> LENGTH: 25
<212> TYPE: DNA
<213> ORGANISM: Homo sapiens

<400> SEQUENCE: 202
gtagacacct gcacgcatag gattg					25

<210> SEQ ID NO 203
<211> LENGTH: 25
<212> TYPE: DNA
<213> ORGANISM: Homo sapiens

<400> SEQUENCE: 203
ttgccacttt cttgcgatat gctgt					25

<210> SEQ ID NO 204
<211> LENGTH: 25
<212> TYPE: DNA
<213> ORGANISM: Homo sapiens

<400> SEQUENCE: 204
gccattccag aagtagctta tccta					25

<210> SEQ ID NO 205
<211> LENGTH: 25
<212> TYPE: DNA

```
<213> ORGANISM: Homo sapiens

<400> SEQUENCE: 205
ccaatacccc accgtgatga cttga                                              25

<210> SEQ ID NO 206
<211> LENGTH: 25
<212> TYPE: DNA
<213> ORGANISM: Homo sapiens

<400> SEQUENCE: 206
aattctctgt tatctttacg aggta                                              25

<210> SEQ ID NO 207
<211> LENGTH: 25
<212> TYPE: DNA
<213> ORGANISM: Homo sapiens

<400> SEQUENCE: 207
cacgagaagg actatgacag cctgg                                              25

<210> SEQ ID NO 208
<211> LENGTH: 25
<212> TYPE: DNA
<213> ORGANISM: Homo sapiens

<400> SEQUENCE: 208
tgatttgcca caatgtcctt aactc                                              25

<210> SEQ ID NO 209
<211> LENGTH: 25
<212> TYPE: DNA
<213> ORGANISM: Homo sapiens

<400> SEQUENCE: 209
gctgaaggca cctactcagt atctt                                              25

<210> SEQ ID NO 210
<211> LENGTH: 25
<212> TYPE: DNA
<213> ORGANISM: Homo sapiens

<400> SEQUENCE: 210
agacctggca cttcagtaac tcagc                                              25

<210> SEQ ID NO 211
<211> LENGTH: 25
<212> TYPE: DNA
<213> ORGANISM: Homo sapiens

<400> SEQUENCE: 211
gactcttgaa gtaatggctg atcct                                              25

<210> SEQ ID NO 212
<211> LENGTH: 25
<212> TYPE: DNA
<213> ORGANISM: Homo sapiens

<400> SEQUENCE: 212
gggactttgt caactgcagt acact                                              25

<210> SEQ ID NO 213
<211> LENGTH: 25
```

<212> TYPE: DNA
<213> ORGANISM: Homo sapiens

<400> SEQUENCE: 213
cctttcttta ctccatcatg gctgg                                    25

<210> SEQ ID NO 214
<211> LENGTH: 25
<212> TYPE: DNA
<213> ORGANISM: Homo sapiens

<400> SEQUENCE: 214
atcactaaca ggtctttgac tcagg                                    25

<210> SEQ ID NO 215
<211> LENGTH: 25
<212> TYPE: DNA
<213> ORGANISM: Homo sapiens

<400> SEQUENCE: 215
gaattcatgg tatcctggtt atttt                                    25

<210> SEQ ID NO 216
<211> LENGTH: 25
<212> TYPE: DNA
<213> ORGANISM: Homo sapiens

<400> SEQUENCE: 216
aactactgtg aaattctacc agcat                                    25

<210> SEQ ID NO 217
<211> LENGTH: 25
<212> TYPE: DNA
<213> ORGANISM: Homo sapiens

<400> SEQUENCE: 217
gacacctgag cctggatttt cactc                                    25

<210> SEQ ID NO 218
<211> LENGTH: 25
<212> TYPE: DNA
<213> ORGANISM: Homo sapiens

<400> SEQUENCE: 218
tcaaacggcc gaagttgcct ctttt                                    25

<210> SEQ ID NO 219
<211> LENGTH: 25
<212> TYPE: DNA
<213> ORGANISM: Homo sapiens

<400> SEQUENCE: 219
atactaggcc tgtctgtggc attct                                    25

<210> SEQ ID NO 220
<211> LENGTH: 25
<212> TYPE: DNA
<213> ORGANISM: Homo sapiens

<400> SEQUENCE: 220
ggatttagga taagctgtca cccag                                    25

<210> SEQ ID NO 221

```
<211> LENGTH: 25
<212> TYPE: DNA
<213> ORGANISM: Homo sapiens

<400> SEQUENCE: 221
ggtcagcaac ctcttttgat tttgt                                    25

<210> SEQ ID NO 222
<211> LENGTH: 25
<212> TYPE: DNA
<213> ORGANISM: Homo sapiens

<400> SEQUENCE: 222
gacaggtgaa catttccgcc tggtc                                    25

<210> SEQ ID NO 223
<211> LENGTH: 25
<212> TYPE: DNA
<213> ORGANISM: Homo sapiens

<400> SEQUENCE: 223
gattcctgaa ctcaaggtac cagca                                    25

<210> SEQ ID NO 224
<211> LENGTH: 25
<212> TYPE: DNA
<213> ORGANISM: Homo sapiens

<400> SEQUENCE: 224
tgttcctttt tgttcaaagt ctatt                                    25

<210> SEQ ID NO 225
<211> LENGTH: 25
<212> TYPE: DNA
<213> ORGANISM: Homo sapiens

<400> SEQUENCE: 225
aggtgttcga aatccgcacc actga                                    25

<210> SEQ ID NO 226
<211> LENGTH: 25
<212> TYPE: DNA
<213> ORGANISM: Homo sapiens

<400> SEQUENCE: 226
gtggagttga tgactttctg ttttc                                    25

<210> SEQ ID NO 227
<211> LENGTH: 25
<212> TYPE: DNA
<213> ORGANISM: Homo sapiens

<400> SEQUENCE: 227
tgcaggtcat gcacacagtt ttgat                                    25

<210> SEQ ID NO 228
<211> LENGTH: 25
<212> TYPE: DNA
<213> ORGANISM: Homo sapiens

<400> SEQUENCE: 228
gctccagaag cgcttggaca ggctg                                    25
```

```
<210> SEQ ID NO 229
<211> LENGTH: 25
<212> TYPE: DNA
<213> ORGANISM: Homo sapiens

<400> SEQUENCE: 229
ggcataatgg caaatccttc aagca                                       25

<210> SEQ ID NO 230
<211> LENGTH: 25
<212> TYPE: DNA
<213> ORGANISM: Homo sapiens

<400> SEQUENCE: 230
ccccatagag acccaagttc tgcgg                                       25

<210> SEQ ID NO 231
<211> LENGTH: 25
<212> TYPE: DNA
<213> ORGANISM: Homo sapiens

<400> SEQUENCE: 231
gtaaaccaca tcttttttgc acttt                                       25

<210> SEQ ID NO 232
<211> LENGTH: 25
<212> TYPE: DNA
<213> ORGANISM: Homo sapiens

<400> SEQUENCE: 232 cacttttgt atttatcgtt tcata                                        25

<210> SEQ ID NO 233
<211> LENGTH: 25
<212> TYPE: DNA
<213> ORGANISM: Homo sapiens

<400> SEQUENCE: 233
gacgcaggac gagctcagtt gtaga                                       25

<210> SEQ ID NO 234
<211> LENGTH: 25
<212> TYPE: DNA
<213> ORGANISM: Homo sapiens

<400> SEQUENCE: 234
tgttgtgcag tgtgcctgtc actac                                       25

<210> SEQ ID NO 235
<211> LENGTH: 25
<212> TYPE: DNA
<213> ORGANISM: Homo sapiens

<400> SEQUENCE: 235
cacttactga ctttgcattt tcgtt                                       25

<210> SEQ ID NO 236
<211> LENGTH: 25
<212> TYPE: DNA
<213> ORGANISM: Homo sapiens

<400> SEQUENCE: 236
ggtggtttct cttgagactc gttac                                       25
```

```
<210> SEQ ID NO 237
<211> LENGTH: 25
<212> TYPE: DNA
<213> ORGANISM: Homo sapiens

<400> SEQUENCE: 237
ttggcagttg cattagtaac tttga                                25

<210> SEQ ID NO 238
<211> LENGTH: 25
<212> TYPE: DNA
<213> ORGANISM: Homo sapiens

<400> SEQUENCE: 238
tcatgtgcac atgccgttgc agcac                                25

<210> SEQ ID NO 239
<211> LENGTH: 25
<212> TYPE: DNA
<213> ORGANISM: Homo sapiens

<400> SEQUENCE: 239
cgttggagaa ctgcagctgc tgtgc                                25

<210> SEQ ID NO 240
<211> LENGTH: 25
<212> TYPE: DNA
<213> ORGANISM: Homo sapiens

<400> SEQUENCE: 240
agcagctgag gtctcttgag ggagc                                25

<210> SEQ ID NO 241
<211> LENGTH: 25
<212> TYPE: DNA
<213> ORGANISM: Homo sapiens

<400> SEQUENCE: 241
cattggcctg agtttcttgt gcatt                                25

<210> SEQ ID NO 242
<211> LENGTH: 25
<212> TYPE: DNA
<213> ORGANISM: Homo sapiens

<400> SEQUENCE: 242
gagcctacct ggagggcgag tgcgt                                25

<210> SEQ ID NO 243
<211> LENGTH: 25
<212> TYPE: DNA
<213> ORGANISM: Homo sapiens

<400> SEQUENCE: 243
gttttcaatt ttgcatgctc gatta                                25

<210> SEQ ID NO 244
<211> LENGTH: 25
<212> TYPE: DNA
<213> ORGANISM: Homo sapiens

<400> SEQUENCE: 244
ttatgtgtac attattgttg ctatt                                25
```

<210> SEQ ID NO 245
<211> LENGTH: 25
<212> TYPE: DNA
<213> ORGANISM: Homo sapiens

<400> SEQUENCE: 245
cttcccggtc actggtaaca atagc                                       25

<210> SEQ ID NO 246
<211> LENGTH: 25
<212> TYPE: DNA
<213> ORGANISM: Homo sapiens

<400> SEQUENCE: 246
gtacctgtgg gttagcatca agttc                                       25

<210> SEQ ID NO 247
<211> LENGTH: 25
<212> TYPE: DNA
<213> ORGANISM: Homo sapiens

<400> SEQUENCE: 247
ctgagagcct acctggaggg cctgt                                       25

<210> SEQ ID NO 248
<211> LENGTH: 25
<212> TYPE: DNA
<213> ORGANISM: Homo sapiens

<400> SEQUENCE: 248
ttgggccttt tatctgtcta tccat                                       25

<210> SEQ ID NO 249
<211> LENGTH: 25
<212> TYPE: DNA
<213> ORGANISM: Homo sapiens

<400> SEQUENCE: 249
cagtgtgaca agtgccggga gatct                                       25

<210> SEQ ID NO 250
<211> LENGTH: 25
<212> TYPE: DNA
<213> ORGANISM: Homo sapiens

<400> SEQUENCE: 250
agaatctttt ctatgcctct attcc                                       25

<210> SEQ ID NO 251
<211> LENGTH: 25
<212> TYPE: DNA
<213> ORGANISM: Homo sapiens

<400> SEQUENCE: 251
gccatatagc aggcacgtcc gggtc                                       25

<210> SEQ ID NO 252
<211> LENGTH: 25
<212> TYPE: DNA
<213> ORGANISM: Homo sapiens

<400> SEQUENCE: 252
ggcaagggat aactcttcta acaca                                          25

<210> SEQ ID NO 253
<211> LENGTH: 25
<212> TYPE: DNA
<213> ORGANISM: Homo sapiens

<400> SEQUENCE: 253
ttccctcctt atagtcaagg accgt                                          25

<210> SEQ ID NO 254
<211> LENGTH: 25
<212> TYPE: DNA
<213> ORGANISM: Homo sapiens

<400> SEQUENCE: 254
aataacgcaa atggcttcct cttc                                           25

<210> SEQ ID NO 255
<211> LENGTH: 25
<212> TYPE: DNA
<213> ORGANISM: Homo sapiens

<400> SEQUENCE: 255
ggcctagcac ggacatggtc tgtcc                                          25

<210> SEQ ID NO 256
<211> LENGTH: 25
<212> TYPE: DNA
<213> ORGANISM: Homo sapiens

<400> SEQUENCE: 256
tgatggacga atgccttttc cggtg                                          25

<210> SEQ ID NO 257
<211> LENGTH: 25
<212> TYPE: DNA
<213> ORGANISM: Homo sapiens

<400> SEQUENCE: 257
gatcctctgc aatgtgcttg aaaac                                          25

<210> SEQ ID NO 258
<211> LENGTH: 25
<212> TYPE: DNA
<213> ORGANISM: Homo sapiens

<400> SEQUENCE: 258
tcacaagcta ttccctcaaa tctga                                          25

<210> SEQ ID NO 259
<211> LENGTH: 25
<212> TYPE: DNA
<213> ORGANISM: Homo sapiens

<400> SEQUENCE: 259
tgatgagctt tcctttgatc cggac                                          25

<210> SEQ ID NO 260
<211> LENGTH: 25
<212> TYPE: DNA
<213> ORGANISM: Homo sapiens

<400> SEQUENCE: 260
gagacagctg tcttgtgagg gactg 25

<210> SEQ ID NO 261
<211> LENGTH: 25
<212> TYPE: DNA
<213> ORGANISM: Homo sapiens

<400> SEQUENCE: 261
tacacaccac catatatact agctg 25

<210> SEQ ID NO 262
<211> LENGTH: 25
<212> TYPE: DNA
<213> ORGANISM: Homo sapiens

<400> SEQUENCE: 262
gtgtaggtga atgcaaactc catcg 25

<210> SEQ ID NO 263
<211> LENGTH: 25
<212> TYPE: DNA
<213> ORGANISM: Homo sapiens

<400> SEQUENCE: 263
ttcctcttta aacacccgaa gcgca 25

<210> SEQ ID NO 264
<211> LENGTH: 25
<212> TYPE: DNA
<213> ORGANISM: Homo sapiens

<400> SEQUENCE: 264
aactgttcct gactttatac tattt 25

<210> SEQ ID NO 265
<211> LENGTH: 25
<212> TYPE: DNA
<213> ORGANISM: Homo sapiens

<400> SEQUENCE: 265
gcataatgat attcacatcc cctca 25

<210> SEQ ID NO 266
<211> LENGTH: 25
<212> TYPE: DNA
<213> ORGANISM: Homo sapiens

<400> SEQUENCE: 266
tgttgtttct gcactttata ataaa 25

<210> SEQ ID NO 267
<211> LENGTH: 25
<212> TYPE: DNA
<213> ORGANISM: Homo sapiens

<400> SEQUENCE: 267
agaggtgggg ctggatgtct ccatc 25

<210> SEQ ID NO 268
<211> LENGTH: 25
<212> TYPE: DNA
<213> ORGANISM: Homo sapiens

```
<400> SEQUENCE: 268
aagtgcaaag ttattcccca tcttc                                              25

<210> SEQ ID NO 269
<211> LENGTH: 25
<212> TYPE: DNA
<213> ORGANISM: Homo sapiens

<400> SEQUENCE: 269
tacttacacc caaacagatc ctgaa                                              25

<210> SEQ ID NO 270
<211> LENGTH: 25
<212> TYPE: DNA
<213> ORGANISM: Homo sapiens

<400> SEQUENCE: 270
ttgcgtgtgg agctgtattc ccgag                                              25

<210> SEQ ID NO 271
<211> LENGTH: 25
<212> TYPE: DNA
<213> ORGANISM: Homo sapiens

<400> SEQUENCE: 271
ccctttcact gttctcacag gacat                                              25

<210> SEQ ID NO 272
<211> LENGTH: 25
<212> TYPE: DNA
<213> ORGANISM: Homo sapiens

<400> SEQUENCE: 272
gttggctgat attggagtgc tcatt                                              25

<210> SEQ ID NO 273
<211> LENGTH: 25
<212> TYPE: DNA
<213> ORGANISM: Homo sapiens

<400> SEQUENCE: 273
cagcagggtt tcaggttcca atcag                                              25

<210> SEQ ID NO 274
<211> LENGTH: 25
<212> TYPE: DNA
<213> ORGANISM: Homo sapiens

<400> SEQUENCE: 274
ctgtatttgt ggtctctgta tttat                                              25

<210> SEQ ID NO 275
<211> LENGTH: 25
<212> TYPE: DNA
<213> ORGANISM: Homo sapiens

<400> SEQUENCE: 275
acatccaaaa tgacggctgc tatat                                              25

<210> SEQ ID NO 276
<211> LENGTH: 25
<212> TYPE: DNA
<213> ORGANISM: Homo sapiens
```

<400> SEQUENCE: 276
gtggaccctt ctattcatgt tttga                                    25

<210> SEQ ID NO 277
<211> LENGTH: 25
<212> TYPE: DNA
<213> ORGANISM: Homo sapiens

<400> SEQUENCE: 277
gcttaaactt acgtgcctta caggt                                    25

<210> SEQ ID NO 278
<211> LENGTH: 25
<212> TYPE: DNA
<213> ORGANISM: Homo sapiens

<400> SEQUENCE: 278
catgcagact gttagctttt acctt                                    25

<210> SEQ ID NO 279
<211> LENGTH: 25
<212> TYPE: DNA
<213> ORGANISM: Homo sapiens

<400> SEQUENCE: 279
gtcagtgcat aaagacatac tccaa                                    25

<210> SEQ ID NO 280
<211> LENGTH: 25
<212> TYPE: DNA
<213> ORGANISM: Homo sapiens

<400> SEQUENCE: 280
ggagtcctat ttgcagaacc acttt                                    25

<210> SEQ ID NO 281
<211> LENGTH: 25
<212> TYPE: DNA
<213> ORGANISM: Homo sapiens

<400> SEQUENCE: 281
ataaccaacc tattgcctat gagaa                                    25

<210> SEQ ID NO 282
<211> LENGTH: 25
<212> TYPE: DNA
<213> ORGANISM: Homo sapiens

<400> SEQUENCE: 282
cgaattagtc tccagcctct aaata                                    25

<210> SEQ ID NO 283
<211> LENGTH: 25
<212> TYPE: DNA
<213> ORGANISM: Homo sapiens

<400> SEQUENCE: 283
tcgggtctct ccataattca gccca                                    25

<210> SEQ ID NO 284
<211> LENGTH: 25
<212> TYPE: DNA

<213> ORGANISM: Homo sapiens

<400> SEQUENCE: 284
acgattgcct tcagtttgtg ttgtg 25

<210> SEQ ID NO 285
<211> LENGTH: 25
<212> TYPE: DNA
<213> ORGANISM: Homo sapiens

<400> SEQUENCE: 285 aattctttt attggtgcct atatt 25

<210> SEQ ID NO 286
<211> LENGTH: 25
<212> TYPE: DNA
<213> ORGANISM: Homo sapiens

<400> SEQUENCE: 286
aagctcactg gcatggcctt ccgtg 25

<210> SEQ ID NO 287
<211> LENGTH: 25
<212> TYPE: DNA
<213> ORGANISM: Homo sapiens

<400> SEQUENCE: 287
gagatatttc tgaattactg ttgta 25

<210> SEQ ID NO 288
<211> LENGTH: 25
<212> TYPE: DNA
<213> ORGANISM: Homo sapiens

<400> SEQUENCE: 288
tttgacgctg gggctggcat tgccc 25

<210> SEQ ID NO 289
<211> LENGTH: 25
<212> TYPE: DNA
<213> ORGANISM: Homo sapiens

<400> SEQUENCE: 289
ggacagcaga ctgccggtaa cgcgc 25

<210> SEQ ID NO 290
<211> LENGTH: 25
<212> TYPE: DNA
<213> ORGANISM: Homo sapiens

<400> SEQUENCE: 290
gctctgaagt caccaccaaa atgct 25

<210> SEQ ID NO 291
<211> LENGTH: 25
<212> TYPE: DNA
<213> ORGANISM: Homo sapiens

<400> SEQUENCE: 291
ggtgccaatt tcaagttcca agttg 25

<210> SEQ ID NO 292
<211> LENGTH: 25

-continued

```
<212> TYPE: DNA
<213> ORGANISM: Homo sapiens

<400> SEQUENCE: 292
tagggagccg caccttgtca tgtac                                              25

<210> SEQ ID NO 293
<211> LENGTH: 25
<212> TYPE: DNA
<213> ORGANISM: Homo sapiens

<400> SEQUENCE: 293
acgtatattt acctgtgact tgtat                                              25

<210> SEQ ID NO 294
<211> LENGTH: 25
<212> TYPE: DNA
<213> ORGANISM: Homo sapiens

<400> SEQUENCE: 294
taaactgctg cccgtagagg ccttt                                              25

<210> SEQ ID NO 295
<211> LENGTH: 25
<212> TYPE: DNA
<213> ORGANISM: Homo sapiens

<400> SEQUENCE: 295
tggatgttag cggtactctt ccact                                              25

<210> SEQ ID NO 296
<211> LENGTH: 25
<212> TYPE: DNA
<213> ORGANISM: Homo sapiens

<400> SEQUENCE: 296
ttttcctgga tatctgtgta ttttc                                              25

<210> SEQ ID NO 297
<211> LENGTH: 25
<212> TYPE: DNA
<213> ORGANISM: Homo sapiens

<400> SEQUENCE: 297
actgtgcgtt gtacatagtt ctaat                                              25

<210> SEQ ID NO 298
<211> LENGTH: 25
<212> TYPE: DNA
<213> ORGANISM: Homo sapiens

<400> SEQUENCE: 298
gaacactggc cataggaaat gctgt                                              25

<210> SEQ ID NO 299
<211> LENGTH: 25
<212> TYPE: DNA
<213> ORGANISM: Homo sapiens

<400> SEQUENCE: 299
gatcctttct gtaggctaat tcctc                                              25

<210> SEQ ID NO 300
```

```
<211> LENGTH: 25
<212> TYPE: DNA
<213> ORGANISM: Homo sapiens

<400> SEQUENCE: 300
aacgcagcag aacttgccac atcag                                          25

<210> SEQ ID NO 301
<211> LENGTH: 25
<212> TYPE: DNA
<213> ORGANISM: Homo sapiens

<400> SEQUENCE: 301
gaagcttggc tttagtggta gaatg                                          25

<210> SEQ ID NO 302
<211> LENGTH: 25
<212> TYPE: DNA
<213> ORGANISM: Homo sapiens

<400> SEQUENCE: 302
agcctggctc aatatctaat caatg                                          25

<210> SEQ ID NO 303
<211> LENGTH: 25
<212> TYPE: DNA
<213> ORGANISM: Homo sapiens

<400> SEQUENCE: 303
gaacttcaaa catttgggac cacct                                          25

<210> SEQ ID NO 304
<211> LENGTH: 25
<212> TYPE: DNA
<213> ORGANISM: Homo sapiens

<400> SEQUENCE: 304
ccaccctagt gtctcatgtt tgtat                                          25

<210> SEQ ID NO 305
<211> LENGTH: 25
<212> TYPE: DNA
<213> ORGANISM: Homo sapiens

<400> SEQUENCE: 305
tggtgatgtc tgctactatg ccagc                                          25

<210> SEQ ID NO 306
<211> LENGTH: 25
<212> TYPE: DNA
<213> ORGANISM: Homo sapiens

<400> SEQUENCE: 306
aagctggagg ctgagatcgc cacct                                          25

<210> SEQ ID NO 307
<211> LENGTH: 25
<212> TYPE: DNA
<213> ORGANISM: Homo sapiens

<400> SEQUENCE: 307
cactttaacc cacgcttcaa tgaga                                          25
```

```
<210> SEQ ID NO 308
<211> LENGTH: 25
<212> TYPE: DNA
<213> ORGANISM: Homo sapiens

<400> SEQUENCE: 308
tggaatgagt ctcctttagt ttcag                                          25

<210> SEQ ID NO 309
<211> LENGTH: 25
<212> TYPE: DNA
<213> ORGANISM: Homo sapiens

<400> SEQUENCE: 309
agagacatgt accttgacca tcgtc                                          25

<210> SEQ ID NO 310
<211> LENGTH: 25
<212> TYPE: DNA
<213> ORGANISM: Homo sapiens

<400> SEQUENCE: 310
tggaaatcct ctaggaggct cctcc                                          25

<210> SEQ ID NO 311
<211> LENGTH: 25
<212> TYPE: DNA
<213> ORGANISM: Homo sapiens

<400> SEQUENCE: 311
tgtgtgggtg ctgataattg tgtat                                          25

<210> SEQ ID NO 312
<211> LENGTH: 25
<212> TYPE: DNA
<213> ORGANISM: Homo sapiens

<400> SEQUENCE: 312
tactcttcca tcatctagaa ttgtt                                          25

<210> SEQ ID NO 313
<211> LENGTH: 25
<212> TYPE: DNA
<213> ORGANISM: Homo sapiens

<400> SEQUENCE: 313
gcaccctcag ggtcttaagg tcttc                                          25

<210> SEQ ID NO 314
<211> LENGTH: 25
<212> TYPE: DNA
<213> ORGANISM: Homo sapiens

<400> SEQUENCE: 314
gtacacagtc tgttttctat ttgtt                                          25

<210> SEQ ID NO 315
<211> LENGTH: 25
<212> TYPE: DNA
<213> ORGANISM: Homo sapiens

<400> SEQUENCE: 315
tgggctgcct tatattgtgt gtgtg                                          25
```

```
<210> SEQ ID NO 316
<211> LENGTH: 25
<212> TYPE: DNA
<213> ORGANISM: Homo sapiens

<400> SEQUENCE: 316
taacccagac ttaatcttga atgat                                  25

<210> SEQ ID NO 317
<211> LENGTH: 25
<212> TYPE: DNA
<213> ORGANISM: Homo sapiens

<400> SEQUENCE: 317
gagacttcgg cggaccatta ggaat                                  25

<210> SEQ ID NO 318
<211> LENGTH: 25
<212> TYPE: DNA
<213> ORGANISM: Homo sapiens

<400> SEQUENCE: 318
atgcacgtga aacttaacac tttat                                  25

<210> SEQ ID NO 319
<211> LENGTH: 25
<212> TYPE: DNA
<213> ORGANISM: Homo sapiens

<400> SEQUENCE: 319
agttgaacag tgtgccctag ctttt                                  25

<210> SEQ ID NO 320
<211> LENGTH: 25
<212> TYPE: DNA
<213> ORGANISM: Homo sapiens

<400> SEQUENCE: 320
gatcttgtat tcagtcaggt taaaa                                  25

<210> SEQ ID NO 321
<211> LENGTH: 25
<212> TYPE: DNA
<213> ORGANISM: Homo sapiens

<400> SEQUENCE: 321
ccaaagtggt cagggtggcc tctgg                                  25

<210> SEQ ID NO 322
<211> LENGTH: 25
<212> TYPE: DNA
<213> ORGANISM: Homo sapiens

<400> SEQUENCE: 322
ggacgagtcg gaccgaggct aggac                                  25

<210> SEQ ID NO 323
<211> LENGTH: 25
<212> TYPE: DNA
<213> ORGANISM: Homo sapiens

<400> SEQUENCE: 323
atttgtggcc actcactttg tagga                                  25
```

<210> SEQ ID NO 324
<211> LENGTH: 25
<212> TYPE: DNA
<213> ORGANISM: Homo sapiens

<400> SEQUENCE: 324
tcttgctcca aagggctccg tggag                                          25

<210> SEQ ID NO 325
<211> LENGTH: 25
<212> TYPE: DNA
<213> ORGANISM: Homo sapiens

<400> SEQUENCE: 325
ctcctccatg agtctgacat ctcgg                                          25

<210> SEQ ID NO 326
<211> LENGTH: 25
<212> TYPE: DNA
<213> ORGANISM: Homo sapiens

<400> SEQUENCE: 326
ggttgaggag aggctccaga cccgc                                          25

<210> SEQ ID NO 327
<211> LENGTH: 25
<212> TYPE: DNA
<213> ORGANISM: Homo sapiens

<400> SEQUENCE: 327
acagcaactt gtcaaaccta agcat                                          25

<210> SEQ ID NO 328
<211> LENGTH: 25
<212> TYPE: DNA
<213> ORGANISM: Homo sapiens

<400> SEQUENCE: 328
acgcagagga cgtctctatg ccggt                                          25

<210> SEQ ID NO 329
<211> LENGTH: 25
<212> TYPE: DNA
<213> ORGANISM: Homo sapiens

<400> SEQUENCE: 329
gtagtcattc atttctagct gtaca                                          25

<210> SEQ ID NO 330
<211> LENGTH: 25
<212> TYPE: DNA
<213> ORGANISM: Homo sapiens

<400> SEQUENCE: 330
gtagctgatg aagtatgtcg cattt                                          25

<210> SEQ ID NO 331
<211> LENGTH: 25
<212> TYPE: DNA
<213> ORGANISM: Homo sapiens

<400> SEQUENCE: 331

```
gatgatcttc tgtggtgctt aagga                                        25

<210> SEQ ID NO 332
<211> LENGTH: 25
<212> TYPE: DNA
<213> ORGANISM: Homo sapiens

<400> SEQUENCE: 332
ctgtgattgc tgccaggcac tgttc                                        25

<210> SEQ ID NO 333
<211> LENGTH: 25
<212> TYPE: DNA
<213> ORGANISM: Homo sapiens

<400> SEQUENCE: 333
ttcacgcgga aatacacgct gcccc                                        25

<210> SEQ ID NO 334
<211> LENGTH: 25
<212> TYPE: DNA
<213> ORGANISM: Homo sapiens

<400> SEQUENCE: 334
tcatctgctg gtccgtggga cggtg                                        25

<210> SEQ ID NO 335
<211> LENGTH: 25
<212> TYPE: DNA
<213> ORGANISM: Homo sapiens

<400> SEQUENCE: 335
gaaggagagc catgcgtact ttcta                                        25

<210> SEQ ID NO 336
<211> LENGTH: 25
<212> TYPE: DNA
<213> ORGANISM: Homo sapiens

<400> SEQUENCE: 336
gtgtatagtg ttttaccctc ttctt                                        25

<210> SEQ ID NO 337
<211> LENGTH: 25
<212> TYPE: DNA
<213> ORGANISM: Homo sapiens

<400> SEQUENCE: 337
caggactttt gttccaggtt gccag                                        25

<210> SEQ ID NO 338
<211> LENGTH: 25
<212> TYPE: DNA
<213> ORGANISM: Homo sapiens

<400> SEQUENCE: 338
gtgcagtttc tgacacttgt tgttg                                        25

<210> SEQ ID NO 339
<211> LENGTH: 25
<212> TYPE: DNA
<213> ORGANISM: Homo sapiens

<400> SEQUENCE: 339
```
gggagcaccg tgatggagag gacag              25

<210> SEQ ID NO 340
<211> LENGTH: 25
<212> TYPE: DNA
<213> ORGANISM: Homo sapiens

<400> SEQUENCE: 340
aaggccaaga tcaccatcgt ggcag              25

<210> SEQ ID NO 341
<211> LENGTH: 25
<212> TYPE: DNA
<213> ORGANISM: Homo sapiens

<400> SEQUENCE: 341
tattcaaatg gcccctccag aaagt              25

<210> SEQ ID NO 342
<211> LENGTH: 25
<212> TYPE: DNA
<213> ORGANISM: Homo sapiens

<400> SEQUENCE: 342
aagccacatc tgagcacttc aagac              25

<210> SEQ ID NO 343
<211> LENGTH: 25
<212> TYPE: DNA
<213> ORGANISM: Homo sapiens

<400> SEQUENCE: 343
gttccaagaa ctctggtgtc tgacc              25

<210> SEQ ID NO 344
<211> LENGTH: 25
<212> TYPE: DNA
<213> ORGANISM: Homo sapiens

<400> SEQUENCE: 344
gaggatcatg cccttagcaa gtact              25

<210> SEQ ID NO 345
<211> LENGTH: 25
<212> TYPE: DNA
<213> ORGANISM: Homo sapiens

<400> SEQUENCE: 345
ggtctacgcc tattacaacc tggag              25

<210> SEQ ID NO 346
<211> LENGTH: 25
<212> TYPE: DNA
<213> ORGANISM: Homo sapiens

<400> SEQUENCE: 346
aatcgttctc cttacaatca agttc              25

<210> SEQ ID NO 347
<211> LENGTH: 25
<212> TYPE: DNA
<213> ORGANISM: Homo sapiens

<400> SEQUENCE: 347
ggaactaggc tcttatgtgt gcctt 25

<210> SEQ ID NO 348
<211> LENGTH: 25
<212> TYPE: DNA
<213> ORGANISM: Homo sapiens

<400> SEQUENCE: 348
tctgtcctcc taagaaatct gccca 25

<210> SEQ ID NO 349
<211> LENGTH: 25
<212> TYPE: DNA
<213> ORGANISM: Homo sapiens

<400> SEQUENCE: 349
gaggctcagt tagcaacctg tgttg 25

<210> SEQ ID NO 350
<211> LENGTH: 25
<212> TYPE: DNA
<213> ORGANISM: Homo sapiens

<400> SEQUENCE: 350
agactgtccc tgaaacctag tactg 25

<210> SEQ ID NO 351
<211> LENGTH: 25
<212> TYPE: DNA
<213> ORGANISM: Homo sapiens

<400> SEQUENCE: 351
actttctgca tgttgatgcc cgaag 25

<210> SEQ ID NO 352
<211> LENGTH: 25
<212> TYPE: DNA
<213> ORGANISM: Homo sapiens

<400> SEQUENCE: 352
gttcttgtat tgtattgccc agggg 25

<210> SEQ ID NO 353
<211> LENGTH: 25
<212> TYPE: DNA
<213> ORGANISM: Homo sapiens

<400> SEQUENCE: 353
aaaaaccgca gcccaggttc tgatc 25

<210> SEQ ID NO 354
<211> LENGTH: 25
<212> TYPE: DNA
<213> ORGANISM: Homo sapiens

<400> SEQUENCE: 354
gacatgaacg gctgttactc acgcc 25

<210> SEQ ID NO 355
<211> LENGTH: 25
<212> TYPE: DNA
<213> ORGANISM: Homo sapiens

```
<400> SEQUENCE: 355
tgttcttggc gctgtatgtg caggc                                25

<210> SEQ ID NO 356
<211> LENGTH: 25
<212> TYPE: DNA
<213> ORGANISM: Homo sapiens

<400> SEQUENCE: 356
cttctacagg cttttgggaa gtagg                                25

<210> SEQ ID NO 357
<211> LENGTH: 25
<212> TYPE: DNA
<213> ORGANISM: Homo sapiens

<400> SEQUENCE: 357
tggaggacac agatgactct ttggt                                25

<210> SEQ ID NO 358
<211> LENGTH: 25
<212> TYPE: DNA
<213> ORGANISM: Homo sapiens

<400> SEQUENCE: 358
gagtgggtgg ggaattttct cctct                                25

<210> SEQ ID NO 359
<211> LENGTH: 25
<212> TYPE: DNA
<213> ORGANISM: Homo sapiens

<400> SEQUENCE: 359
ctgcaccttc atcagcggca tgatg                                25

<210> SEQ ID NO 360
<211> LENGTH: 25
<212> TYPE: DNA
<213> ORGANISM: Homo sapiens

<400> SEQUENCE: 360
tataaaccac tcttcaacag ctggc                                25

<210> SEQ ID NO 361
<211> LENGTH: 25
<212> TYPE: DNA
<213> ORGANISM: Homo sapiens

<400> SEQUENCE: 361
aatacatccg atgcgtagat tcttg                                25

<210> SEQ ID NO 362
<211> LENGTH: 25
<212> TYPE: DNA
<213> ORGANISM: Homo sapiens

<400> SEQUENCE: 362
tggcttagcc tgggcaggtc gtgtc                                25

<210> SEQ ID NO 363
<211> LENGTH: 25
<212> TYPE: DNA
```

<213> ORGANISM: Homo sapiens

<400> SEQUENCE: 363
gagcagggtc tctctaaagg ggact                                          25

<210> SEQ ID NO 364
<211> LENGTH: 25
<212> TYPE: DNA
<213> ORGANISM: Homo sapiens

<400> SEQUENCE: 364
gtctctgagt tacaaaagtg ctaat                                          25

<210> SEQ ID NO 365
<211> LENGTH: 25
<212> TYPE: DNA
<213> ORGANISM: Homo sapiens

<400> SEQUENCE: 365
accagttttt ggcttactcc tgaga                                          25

<210> SEQ ID NO 366
<211> LENGTH: 25
<212> TYPE: DNA
<213> ORGANISM: Homo sapiens

<400> SEQUENCE: 366
ttgtctacac tcaggctgca gtatt                                          25

<210> SEQ ID NO 367
<211> LENGTH: 25
<212> TYPE: DNA
<213> ORGANISM: Homo sapiens

<400> SEQUENCE: 367
tcctgagaga tacctcacat tccaa                                          25

<210> SEQ ID NO 368
<211> LENGTH: 25
<212> TYPE: DNA
<213> ORGANISM: Homo sapiens

<400> SEQUENCE: 368
ggttagcctt agtttctcag acttg                                          25

<210> SEQ ID NO 369
<211> LENGTH: 25
<212> TYPE: DNA
<213> ORGANISM: Homo sapiens

<400> SEQUENCE: 369
tgtcctcatc tctgcaaagt tcagc                                          25

<210> SEQ ID NO 370
<211> LENGTH: 25
<212> TYPE: DNA
<213> ORGANISM: Homo sapiens

<400> SEQUENCE: 370
ttcccaagga caggcttcag catca                                          25

<210> SEQ ID NO 371
<211> LENGTH: 25

```
<212> TYPE: DNA
<213> ORGANISM: Homo sapiens

<400> SEQUENCE: 371
ctcctacgca gatgctgtca ctggc                                          25

<210> SEQ ID NO 372
<211> LENGTH: 25
<212> TYPE: DNA
<213> ORGANISM: Homo sapiens

<400> SEQUENCE: 372
tgagcaaggg ggcccgaatc gacca                                          25

<210> SEQ ID NO 373
<211> LENGTH: 25
<212> TYPE: DNA
<213> ORGANISM: Homo sapiens

<400> SEQUENCE: 373
aagcctgctc tcttgcaaag acagc                                          25

<210> SEQ ID NO 374
<211> LENGTH: 25
<212> TYPE: DNA
<213> ORGANISM: Homo sapiens

<400> SEQUENCE: 374
taactataag gtgcctcagt tttcc                                          25

<210> SEQ ID NO 375
<211> LENGTH: 25
<212> TYPE: DNA
<213> ORGANISM: Homo sapiens

<400> SEQUENCE: 375
catatggcat ctctcaactt ttctt                                          25

<210> SEQ ID NO 376
<211> LENGTH: 25
<212> TYPE: DNA
<213> ORGANISM: Homo sapiens

<400> SEQUENCE: 376
gaaagttcag ccagaatctt cgtcc                                          25

<210> SEQ ID NO 377
<211> LENGTH: 25
<212> TYPE: DNA
<213> ORGANISM: Homo sapiens

<400> SEQUENCE: 377
gggcagcttc ctaatatgct ttaca                                          25

<210> SEQ ID NO 378
<211> LENGTH: 25
<212> TYPE: DNA
<213> ORGANISM: Homo sapiens

<400> SEQUENCE: 378
gcctgtcttg agtagacttg gaccc                                          25

<210> SEQ ID NO 379
```

```
<211> LENGTH: 25
<212> TYPE: DNA
<213> ORGANISM: Homo sapiens

<400> SEQUENCE: 379
gatccacctc atatgtgagt ccgtc                                     25

<210> SEQ ID NO 380
<211> LENGTH: 25
<212> TYPE: DNA
<213> ORGANISM: Homo sapiens

<400> SEQUENCE: 380
cgctgctgtg tcactcatga ctgtt                                     25

<210> SEQ ID NO 381
<211> LENGTH: 25
<212> TYPE: DNA
<213> ORGANISM: Homo sapiens

<400> SEQUENCE: 381
gcctgttgaa ggtacatcgt ttgca                                     25

<210> SEQ ID NO 382
<211> LENGTH: 25
<212> TYPE: DNA
<213> ORGANISM: Homo sapiens

<400> SEQUENCE: 382
tctcccgatt cccaactgag tgtta                                     25

<210> SEQ ID NO 383
<211> LENGTH: 25
<212> TYPE: DNA
<213> ORGANISM: Homo sapiens

<400> SEQUENCE: 383
aggcaatttt aatcccctgc actag                                     25

<210> SEQ ID NO 384
<211> LENGTH: 25
<212> TYPE: DNA
<213> ORGANISM: Homo sapiens

<400> SEQUENCE: 384
ggacaaactg ccagttttgt ttcct                                     25

<210> SEQ ID NO 385
<211> LENGTH: 25
<212> TYPE: DNA
<213> ORGANISM: Homo sapiens

<400> SEQUENCE: 385
gttcttcaat cagctggcac acact                                     25

<210> SEQ ID NO 386
<211> LENGTH: 25
<212> TYPE: DNA
<213> ORGANISM: Homo sapiens

<400> SEQUENCE: 386
accacccagg aaaccatcga caaga                                     25
```

```
<210> SEQ ID NO 387
<211> LENGTH: 25
<212> TYPE: DNA
<213> ORGANISM: Homo sapiens

<400> SEQUENCE: 387
aaggacagaa cattgccttc ctcgt                                     25

<210> SEQ ID NO 388
<211> LENGTH: 25
<212> TYPE: DNA
<213> ORGANISM: Homo sapiens

<400> SEQUENCE: 388
ggatatacaa gttctgtggt ttcag                                     25

<210> SEQ ID NO 389
<211> LENGTH: 25
<212> TYPE: DNA
<213> ORGANISM: Homo sapiens

<400> SEQUENCE: 389
gtggttggca ctagactggt ggcag                                     25

<210> SEQ ID NO 390
<211> LENGTH: 25
<212> TYPE: DNA
<213> ORGANISM: Homo sapiens

<400> SEQUENCE: 390
atgtacttgt tctacctgga ttgtc                                     25

<210> SEQ ID NO 391
<211> LENGTH: 25
<212> TYPE: DNA
<213> ORGANISM: Homo sapiens

<400> SEQUENCE: 391
cgcggctgca tgacactgga ggtca                                     25

<210> SEQ ID NO 392
<211> LENGTH: 25
<212> TYPE: DNA
<213> ORGANISM: Homo sapiens

<400> SEQUENCE: 392
ggtgcccgga tccagagtgt gaaga                                     25

<210> SEQ ID NO 393
<211> LENGTH: 25
<212> TYPE: DNA
<213> ORGANISM: Homo sapiens

<400> SEQUENCE: 393
ctccatccta tgctgctaca attgc                                     25

<210> SEQ ID NO 394
<211> LENGTH: 25
<212> TYPE: DNA
<213> ORGANISM: Homo sapiens

<400> SEQUENCE: 394
tgaatgccag tccagatgtg cctag                                     25
```

<210> SEQ ID NO 395
<211> LENGTH: 25
<212> TYPE: DNA
<213> ORGANISM: Homo sapiens

<400> SEQUENCE: 395
ttacattcat ttaacctgcc gatta                                    25

<210> SEQ ID NO 396
<211> LENGTH: 25
<212> TYPE: DNA
<213> ORGANISM: Homo sapiens

<400> SEQUENCE: 396
cacccagtgg tactttggtg cctac                                    25

<210> SEQ ID NO 397
<211> LENGTH: 25
<212> TYPE: DNA
<213> ORGANISM: Homo sapiens

<400> SEQUENCE: 397
agtgctggtc actaaccaac aaggt                                    25

<210> SEQ ID NO 398
<211> LENGTH: 25
<212> TYPE: DNA
<213> ORGANISM: Homo sapiens

<400> SEQUENCE: 398
ctctctgaaa cgcttcctat aactc                                    25

<210> SEQ ID NO 399
<211> LENGTH: 25
<212> TYPE: DNA
<213> ORGANISM: Homo sapiens

<400> SEQUENCE: 399
ttgtcagttc tcaatttcct gtgtt                                    25

<210> SEQ ID NO 400
<211> LENGTH: 25
<212> TYPE: DNA
<213> ORGANISM: Homo sapiens

<400> SEQUENCE: 400
attatcgctt tatgtttttg gttat                                    25

<210> SEQ ID NO 401
<211> LENGTH: 25
<212> TYPE: DNA
<213> ORGANISM: Homo sapiens

<400> SEQUENCE: 401
ggggctcaag ggcaagatca gcgag                                    25

<210> SEQ ID NO 402
<211> LENGTH: 25
<212> TYPE: DNA
<213> ORGANISM: Homo sapiens

<400> SEQUENCE: 402
gaataggtat cttgagcttg gttct                                    25

```
<210> SEQ ID NO 403
<211> LENGTH: 25
<212> TYPE: DNA
<213> ORGANISM: Homo sapiens

<400> SEQUENCE: 403
acactcgctt ctggaacgtc tgagg                                              25

<210> SEQ ID NO 404
<211> LENGTH: 25
<212> TYPE: DNA
<213> ORGANISM: Homo sapiens

<400> SEQUENCE: 404
aatctatatt tgtcttccga tcaac                                              25

<210> SEQ ID NO 405
<211> LENGTH: 25
<212> TYPE: DNA
<213> ORGANISM: Homo sapiens

<400> SEQUENCE: 405
acaaggccca ggctggggcc agggc                                              25
```